(12) United States Patent
Zhang et al.

(10) Patent No.: US 8,603,468 B2
(45) Date of Patent: Dec. 10, 2013

(54) NEUTRALIZATION OF HCV

(75) Inventors: Pei Zhang, Rockville, MD (US);
Marian Major, Alexandria, VA (US);
Stephen Feinstone, Washington, DC (US)

(73) Assignee: The United States of America, as Represented by the Secretary of the Department of Health and Human Services, Washington, DC (US)

( * ) Notice: Subject to any disclaimer, the term of this patent is extended or adjusted under 35 U.S.C. 154(b) by 589 days.

(21) Appl. No.: 12/741,612

(22) PCT Filed: Nov. 4, 2008

(86) PCT No.: PCT/US2008/082368
§ 371 (c)(1),
(2), (4) Date: May 6, 2010

(87) PCT Pub. No.: WO2009/061739
PCT Pub. Date: May 14, 2009

(65) Prior Publication Data
US 2010/0247522 A1    Sep. 30, 2010

Related U.S. Application Data

(60) Provisional application No. 61/002,031, filed on Nov. 6, 2007.

(51) Int. Cl.
*A61K 39/395* (2006.01)
*A01N 1/02* (2006.01)

(52) U.S. Cl.
USPC ...... 424/130.1; 435/2; 424/139.1; 424/147.1; 424/149.1

(58) Field of Classification Search
None
See application file for complete search history.

(56) References Cited

U.S. PATENT DOCUMENTS

| 5,053,224 | A | 10/1991 | Koprowski et al. |
| 6,469,143 | B2 | 10/2002 | Sallberg |
| 6,933,366 | B2 | 8/2005 | Sallberg et al. |
| 7,019,111 | B2 | 3/2006 | Sallberg |
| 7,318,926 | B2 | 1/2008 | Sallberg |

OTHER PUBLICATIONS

Naicker et al. Design and synthesis of αGal-conjugated peptide T20 as novel antiviral agent for HIV-immunotargeting. Org. Biomol. Chem., 2004,2, 660-664.*
International Search Report and Written Opinion; International Application No. PCT/US2008/082368; International Filing Date Nov. 4, 2008; Applicant's Reference NIH363.001VP; Date of Mailing Feb. 27, 2009; 13 pages.

Bartosch, et al.; "In Vitro Assay for Neutralizing Antibody to Hepatitis C Virus: Evidence for Broadly Conserved Neutralization Epitopes"; Proc Natl Acad Sci USA; 100; pp. 14199-14204; ( 2003).
Brown, et al.; Cross-Genotype Characterization of Genetic Diversity and Molecular Adaptation in Hepatitis C Virus Envelope Glycoprotein Genes; J Gen Virol; 88; pp. 458-469; (2007).
Clayton, et al.; "Analysis of Antigenicity and Topology of E2 Glycoprotein Present on Recombinant Hepatitis C Virus-Like Particles"; J Virol; 76; pp. 7672-7682; (2002).
Eren, et al.; "Preclinical Evaluation of Two Neutralizing Human Monoclonal Antibodies Against Hepatitis C Virus (HCV): a Potential Treatment to Prevent HCV Reinfection in Liver Transplant Patients"; J Virol; 80; pp. 2654-2664; (2006).
Farci et al.; "Prevention of Hepatitis C Virus Infection in Chimpanzees by Hyperimmmune Serum Against the Hypervariable Region 1 of the Envelope 2 Protein"; Proc Natl Acad Sci USA; 93; pp. 15394-15399; (1996).
Flint,et al.; "Characterization of Hepatitis C Virus E2 Glycoprotein Interaction with a Putative Cellular Receptor, CD81"; J Virol; 73; pp. 6235-6244; (1999).
Hsu, et al.; "Hepatitis C Virus Glycoproteins Mediate pH-Dependent Cell Entry of Pseudotyped Retroviral Particles"; Proc Natl Acad Sci USA; 100; pp. 7271-7276; (2003).
Law, et al.; "Broadly Neutralizing Antibodies Protect Against Hepatitis C Virus Quasispecies Challenge"; Nature Medicine; 14; pp. 25-27; 2008.
Logvinoff, et al.; Neutralizing Antibody Response During Acute and Chronic Hepatitis C Virus Infection; Proc Natl Acad Sci USA; 101; pp. 10149-10154; (2004).
Meunier, et al.; "Evidence for Cross-Genotype Neutralization of Hepatitis C Virus Pseudo-Particles and Enhancement of Infectivity by Apolipoprotein C1"; Proc Natl Acad Sci USA; 102; pp. 4560-4565; (2005).
Owsianka, et al.; "Monoclonal Antibody AP33 Defines A Broadly Neutralizing Epitope on the Hepatitis C Virus E2 Envelope Glycoprotein"; J Virol; 79; pp. 11095-11104; (2005).
Owsianka, et al.; "Functional Analysis of Hepatitis C Virus E2 Glycoproteins and Virus-Like Particles Reveals Structural Dissimilarities Between Different Forms of E2"; J Gen Virol; 82; pp. 1877-1883; (2001).
Owsianka, et al.; "Identification of Conserved Residues in the E2 Envelope Glycoprotein of the Hepatitis C Virus That Are Critical for CD81 Binding"; J Virol; 80; pp. 8695-8704; (2006).
Perotti, et al.; "Identification of a Broadly Cross-Reacting and Neutralizing Human Monoclonal Antibody Directed Against the Hepatitis C Virus E2 Protein"; J Virol; 82; pp. 1047-1052; (2008).
Schofield, et al.; "Human Monoclonal Antibodies That React With the E2 Glycoprotein of Hepatitis C Virus and Possess Neutralizing Activity"; Hepatology; 42; pp. 1055-1062; (2005).
Tarr, et al.; "Characterization of the Hepatitis C Virus E2 Epitope Defined by the Broadly Neutralizing Monoclonal Antibody AP33"; Hepatology; 43; pp. 592-601; (2006).
Tarr, et al.; "Determination of the Human Antibody Response to the Epitope Defined by the Hepatitis C Virus-Neutralizing Monoclonal Antibody AP33"; J Gen Virol; 88; pp. 2991-3001; (2007).

(Continued)

Primary Examiner — Michelle S Horning
(74) Attorney, Agent, or Firm — Cantor Colburn LLP

(57) ABSTRACT

Aspects of the present invention concern compositions that induce and/or improve an immune response to hepatitis C virus (HCV). Methods of making and using compositions that include epitopes of the HCV E2 structural protein involved in promoting or inhibiting neutralization of HCV are provided.

9 Claims, 15 Drawing Sheets

(56) References Cited

OTHER PUBLICATIONS

Figure 1:
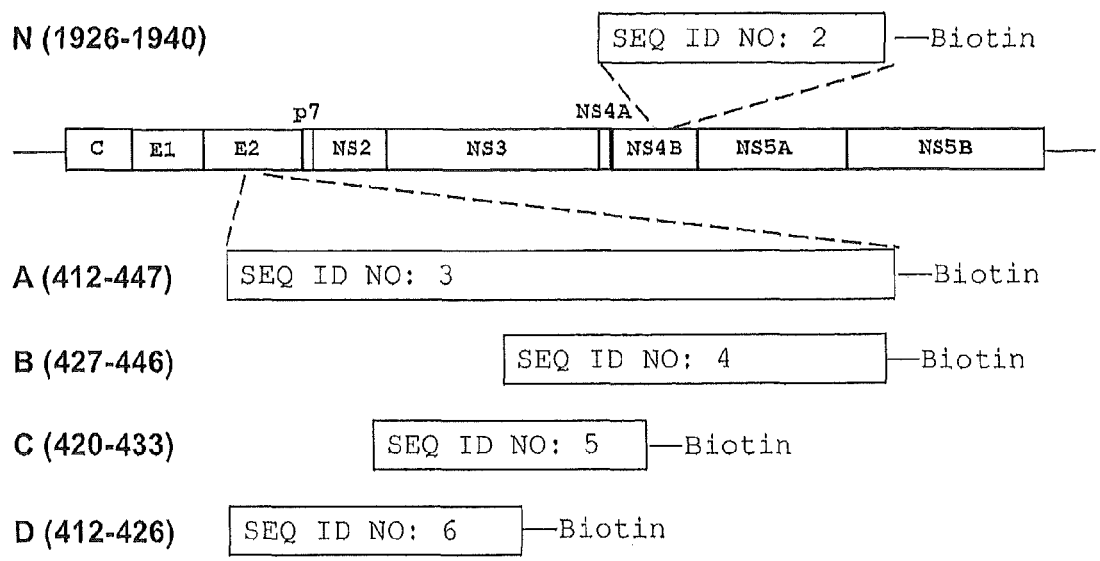

Yu, et al.; "Neutralizing Antibodies to Hepatitis C Virus (HCV) in Immune Globulins Derived from Anti-HCV-Positive Plastma"; Proc Natl Acad Sci USA; 101; pp. 7705-7710; (2004).

Zeisel, et al.; "Neutralizing Antibodies in Hepatitis C Virus Infection"; World Journal of Gastroenterology; 13; pp. 4824-4830; (2007).

Zhang, et al.; "Hepatitis C Virus Epitope-Specific Neutralizing Antibodies in Igs Prepared From Human Plasma"; Proc Natl Acad Sci USA; 104; pp. 8449-8454; (2007).

Triyatni, et al.; "Structural Features of Envelope Proteins on Hepatitis C Virus-like Particles as Determined by Anti-envelope Monoclonal Antibodies and CD81 Binding"; Virology; 298; pp. 124-132; (2002).

* cited by examiner

| Ig Eluate | Corresponding Reactive Peptide | Relative Level of Reactivity |
|---|---|---|
| $A_E$ | A, B | A > B |
| $B_E$ | A, B | A > B |
| $C_E$ | -  | |
| $D_E$ | A, D | A = D |
| $N_E$ | N | |

|  | Epitope I | Epitope II |  |
|---|---|---|---|
| Peptide A | QLINTNNGSWHINSTALNCNES | LNTGWLAGLFYQHKF | (SEQ ID NO:3) |
| Peptide B |  | LNCNESLNTGWLAGLFYQHK | (SEQ ID NO:4) |
| Peptide C | WHINSTALNCNESL |  | (SEQ ID NO:5) |
| Peptide D | QLINTNGSWHINSTA |  | (SEQ ID NO:6) |

FIG. 4

HCV E2        412
              QLINTNGSWHINSTALNCNESLNTGWLAGLFYQHKF          (SEQ ID NO: 8)
Cluster 1                          HITHYFVVPSVS             (SEQ ID NO: 9)
Cluster 2               ATWSRPIYFDIT                        (SEQ ID NO: 10)
Key residues         441 LFY  443        447
                                      LFY

FIG. 5A

```
         Epitope I                           Epitope II
      403                                451
H77   LTPGAKQNIQLINTNGSWHINSTALNCNESLNTGWLAGLFYQHKFNSSG     (SEQ ID NO: 45)
1a    --S---------------------R------A--D---V----Y-R-----
1b    FRA-PS-K----V-----------R------D------F-A---VRN----
2a    FDM-PR-K----------------R------D------FI-S---T-S---
2b    -SP-S--K-S--------------R------D--Q---F-S---VNN----
3a    FS----S-RLE-------------R------R------I--F----Y----T-
4     F------V---S------------R------D------F-------HYS---
5     F---PR--L-V-------------R------QD--Q--FI---L-FN----
6     F-S---R-L---------------R------D--Q---FI-S---FN----
```

FIG. 5B

```
             427                      446
Peptide B  LNCNESLNTGWLAGLFYQHK    (SEQ ID NO: 4)
B mutant   LNCNESLNTGNAPATVK       (SEQ ID NO: 12)
```

```
                  446            426
Epitope I    QLINTNGSWHINSTA              (SEQ ID NO:13)
Phage        QPLVHVLPSWID    ┐-o--o-      (SEQ ID NO:14)
             HNAQPMTSWPIN*   ┘ QL SW      (SEQ ID NO:15)
             SYASSHLNPRQLP   ┐-o-         (SEQ ID NO:16)
             QLGTLVAGVHPR*   ┘ QL         (SEQ ID NO:17)
             SHHDNSWVTDDY*   ┐---o-       (SEQ ID NO:18)
             ATWGPPDHAGPH    ┘    SW      (SEQ ID NO:19)
```
*FIG. 10A*
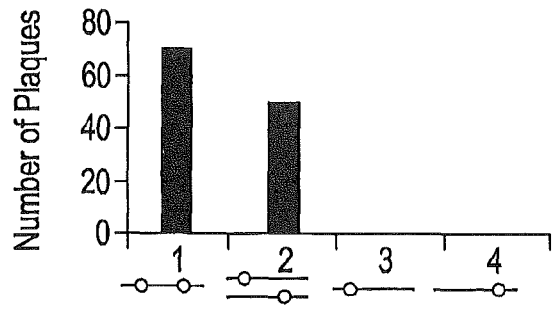
*FIG. 10B*
```
Epitope I    QLINTNGSWHINSTA              (SEQ ID NO:13)
QL>AA        AA-------------
Q>A          A--------------
L>A          -A-------------
SW>AA        -------AA------
W>A          --------A------
HIN>AAA      ---------AAA---
```
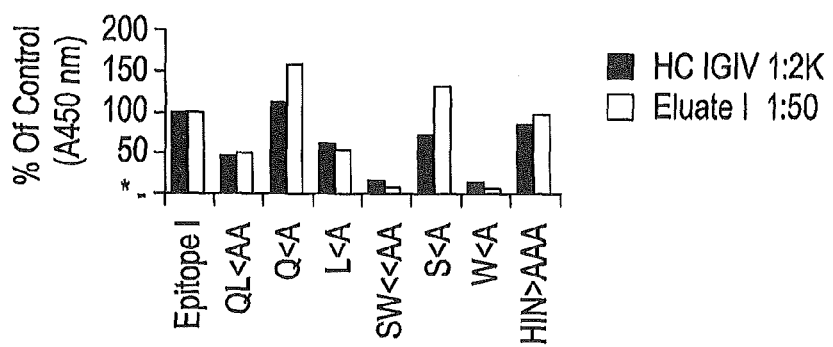
*FIG. 10C*

| | | |
|---|---|---|
| Epitope I | ⁴¹²QLINTNGSWHINSTA⁴²⁶ | SEQ ID NO: 6 |
| Epitope II | ⁴²⁷LNCNESLNTGWLAGLFYQHK⁴⁴⁶ | SEQ ID NO: 22 |
| 1a (H77) | ⁴³⁴NTGWLAGLFYQHK | SEQ ID NO: 23 |
| 1b | ⁴³⁴NTGFLAALFYVRNK | SEQ ID NO: 24 |
| 2a | ⁴³⁴NTGFIASLFYTHSK | SEQ ID NO: 25 |
| 2b | ⁴³⁴QTGFLASLFYVNNK | SEQ ID NO: 26 |

Epitope II        LNCNESLNTGWLAGLFYQHK   (SEQ ID NO: 22)
Epitope II Mutant LNCNESLNTGWL<u>NAPATV</u>K    (SEQ ID NO: 27)

SEQUENCE LISTING

```
<160> NUMBER OF SEQ ID NOS: 45

<210> SEQ ID NO 1
<211> LENGTH: 4
<212> TYPE: PRT
<213> ORGANISM: Hepatitis C virus

<400> SEQUENCE: 1

Gln Asn Gly Ser
1

<210> SEQ ID NO 2
<211> LENGTH: 15
<212> TYPE: PRT
<213> ORGANISM: Hepatitis C virus
```

```
<400> SEQUENCE: 2

Gly Asn His Val Ser Pro Thr His Tyr Val Pro Glu Ser Asp Lys
1               5                  10                  15

<210> SEQ ID NO 3
<211> LENGTH: 37
<212> TYPE: PRT
<213> ORGANISM: Hepatitis C virus

<400> SEQUENCE: 3

Gln Leu Ile Asn Thr Asn Gly Ser Trp His Ile Asn Ser Thr Ala
1               5                  10                  15

Leu Asn Cys Asn Glu Ser Leu Asn Thr Gly Trp Leu Ala Gly Leu Phe
            20                  25                  30

Tyr Gln His Lys Phe
        35

<210> SEQ ID NO 4
<211> LENGTH: 20
<212> TYPE: PRT
<213> ORGANISM: Hepatitis C virus

<400> SEQUENCE: 4

Leu Asn Cys Asn Glu Ser Leu Asn Thr Gly Trp Leu Ala Gly Leu Phe
1               5                  10                  15

Tyr Gln His Lys
        20

<210> SEQ ID NO 5
<211> LENGTH: 14
<212> TYPE: PRT
<213> ORGANISM: Hepatitis C virus

<400> SEQUENCE: 5

Trp His Ile Asn Ser Thr Ala Leu Asn Cys Asn Glu Ser Leu
1               5                  10

<210> SEQ ID NO 6
<211> LENGTH: 15
<212> TYPE: PRT
<213> ORGANISM: Hepatitis C virus

<400> SEQUENCE: 6

Gln Leu Ile Asn Thr Asn Gly Ser Trp His Ile Asn Ser Thr Ala
1               5                  10                  15

<210> SEQ ID NO 7
<211> LENGTH: 49
<212> TYPE: PRT
<213> ORGANISM: Hepatitis C virus

<400> SEQUENCE: 7

Leu Thr Pro Gly Ala Lys Gln Asn Ile Gln Leu Ile Asn Thr Asn Gly
1               5                  10                  15

Ser Trp His Ile Asn Ser Thr Ala Leu Asn Cys Asn Glu Ser Leu Asn
            20                  25                  30

Thr Gly Trp Leu Ala Gly Leu Phe Tyr Gln His Lys Phe Asn Ser Ser
        35                  40                  45

Gly

<210> SEQ ID NO 8
<211> LENGTH: 36
```

```
<212> TYPE: PRT
<213> ORGANISM: Hepatitis C virus

<400> SEQUENCE: 8

Gln Leu Ile Asn Thr Asn Gly Ser Trp His Ile Asn Ser Thr Ala Leu
1               5                   10                  15

Asn Cys Asn Glu Ser Leu Asn Thr Gly Trp Leu Ala Gly Leu Phe Tyr
            20                  25                  30

Gln His Lys Phe
            35

<210> SEQ ID NO 9
<211> LENGTH: 12
<212> TYPE: PRT
<213> ORGANISM: Hepatitis C virus

<400> SEQUENCE: 9

His Ile Thr His Tyr Phe Val Val Pro Ser Val Ser
1               5                   10

<210> SEQ ID NO 10
<211> LENGTH: 12
<212> TYPE: PRT
<213> ORGANISM: Hepatitis C virus

<400> SEQUENCE: 10

Ala Thr Trp Ser Arg Pro Ile Tyr Phe Asp Ile Thr
1               5                   10

<210> SEQ ID NO 11
<211> LENGTH: 3011
<212> TYPE: PRT
<213> ORGANISM: Hepatitis C virus

<400> SEQUENCE: 11

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190
```

-continued

```
Gln Val Arg Asn Ser Ser Gly Leu Tyr His Val Thr Asn Asp Cys Pro
        195                 200                 205

Asn Ser Ser Ile Val Tyr Glu Ala Asp Ala Ile Leu His Thr Pro
    210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Asp Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Val Ala Gln
                325                 330                 335

Leu Leu Arg Ile Pro Gln Ala Ile Met Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Leu Phe Ala Gly Val Asp Ala Glu
    370                 375                 380

Thr His Val Thr Gly Gly Ser Ala Gly Arg Thr Thr Ala Gly Leu Val
385                 390                 395                 400

Gly Leu Leu Thr Pro Gly Ala Lys Gln Asn Ile Gln Leu Ile Asn Thr
                405                 410                 415

Asn Gly Ser Trp His Ile Asn Ser Thr Ala Leu Asn Cys Asn Glu Ser
            420                 425                 430

Leu Asn Thr Gly Trp Leu Ala Gly Leu Phe Tyr Gln His Lys Phe Asn
        435                 440                 445

Ser Ser Gly Cys Pro Glu Arg Leu Ala Ser Cys Arg Arg Leu Thr Asp
    450                 455                 460

Phe Ala Gln Gly Trp Gly Pro Ile Ser Tyr Ala Asn Gly Ser Gly Leu
465                 470                 475                 480

Asp Glu Arg Pro Tyr Cys Trp His Tyr Pro Pro Arg Pro Cys Gly Ile
                485                 490                 495

Val Pro Ala Lys Ser Val Cys Gly Pro Val Tyr Cys Phe Thr Pro Ser
            500                 505                 510

Pro Val Val Val Gly Thr Thr Asp Arg Ser Gly Ala Pro Thr Tyr Ser
        515                 520                 525

Trp Gly Ala Asn Asp Thr Asp Val Phe Val Leu Asn Asn Thr Arg Pro
    530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Val Gly Asn
                565                 570                 575

Asn Thr Leu Leu Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Met
        595                 600                 605

Val Asp Tyr Pro Tyr Arg Leu Trp His Tyr Pro Cys Thr Ile Asn Tyr
610                 615                 620
```

```
Thr Ile Phe Lys Val Arg Met Tyr Val Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Ser Thr Thr Gln Trp
        660                 665                 670

Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
        690                 695                 700

Val Gly Ser Ser Ile Ala Ser Trp Ala Ile Lys Trp Glu Tyr Val Val
705                 710                 715                 720

Leu Leu Phe Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
        755                 760                 765

Leu Val Phe Phe Cys Phe Ala Trp Tyr Leu Lys Gly Arg Trp Val Pro
770                 775                 780

Gly Ala Val Tyr Ala Phe Tyr Gly Met Trp Pro Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Met Trp Leu Gln Tyr
        835                 840                 845

Phe Leu Thr Arg Val Glu Ala Gln Leu His Val Trp Val Pro Pro Leu
        850                 855                 860

Asn Val Arg Gly Gly Arg Asp Ala Val Ile Leu Leu Met Cys Val Val
865                 870                 875                 880

His Pro Thr Leu Val Phe Asp Ile Thr Lys Leu Leu Leu Ala Ile Phe
                885                 890                 895

Gly Pro Leu Trp Ile Leu Gln Ala Ser Leu Leu Lys Val Pro Tyr Phe
                900                 905                 910

Val Arg Val Gln Gly Leu Leu Arg Ile Cys Ala Leu Ala Arg Lys Ile
            915                 920                 925

Ala Gly Gly His Tyr Val Gln Met Ala Ile Ile Lys Leu Gly Ala Leu
        930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Arg Met Glu Thr Lys Leu Ile Thr Trp Gly Ala Asp Thr Ala Ala
            980                 985                 990

Cys Gly Asp Ile Ile Asn Gly Leu Pro Val Ser Ala Arg Arg Gly Gln
        995                 1000                1005

Glu Ile Leu Leu Gly Pro Ala Asp Gly Met Val Ser Lys Gly Trp
        1010                1015                1020

Arg Leu Leu Ala Pro Ile Thr Ala Tyr Ala Gln Gln Thr Arg Gly
        1025                1030                1035

Leu Leu Gly Cys Ile Ile Thr Ser Leu Thr Gly Arg Asp Lys Asn
```

-continued

```
            1040                1045                1050

Gln Val Glu Gly Glu Val Gln Ile Val Ser Thr Ala Thr Gln Thr
    1055                1060                1065

Phe Leu Ala Thr Cys Ile Asn Gly Val Cys Trp Thr Val Tyr His
    1070                1075                1080

Gly Ala Gly Thr Arg Thr Ile Ala Ser Pro Lys Gly Pro Val Ile
    1085                1090                1095

Gln Met Tyr Thr Asn Val Asp Gln Asp Leu Val Gly Trp Pro Ala
    1100                1105                1110

Pro Gln Gly Ser Arg Ser Leu Thr Pro Cys Thr Cys Gly Ser Ser
    1115                1120                1125

Asp Leu Tyr Leu Val Thr Arg His Ala Asp Val Ile Pro Val Arg
    1130                1135                1140

Arg Arg Gly Asp Ser Arg Gly Ser Leu Leu Ser Pro Arg Pro Ile
    1145                1150                1155

Ser Tyr Leu Lys Gly Ser Ser Gly Gly Pro Leu Leu Cys Pro Ala
    1160                1165                1170

Gly His Ala Val Gly Leu Phe Arg Ala Ala Val Cys Thr Arg Gly
    1175                1180                1185

Val Ala Lys Ala Val Asp Phe Ile Pro Val Glu Asn Leu Glu Thr
    1190                1195                1200

Thr Met Arg Ser Pro Val Phe Thr Asp Asn Ser Ser Pro Pro Ala
    1205                1210                1215

Val Pro Gln Ser Phe Gln Val Ala His Leu His Ala Pro Thr Gly
    1220                1225                1230

Ser Gly Lys Ser Thr Lys Val Pro Ala Ala Tyr Ala Ala Gln Gly
    1235                1240                1245

Tyr Lys Val Leu Val Leu Asn Pro Ser Val Ala Ala Thr Leu Gly
    1250                1255                1260

Phe Gly Ala Tyr Met Ser Lys Ala His Gly Val Asp Pro Asn Ile
    1265                1270                1275

Arg Thr Gly Val Arg Thr Ile Thr Thr Gly Ser Pro Ile Thr Tyr
    1280                1285                1290

Ser Thr Tyr Gly Lys Phe Leu Ala Asp Gly Gly Cys Ser Gly Gly
    1295                1300                1305

Ala Tyr Asp Ile Ile Ile Cys Asp Glu Cys His Ser Thr Asp Ala
    1310                1315                1320

Thr Ser Ile Leu Gly Ile Gly Thr Val Leu Asp Gln Ala Glu Thr
    1325                1330                1335

Ala Gly Ala Arg Leu Val Val Leu Ala Thr Ala Thr Pro Pro Gly
    1340                1345                1350

Ser Val Thr Val Ser His Pro Asn Ile Glu Glu Val Ala Leu Ser
    1355                1360                1365

Thr Thr Gly Glu Ile Pro Phe Tyr Gly Lys Ala Ile Pro Leu Glu
    1370                1375                1380

Val Ile Lys Gly Gly Arg His Leu Ile Phe Cys His Ser Lys Lys
    1385                1390                1395

Lys Cys Asp Glu Leu Ala Ala Lys Leu Val Ala Leu Gly Ile Asn
    1400                1405                1410

Ala Val Ala Tyr Tyr Arg Gly Leu Asp Val Ser Val Ile Pro Thr
    1415                1420                1425

Ser Gly Asp Val Val Val Ser Thr Asp Ala Leu Met Thr Gly
    1430                1435                1440
```

-continued

Phe Thr Gly Asp Phe Asp Ser Val Ile Asp Cys Asn Thr Cys Val
1445                1450                1455

Thr Gln Thr Val Asp Phe Ser Leu Asp Pro Thr Phe Thr Ile Glu
1460                1465                1470

Thr Thr Thr Leu Pro Gln Asp Ala Val Ser Arg Thr Gln Arg Arg
1475                1480                1485

Gly Arg Thr Gly Arg Gly Lys Pro Gly Ile Tyr Arg Phe Val Ala
1490                1495                1500

Pro Gly Glu Arg Pro Ser Gly Met Phe Asp Ser Ser Val Leu Cys
1505                1510                1515

Glu Cys Tyr Asp Ala Gly Cys Ala Trp Tyr Glu Leu Thr Pro Ala
1520                1525                1530

Glu Thr Thr Val Arg Leu Arg Ala Tyr Met Asn Thr Pro Gly Leu
1535                1540                1545

Pro Val Cys Gln Asp His Leu Glu Phe Trp Glu Gly Val Phe Thr
1550                1555                1560

Gly Leu Thr His Ile Asp Ala His Phe Leu Ser Gln Thr Lys Gln
1565                1570                1575

Ser Gly Glu Asn Phe Pro Tyr Leu Val Ala Tyr Gln Ala Thr Val
1580                1585                1590

Cys Ala Arg Ala Gln Ala Pro Pro Pro Ser Trp Asp Gln Met Trp
1595                1600                1605

Lys Cys Leu Ile Arg Leu Lys Pro Thr Leu His Gly Pro Thr Pro
1610                1615                1620

Leu Leu Tyr Arg Leu Gly Ala Val Gln Asn Glu Val Thr Leu Thr
1625                1630                1635

His Pro Ile Thr Lys Tyr Ile Met Thr Cys Met Ser Ala Asp Leu
1640                1645                1650

Glu Val Val Thr Ser Thr Trp Val Leu Val Gly Gly Val Leu Ala
1655                1660                1665

Ala Leu Ala Ala Tyr Cys Leu Ser Thr Gly Cys Val Val Ile Val
1670                1675                1680

Gly Arg Ile Val Leu Ser Gly Lys Pro Ala Ile Ile Pro Asp Arg
1685                1690                1695

Glu Val Leu Tyr Gln Glu Phe Asp Glu Met Glu Glu Cys Ser Gln
1700                1705                1710

His Leu Pro Tyr Ile Glu Gln Gly Met Met Leu Ala Glu Gln Phe
1715                1720                1725

Lys Gln Lys Ala Leu Gly Leu Leu Gln Thr Ala Ser Arg Gln Ala
1730                1735                1740

Glu Val Ile Thr Pro Ala Val Gln Thr Asn Trp Gln Lys Leu Glu
1745                1750                1755

Val Phe Trp Ala Lys His Met Trp Asn Phe Ile Ser Gly Ile Gln
1760                1765                1770

Tyr Leu Ala Gly Leu Ser Thr Leu Pro Gly Asn Pro Ala Ile Ala
1775                1780                1785

Ser Leu Met Ala Phe Thr Ala Ala Val Thr Ser Pro Leu Thr Thr
1790                1795                1800

Gly Gln Thr Leu Leu Phe Asn Ile Leu Gly Gly Trp Val Ala Ala
1805                1810                1815

Gln Leu Ala Ala Pro Gly Ala Ala Thr Ala Phe Val Gly Ala Gly
1820                1825                1830

Leu Ala Gly Ala Ala Ile Gly Ser Val Gly Leu Gly Lys Val Leu
1835                1840                1845

Val Asp Ile Leu Ala Gly Tyr Gly Ala Val Ala Gly Ala Leu
1850               1855              1860

Val Ala Phe Lys Ile Met Ser Gly Glu Val Pro Ser Thr Glu Asp
1865               1870              1875

Leu Val Asn Leu Leu Pro Ala Ile Leu Ser Pro Gly Ala Leu Val
1880               1885              1890

Val Gly Val Val Cys Ala Ala Ile Leu Arg Arg His Val Gly Pro
1895               1900              1905

Gly Glu Gly Ala Val Gln Trp Met Asn Arg Leu Ile Ala Phe Ala
1910               1915              1920

Ser Arg Gly Asn His Val Ser Pro Thr His Tyr Val Pro Glu Ser
1925               1930              1935

Asp Ala Ala Ala Arg Val Thr Ala Ile Leu Ser Ser Leu Thr Val
1940               1945              1950

Thr Gln Leu Leu Arg Arg Leu His Gln Trp Ile Ser Ser Glu Cys
1955               1960              1965

Thr Thr Pro Cys Ser Gly Ser Trp Leu Arg Asp Ile Trp Asp Trp
1970               1975              1980

Ile Cys Glu Val Leu Ser Asp Phe Lys Thr Trp Leu Lys Ala Lys
1985               1990              1995

Leu Met Pro Gln Leu Pro Gly Ile Pro Phe Val Ser Cys Gln Arg
2000               2005              2010

Gly Tyr Arg Gly Val Trp Arg Gly Asp Gly Ile Met His Thr Arg
2015               2020              2025

Cys His Cys Gly Ala Glu Ile Thr Gly His Val Lys Asn Gly Thr
2030               2035              2040

Met Arg Ile Val Gly Pro Arg Thr Cys Arg Asn Met Trp Ser Gly
2045               2050              2055

Thr Phe Pro Ile Asn Ala Tyr Thr Thr Gly Pro Cys Thr Pro Leu
2060               2065              2070

Pro Ala Pro Asn Tyr Lys Phe Ala Leu Trp Arg Val Ser Ala Glu
2075               2080              2085

Glu Tyr Val Glu Ile Arg Arg Val Gly Asp Phe His Tyr Val Ser
2090               2095              2100

Gly Met Thr Thr Asp Asn Leu Lys Cys Pro Cys Gln Ile Pro Ser
2105               2110              2115

Pro Glu Phe Phe Thr Glu Leu Asp Gly Val Arg Leu His Arg Phe
2120               2125              2130

Ala Pro Pro Cys Lys Pro Leu Leu Arg Glu Glu Val Ser Phe Arg
2135               2140              2145

Val Gly Leu His Glu Tyr Pro Val Gly Ser Gln Leu Pro Cys Glu
2150               2155              2160

Pro Glu Pro Asp Val Ala Val Leu Thr Ser Met Leu Thr Asp Pro
2165               2170              2175

Ser His Ile Thr Ala Glu Ala Ala Gly Arg Arg Leu Ala Arg Gly
2180               2185              2190

Ser Pro Pro Ser Met Ala Ser Ser Ser Ala Ser Gln Leu Ser Ala
2195               2200              2205

Pro Ser Leu Lys Ala Thr Cys Thr Ala Asn His Asp Ser Pro Asp
2210               2215              2220

Ala Glu Leu Ile Glu Ala Asn Leu Leu Trp Arg Gln Glu Met Gly
2225               2230              2235

Gly Asn Ile Thr Arg Val Glu Ser Glu Asn Lys Val Val Ile Leu

-continued

```
                2240                2245                2250

Asp Ser Phe Asp Pro Leu Val Ala Glu Glu Asp Glu Arg Glu Val
    2255                2260                2265

Ser Val Pro Ala Glu Ile Leu Arg Lys Ser Arg Arg Phe Ala Arg
    2270                2275                2280

Ala Leu Pro Val Trp Ala Arg Pro Asp Tyr Asn Pro Pro Leu Val
    2285                2290                2295

Glu Thr Trp Lys Lys Pro Asp Tyr Glu Pro Pro Val Val His Gly
    2300                2305                2310

Cys Pro Leu Pro Pro Pro Arg Ser Pro Pro Val Pro Pro Pro Arg
    2315                2320                2325

Lys Lys Arg Thr Val Val Leu Thr Glu Ser Thr Leu Ser Thr Ala
    2330                2335                2340

Leu Ala Glu Leu Ala Thr Lys Ser Phe Gly Ser Ser Ser Thr Ser
    2345                2350                2355

Gly Ile Thr Gly Asp Asn Thr Thr Thr Ser Ser Glu Pro Ala Pro
    2360                2365                2370

Ser Gly Cys Pro Pro Asp Ser Asp Val Glu Ser Tyr Ser Ser Met
    2375                2380                2385

Pro Pro Leu Glu Gly Glu Pro Gly Asp Pro Asp Leu Ser Asp Gly
    2390                2395                2400

Ser Trp Ser Thr Val Ser Ser Gly Ala Asp Thr Glu Asp Val Val
    2405                2410                2415

Cys Cys Ser Met Ser Tyr Ser Trp Thr Gly Ala Leu Val Thr Pro
    2420                2425                2430

Cys Ala Ala Glu Glu Gln Lys Leu Pro Ile Asn Ala Leu Ser Asn
    2435                2440                2445

Ser Leu Leu Arg His His Asn Leu Val Tyr Ser Thr Thr Ser Arg
    2450                2455                2460

Ser Ala Cys Gln Arg Gln Lys Lys Val Thr Phe Asp Arg Leu Gln
    2465                2470                2475

Val Leu Asp Ser His Tyr Gln Asp Val Leu Lys Glu Val Lys Ala
    2480                2485                2490

Ala Ala Ser Lys Val Lys Ala Asn Leu Leu Ser Val Glu Glu Ala
    2495                2500                2505

Cys Ser Leu Thr Pro Pro His Ser Ala Lys Ser Lys Phe Gly Tyr
    2510                2515                2520

Gly Ala Lys Asp Val Arg Cys His Ala Arg Lys Ala Val Ala His
    2525                2530                2535

Ile Asn Ser Val Trp Lys Asp Leu Leu Glu Asp Ser Val Thr Pro
    2540                2545                2550

Ile Asp Thr Thr Ile Met Ala Lys Asn Glu Val Phe Cys Val Gln
    2555                2560                2565

Pro Glu Lys Gly Gly Arg Lys Pro Ala Arg Leu Ile Val Phe Pro
    2570                2575                2580

Asp Leu Gly Val Arg Val Cys Glu Lys Met Ala Leu Tyr Asp Val
    2585                2590                2595

Val Ser Lys Leu Pro Leu Ala Val Met Gly Ser Ser Tyr Gly Phe
    2600                2605                2610

Gln Tyr Ser Pro Gly Gln Arg Val Glu Phe Leu Val Gln Ala Trp
    2615                2620                2625

Lys Ser Lys Lys Thr Pro Met Gly Phe Ser Tyr Asp Thr Arg Cys
    2630                2635                2640
```

```
Phe Asp Ser Thr Val Thr Glu Ser Asp Ile Arg Thr Glu Glu Ala
2645                2650                2655

Ile Tyr Gln Cys Cys Asp Leu Asp Pro Gln Ala Arg Val Ala Ile
2660                2665                2670

Lys Ser Leu Thr Glu Arg Leu Tyr Val Gly Gly Pro Leu Thr Asn
2675                2680                2685

Ser Arg Gly Glu Asn Cys Gly Tyr Arg Arg Cys Arg Ala Ser Gly
2690                2695                2700

Val Leu Thr Thr Ser Cys Gly Asn Thr Leu Thr Cys Tyr Ile Lys
2705                2710                2715

Ala Arg Ala Ala Cys Arg Ala Ala Gly Leu Gln Asp Cys Thr Met
2720                2725                2730

Leu Val Cys Gly Asp Asp Leu Val Val Ile Cys Glu Ser Ala Gly
2735                2740                2745

Val Gln Glu Asp Ala Ala Ser Leu Arg Ala Phe Thr Glu Ala Met
2750                2755                2760

Thr Arg Tyr Ser Ala Pro Pro Gly Asp Pro Pro Gln Pro Glu Tyr
2765                2770                2775

Asp Leu Glu Leu Ile Thr Ser Cys Ser Ser Asn Val Ser Val Ala
2780                2785                2790

His Asp Gly Ala Gly Lys Arg Val Tyr Tyr Leu Thr Arg Asp Pro
2795                2800                2805

Thr Thr Pro Leu Ala Arg Ala Ala Trp Glu Thr Ala Arg His Thr
2810                2815                2820

Pro Val Asn Ser Trp Leu Gly Asn Ile Ile Met Phe Ala Pro Thr
2825                2830                2835

Leu Trp Ala Arg Met Ile Leu Met Thr His Phe Phe Ser Val Leu
2840                2845                2850

Ile Ala Arg Asp Gln Leu Glu Gln Ala Leu Asn Cys Glu Ile Tyr
2855                2860                2865

Gly Ala Cys Tyr Ser Ile Glu Pro Leu Asp Leu Pro Pro Ile Ile
2870                2875                2880

Gln Arg Leu His Gly Leu Ser Ala Phe Ser Leu His Ser Tyr Ser
2885                2890                2895

Pro Gly Glu Ile Asn Arg Val Ala Ala Cys Leu Arg Lys Leu Gly
2900                2905                2910

Val Pro Pro Leu Arg Ala Trp Arg His Arg Ala Arg Ser Val Arg
2915                2920                2925

Ala Arg Leu Leu Ser Arg Gly Gly Arg Ala Ala Ile Cys Gly Lys
2930                2935                2940

Tyr Leu Phe Asn Trp Ala Val Arg Thr Lys Leu Lys Leu Thr Pro
2945                2950                2955

Ile Ala Ala Ala Gly Arg Leu Asp Leu Ser Gly Trp Phe Thr Ala
2960                2965                2970

Gly Tyr Ser Gly Gly Asp Ile Tyr His Ser Val Ser His Ala Arg
2975                2980                2985

Pro Arg Trp Phe Trp Phe Cys Leu Leu Leu Leu Ala Ala Gly Val
2990                2995                3000

Gly Ile Tyr Leu Leu Pro Asn Arg
3005                3010

<210> SEQ ID NO 12
<211> LENGTH: 17
<212> TYPE: PRT
<213> ORGANISM: Hepatitis C virus
```

```
<400> SEQUENCE: 12

Leu Asn Cys Asn Glu Ser Leu Asn Thr Gly Asn Ala Pro Ala Thr Val
1               5                   10                  15

Lys

<210> SEQ ID NO 13
<211> LENGTH: 15
<212> TYPE: PRT
<213> ORGANISM: Hepatitis C virus

<400> SEQUENCE: 13

Gln Leu Ile Asn Thr Asn Gly Ser Trp His Ile Asn Ser Thr Ala
1               5                   10                  15

<210> SEQ ID NO 14
<211> LENGTH: 12
<212> TYPE: PRT
<213> ORGANISM: Artificial Sequence
<220> FEATURE:
<223> OTHER INFORMATION: SEQUENCE FROM PHAGE DISPLAY LIBRARY

<400> SEQUENCE: 14

Gln Pro Leu Val His Val Leu Pro Ser Trp Ile Asp
1               5                   10

<210> SEQ ID NO 15
<211> LENGTH: 12
<212> TYPE: PRT
<213> ORGANISM: Artificial Sequence
<220> FEATURE:
<223> OTHER INFORMATION: SEQUENCE FROM PHAGE DISPLAY LIBRARY

<400> SEQUENCE: 15

His Asn Ala Gln Pro Met Thr Ser Trp Pro Ile Asn
1               5                   10

<210> SEQ ID NO 16
<211> LENGTH: 13
<212> TYPE: PRT
<213> ORGANISM: Artificial Sequence
<220> FEATURE:
<223> OTHER INFORMATION: SEQUENCE FROM PHAGE DISPLAY LIBRARY

<400> SEQUENCE: 16

Ser Tyr Ala Ser Ser His Leu Asn Pro Arg Gln Leu Pro
1               5                   10

<210> SEQ ID NO 17
<211> LENGTH: 12
<212> TYPE: PRT
<213> ORGANISM: Artificial Sequence
<220> FEATURE:
<223> OTHER INFORMATION: SEQUENCE FROM PHAGE DISPLAY LIBRARY

<400> SEQUENCE: 17

Gln Leu Gly Thr Leu Val Ala Gly Val His Pro Arg
1               5                   10

<210> SEQ ID NO 18
<211> LENGTH: 12
<212> TYPE: PRT
<213> ORGANISM: Artificial Sequence
<220> FEATURE:
<223> OTHER INFORMATION: SEQUENCE FROM PHAGE DISPLAY LIBRARY

<400> SEQUENCE: 18
```

```
Ser His His Asp Asn Ser Trp Val Thr Asp Asp Tyr
1               5                   10
```

```
<210> SEQ ID NO 19
<211> LENGTH: 12
<212> TYPE: PRT
<213> ORGANISM: Artificial Sequence
<220> FEATURE:
<223> OTHER INFORMATION: SEQUENCE FROM PHAGE DISPLAY LIBRARY

<400> SEQUENCE: 19
```

```
Ala Thr Trp Gly Pro Pro Asp His Ala Gly Pro His
1               5                   10
```

```
<210> SEQ ID NO 20
<211> LENGTH: 12
<212> TYPE: PRT
<213> ORGANISM: Artificial Sequence
<220> FEATURE:
<223> OTHER INFORMATION: SEQUENCE FROM PAHE DISPLAY LIBRARY

<400> SEQUENCE: 20
```

```
Thr Met Asn Trp Ile His Pro Asn Gly Gly Pro Gly
1               5                   10
```

```
<210> SEQ ID NO 21
<211> LENGTH: 12
<212> TYPE: PRT
<213> ORGANISM: Artificial Sequence
<220> FEATURE:
<223> OTHER INFORMATION: SEQUENCE FROM PHAGE DISPLAY LIBRARY

<400> SEQUENCE: 21
```

```
Lys Trp Thr Thr Asn His Arg Tyr Val Pro Leu His
1               5                   10
```

```
<210> SEQ ID NO 22
<211> LENGTH: 20
<212> TYPE: PRT
<213> ORGANISM: Hepatitis C virus

<400> SEQUENCE: 22
```

```
Leu Asn Cys Asn Glu Ser Leu Asn Thr Gly Trp Leu Ala Gly Leu Phe
1               5                   10                  15

Tyr Gln His Lys
            20
```

```
<210> SEQ ID NO 23
<211> LENGTH: 13
<212> TYPE: PRT
<213> ORGANISM: Hepatitis C virus

<400> SEQUENCE: 23
```

```
Asn Thr Gly Trp Leu Ala Gly Leu Phe Tyr Gln His Lys
1               5                   10
```

```
<210> SEQ ID NO 24
<211> LENGTH: 14
<212> TYPE: PRT
<213> ORGANISM: Hepatitis C virus

<400> SEQUENCE: 24
```

```
Asn Thr Gly Phe Leu Ala Ala Leu Phe Tyr Val Arg Asn Lys
1               5                   10
```

```
<210> SEQ ID NO 25
<211> LENGTH: 14
<212> TYPE: PRT
<213> ORGANISM: Hepatitis C virus

<400> SEQUENCE: 25

Asn Thr Gly Phe Ile Ala Ser Leu Phe Tyr Thr His Ser Lys
1               5                   10

<210> SEQ ID NO 26
<211> LENGTH: 14
<212> TYPE: PRT
<213> ORGANISM: Hepatitis C virus

<400> SEQUENCE: 26

Gln Thr Gly Phe Leu Ala Ser Leu Phe Tyr Val Asn Asn Lys
1               5                   10

<210> SEQ ID NO 27
<211> LENGTH: 19
<212> TYPE: PRT
<213> ORGANISM: Hepatitis C virus

<400> SEQUENCE: 27

Leu Asn Cys Asn Glu Ser Leu Asn Thr Gly Trp Leu Asn Ala Pro Ala
1               5                   10                  15

Thr Val Lys

<210> SEQ ID NO 28
<211> LENGTH: 6
<212> TYPE: PRT
<213> ORGANISM: Hepatitis C virus

<400> SEQUENCE: 28

Asn Ala Pro Ala Thr Val
1               5

<210> SEQ ID NO 29
<211> LENGTH: 9
<212> TYPE: PRT
<213> ORGANISM: Hepatitis C virus

<400> SEQUENCE: 29

Gln Leu Asp Ser Phe Thr Asn Gly Ser
1               5

<210> SEQ ID NO 30
<211> LENGTH: 13
<212> TYPE: PRT
<213> ORGANISM: Hepatitis C virus

<400> SEQUENCE: 30

Asn Thr Gly Trp Leu Ala Gly Leu Phe Tyr Gln His Lys
1               5                   10

<210> SEQ ID NO 31
<211> LENGTH: 13
<212> TYPE: PRT
<213> ORGANISM: Hepatitis C virus

<400> SEQUENCE: 31

Asp Thr Gly Trp Val Ala Gly Leu Phe Tyr Tyr His Arg
1               5                   10

<210> SEQ ID NO 32
```

```
<211> LENGTH: 8
<212> TYPE: PRT
<213> ORGANISM: Hepatitis C virus

<400> SEQUENCE: 32

Gln Leu Val Asn Thr Asn Gly Ser
1               5

<210> SEQ ID NO 33
<211> LENGTH: 13
<212> TYPE: PRT
<213> ORGANISM: Hepatitis C virus

<400> SEQUENCE: 33

Asn Thr Gly Phe Leu Ala Ala Leu Phe Tyr Val Arg Asn
1               5                   10

<210> SEQ ID NO 34
<211> LENGTH: 13
<212> TYPE: PRT
<213> ORGANISM: Hepatitis C virus

<400> SEQUENCE: 34

Asn Thr Gly Phe Ile Ala Ser Leu Phe Tyr Thr His Ser
1               5                   10

<210> SEQ ID NO 35
<211> LENGTH: 8
<212> TYPE: PRT
<213> ORGANISM: Hepatitis C virus

<400> SEQUENCE: 35

Ser Leu Ile Asn Thr Asn Gly Ser
1               5

<210> SEQ ID NO 36
<211> LENGTH: 13
<212> TYPE: PRT
<213> ORGANISM: Hepatitis C virus

<400> SEQUENCE: 36

Asn Thr Gly Phe Leu Ala Gly Leu Phe Tyr Tyr His Lys
1               5                   10

<210> SEQ ID NO 37
<211> LENGTH: 8
<212> TYPE: PRT
<213> ORGANISM: Hepatitis C virus

<400> SEQUENCE: 37

Glu Leu Ile Asn Thr Asn Gly Ser
1               5

<210> SEQ ID NO 38
<211> LENGTH: 13
<212> TYPE: PRT
<213> ORGANISM: Hepatitis C virus

<400> SEQUENCE: 38

Asn Thr Gly Phe Leu Ala Gly Leu Phe Tyr Tyr His Lys
1               5                   10

<210> SEQ ID NO 39
<211> LENGTH: 8
<212> TYPE: PRT
<213> ORGANISM: Hepatitis C virus
```

```
<400> SEQUENCE: 39

Gln Leu Ile Asn Ser Asn Gly Ser
1               5

<210> SEQ ID NO 40
<211> LENGTH: 13
<212> TYPE: PRT
<213> ORGANISM: Hepatitis C virus

<400> SEQUENCE: 40

Asn Thr Gly Phe Leu Ala Gly Leu Phe Tyr His Tyr Ser
1               5                   10

<210> SEQ ID NO 41
<211> LENGTH: 8
<212> TYPE: PRT
<213> ORGANISM: Hepatitis C virus

<400> SEQUENCE: 41

Gln Val Ile Asn Thr Asn Gly Ser
1               5

<210> SEQ ID NO 42
<211> LENGTH: 13
<212> TYPE: PRT
<213> ORGANISM: Hepatitis C virus

<400> SEQUENCE: 42

Gln Thr Gly Phe Ile Ala Gly Leu Leu Tyr Phe Asn Lys
1               5                   10

<210> SEQ ID NO 43
<211> LENGTH: 13
<212> TYPE: PRT
<213> ORGANISM: Hepatitis C virus

<400> SEQUENCE: 43

Gln Thr Gly Phe Ile Ala Ser Leu Phe Tyr Phe Asn Lys
1               5                   10

<210> SEQ ID NO 44
<211> LENGTH: 7
<212> TYPE: PRT
<213> ORGANISM: Hepatitis C virus

<400> SEQUENCE: 44

Ala Gly Leu Phe Tyr Gln His
1               5

<210> SEQ ID NO 45
<211> LENGTH: 49
<212> TYPE: PRT
<213> ORGANISM: Hepatitis C virus

<400> SEQUENCE: 45

Leu Thr Pro Gly Ala Lys Gln Asn Ile Gln Leu Ile Asn Thr Asn Gly
1               5                   10                  15

Ser Trp His Ile Asn Ser Thr Ala Leu Asn Cys Asn Glu Ser Leu Asn
            20                  25                  30

Thr Gly Trp Leu Ala Gly Leu Phe Tyr Gln His Lys Phe Asn Ser Ser
        35                  40                  45

Gly
```

NEUTRALIZATION OF HCV

CROSS REFERENCE TO RELATED APPLICATIONS

This is a U.S. national stage of application No. PCT/US2008/082368, filed on 4 Nov. 2008. Priority under 35 U.S.C. §119(a) and 35 U.S.C. §365(b) is claimed from U.S. Provisional Patent Application No. 61/002,031, filed 6 Nov. 2007, the disclosure of which is also incorporated herein by reference.

FIELD OF THE INVENTION

Aspects of the present invention concern compositions that induce and/or improve an immune response to hepatitis C virus (HCV). Methods of making and using compositions that include epitopes of the HCV E2 structural protein involved in promoting and inhibiting neutralization of HCV are provided.

BACKGROUND

More than 70% of the estimated 170 million people worldwide who are infected with hepatitis C virus (HCV) develop chronic infection. Chronic HCV infections can lead to chronic liver disease, cirrhosis, and hepatocellular carcinoma. Chronic HCV infection is the leading indication for liver transplantation in the United States (Alter, H. J. et al. 2000 *Semin Liver Dis* 20:17-35). Antiviral treatment of HCV is now successful in about half of the cases, but it is expensive, requires long-term treatment, and is associated with serious side effects. There is no vaccine currently available for the prevention of HCV infection.

HCV is a positive-sense RNA virus belonging to the Flaviviridae family. It encodes a single polyprotein of ≈3,000 aa. Through the action of a combination of host and viral proteases, the polyprotein is cleaved into structural proteins (core, E1, E2, and p7) and nonstructural proteins (NS2-NS5B). The two envelope glycoproteins, E1 and E2, are believed to form heterodimers/oligomers on the surface of HCV particles that participate in the process of cell entry (Bartosch, B. et al, 2003 *J Exp Med* 197:633-642).

The mechanisms that govern the clinical outcomes of HCV infection are not well understood. Whereas cellular immune responses have been considered essential for controlling viral infection (Thimme, R. et al. 2003 *Hepatology* 37:1472-1474), the role of the humoral immune response remains to be defined. Increasing evidence demonstrates that neutralizing antibodies are present in patients with chronic hepatitis C (Bartosch, B. et al. 2003 *Proc Natl Acad Sci USA* 100:14199-14204; Meunier, J. C. et al. 2005 *Proc Natl Acad Sci USA* 102:4560-4565), and that epitopes located within the E2 protein are important for HCV neutralization (Farci, P. et al. 1996 *Proc Natl Acad Sci USA* 93:15394-15399; Triyatni, M. et al. 2002 *Virology* 298:124-132; Hsu, M. et al. 2003 *Proc Natl Acad Sci USA* 100:7271-7276; Logvinoff, C. et al. 2004 *Proc Natl Acad Sci USA* 101:10149-10154; Owsianka, A. et al. 2005 *J Virol* 79:11095-11104; Tarr, A. W. et al. 2006 *Hepatology* 43:592-601; Brown, R. J. et al. 2007 *J Gen Virol* 88:458-469; Schofield, D. J. et al. 2005 *Hepatology* 42:1055-1062; Eren, R. et al. 2006 *J Viral* 80:2654-2664).

Recent data in chimpanzees has shown that an experimental Ig preparation made from anti-HCV-positive plasma (HCIGIV) prevents HCV infection when the preparation is mixed with a virus inoculum ex vivo before infusion (Yu, M. W. et al. 2004 *Proc Natl Acad Sci USA* 101:7705-7710). Unfortunately, the in vivo efficacy of HCIGIV in both chimpanzees and humans has been disappointing. For example, two clinical studies failed to show that anti-HCV Ig preparations could decrease HCV RNA levels or prevent recurrent infections after liver transplantation (Davis, G. L. et al. 2005 *Liver Transpl* 11:941-949, Schiano, T. D. et al. 2006 *Liver Transpl* 12:1381-1389). The need for more treatments for HCV infection is manifest.

SUMMARY OF THE INVENTION

It has been discovered that sufficient amounts of HCV epitope-specific neutralizing antibodies are present in patients suffering from chronic HCV infection but that the binding of these neutralizing antibodies is inhibited by the binding of competing or interfering antibodies at non-neutralization epitopes present on E2. That is, not only does anti-HCV-positive plasma, HCIGIV and biological samples obtained from patients that are chronically infected with HCV contain adequate amounts of HCV neutralizing antibodies but these preparations contain a second population of antibodies that diminish and/or inhibit altogether the ability of the neutralizing antibodies to interact with the virus. Accordingly, by enriching HCIGIV with antibodies that are directed specifically against neutralization epitopes and/or by providing compositions that contain molecules that disrupt the interaction of the population of inhibitory antibodies with E2, HCV therapy and prophylaxis can be improved.

HCV epitope-specific neutralizing antibodies were recovered from HCIGIV preparations using affinity chromatography and elution. Two epitopes within HCV E2 that are involved in neutralization of the virus were identified. Epitope I, which interacts with neutralizing antibodies, was mapped to amino acids 412-419 of E2, and epitope II, which mediates neutralizing antibody interference, was mapped to amino acids 434-446 of E2. The amino acid residues $L^{413}$ and $W^{420}$ were found to be required for recognition of EP I by EP I-specific HCV neutralizing antibodies and neutralizing antibody binding was enhanced when the $Q^{412}$ amino acid was replaced by an $H^{412}$ mutation. It was also found that replacement of the motif $^{415}NT^{416}$ with $Q^{415}$ resulted in an EP I domain that was not recognized by neutralization antibodies. Additionally, it was found that the amino acid motifs $TG^{436}$, $A^{439}$, and $^{441}LFY^{443}$ on the EP II domain are important for recognition of EP II by EP II-specific neutralization inhibitory antibodies. In fact, it appears that the $^{441}LFY^{443}$ domain creates a uniquely recognized epitope that is specifically recognized by the neutralization inhibitory antibodies, since an $AAA^{433}$ mutant was unable to bind to the neutralization inhibitory antibodies. An escape mutant containing the sequence $^{415}QNGS$ (SEQ ID NO: 1), which may be suitable for inclusion in an immunogenic composition or vaccine, was also identified.

Several plasma samples obtained from patients suffering from chronic HCV infection were analyzed and it was found that during chronic HCV infection, 44% of patients generate EP II-specific interfering antibodies, whereas 22% of patients generate EP I-specific neutralizing antibodies. It was also discovered that recovery of otherwise undetectable EP I-specific neutralization of HCV can be achieved by reducing the level of EP II-specific interfering antibodies in plasma obtained from a patient suffering from a chronic HCV infection. These findings indicate that HCV has evolved an elaborate mechanism to evade the host immune system, wherein antibodies directed to EP II interfere with the binding of neutralization antibodies at EP I but that this viral evasion strategy can be derailed by administration of pharmaceutical preparations that favor binding of neutralization antibodies, such as compositions that are devoid of EP II-specific antibodies and compositions that contain inhibitors of EP II-specific antibodies.

Accordingly, some embodiments include a composition comprising an isolated peptide consisting essentially of an Epitope II (EP II) sequence, wherein said peptide is a ligand for an antibody that inhibits neutralization of hepatitis C virus (HCV). Other embodiments include a composition, such as that described above, comprising an isolated peptide that is less than or equal to 20, 19, 18, 17, 16, 15, 14, 13, 12, 11, 10, 9, 8, 7, 6, or 5 amino acids in length, wherein said peptide comprises the sequence LFY or LLY. In still more embodiments, the compositions and/or peptides above are bound to a support or the gal epitope. Some of these compositions also include an Epitope I (EP I) sequence. Other aspects of the embodiments described herein include a composition comprising an isolated peptide consisting essentially of an Epitope II (EP II) sequence, wherein said peptide comprises a mutation that inhibits binding of an EP II-specific antibody. In some embodiments, this composition also includes a peptide having an Epitope I (EP I) sequence.

Still more embodiments, include an isolated antibody or fragment thereof, which binds specifically to an isolated peptide consisting essentially of an Epitope II (EP II) sequence. In some embodiments, this isolated antibody binds to an epitope that has the sequence LFY or LLY. More embodiments comprise an isolated anti-idiotype antibody or fragment thereof, which binds specifically to an EP II-specific antibody and this antibody or a fragment thereof can also have the gal epitope joined thereto. More embodiments concern a composition comprising an enriched HCIGIV preparation, which has been depleted for antibodies that bind to EP II.

Methods of identifying a ligand for an EP II-specific antibody are also embodiments. By some approaches these methods are practiced by providing an EP II-specific antibody or binding fragment thereof; providing a candidate ligand for said antibody or binding fragment thereof; providing a candidate ligand; and measuring the binding of said candidate ligand to said antibody or fragment thereof. By some methods, the candidate ligand is a peptide comprising an EP II sequence or mutant thereof and in some methods the candidate ligand is a peptide comprising the sequence of LFY or LLY. In some methods, the ligand is a DNA aptamer and in some methods the peptide comprises the sequence of LFY or LLY or the aptamer has a conformation that mimics an LFY or LLY sequence. By some approaches, the ligand is an anti-idiotype antibody or binding fragment thereof.

Methods of isolating an antibody or fragment thereof, which binds to a peptide comprising an EP II sequence or a mutant thereof are also embodiments. By some approaches these methods are practiced by providing a biological sample from an animal infected with hepatitis C virus (HCV), wherein said biological sample contains antibodies or a fragment thereof; contacting said biological sample with a peptide comprising an EP II domain, or a mutant thereof or a peptide comprising the sequence of LFY or LLY; and isolating an antibody or fragment thereof, which binds specifically to said peptides.

Methods of improving neutralization of HCV in a patient in need thereof are also embodiments. By some approaches these methods are practiced by identifying a patient in need of an inhibitor of an EP II-specific antibody; providing said patient a peptide that comprises the LFY or LLY sequence, a DNA aptamer that has a conformation that mimics an LFY or LLY sequence, or an anti-idiotype antibody or fragment thereof, that is specific for said EP II specific antibody; and measuring the reduction in HCV viral load or measuring a marker for HCV infection.

Methods of producing an immunogen and immunogens made thereby are also embodiments. An immunogen comprising portions of the E2 glycoprotein but not including or lacking an EP II sequence, which interacts with an inhibitory antibody, as described herein, are embodiments, for example.

BRIEF DESCRIPTION OF THE DRAWINGS

FIG. 1. Schematic representation of HCV polyprotein and biotin-linked peptides N (SEQ ID NO: 2), A (SEQ ID NO: 3), B (SEQ ID NO: 4), C (SEQ ID NO: 5), and D (SEQ ID NO: 6) used in this study. All peptides were synthesized based on the sequence of strain H77 (SEQ ID NO: 7). The numbers indicate the position of these peptides in HCV polyprotein, and single letters are used to represent amino acids.

FIG. 2. Presence of HCV E2 peptide-specific antibodies in HCIGIV. (A) Determination of HCIGIV antibody titer to peptide A. The x axis indicates the dilution of HCIGIV, and the y axis indicates absorbance at 450 nm in ELISA. Albumin (5%) and a control IGIV (5%) at 1:400 dilution in PBS were used as controls. (B) Spiking of HCIGIV into the control IGIV. The x axis indicates dilution of HCIGIV in the control ION. HCIGIV at 1:400 dilution alone was used as the positive control. Albumin (5%) and the control IGIV (5%) at 1:400 dilution were used as negative controls. The y axis indicates absorbance at 450 nm in ELISA.

FIG. 3. Determination of HCV epitope-specific antibodies in HCIGIV. The x axis indicates Ig eluates (AE, BE, CE, DE, or NE) collected after affinity binding and elution of HCIGIV by using a given peptide (peptide A, B, C, D, or N). HCIGIV at 1:400 dilution alone was used as the positive control. Albumin (5%) and the control IGIV (5%) at 1:400 dilution were used as negative controls. The y axis indicates absorbance at 450 nm in ELISA, representing specific binding of a given Ig eluate to each individual peptide.

FIG. 4. Summary of antibody binding and location of epitopes. (A) Antibody-binding activity in Ig eluates for individual peptides (Peptide A, SEQ ID NO: 3; Peptide B, SEQ ID NO: 4; Peptide C, SEQ ID NO: 5; Peptide D, SEQ ID NO: 6). The data from FIG. 5 are summarized. >, stronger than; =, equal to; –, no detectable peptide binding. (B) Identification of epitopes within HCV E2 protein. The sequences of the identified epitopes are underlined.

FIG. 5. Epitope mapping. (A) HCV epitope mapping by screening a random peptide phage-display library. Amino acid sequences of two phage clusters identified by screening a phage-display library (PhD-12) with AE as a source of antibodies are indicated (HCV E2, SEQ ID NO: 8; Cluster 1, SEQ ID NO: 9; Cluster 2, SEQ ID NO: 10). The key residues Of 441 LFY443 are indicated. The direction of the arrow indicates the arrangement of the residues in the peptide critical for antibody binding. The key residues for the epitope are numbered based on the amino acid sequence of strain H77. (B) Alignment of amino acid sequences of the E2 regions among various HCV genotypes based on the sequences provided by Owsianka, A. et al. 2005 J Virol 79:1 1095-1 1104; Barany, G. and Merrifield, R. B. The Peptides: Analysis, Synthesis and Biology Gross E, Meienhofer J., editors. New York: Academic; 1980. pp. 1-284 is shown. The positions of Epitopes I and II are indicated. A hyphen indicates an amino acid residue identical to that of the H77 sequence (SEQ ID NO: 45) (GenBank Accession No. AF009606 (H77), (SEQ ID NO: 11)), Ia, Ib, 2a, 2b, 3a, 4, 5, and 6 are shown.

FIG. 6. Identification of HCV epitope by mutation analysis. (A) Mutation of epitope II. Amino acid sequences for peptide B (SEQ ID NO: 4) and its mutation (B mutant, SEQ ID NO: 12) are presented. The mutation site is underlined. (B) Detection of antibody binding by ELISA. A total of 100 ng of biotin-conjugated peptide B and its mutant (B mutant) were added to streptavidin-coated 96-well plates in an ELISA. The x axis indicates antibodies that were used in this assay, HCIGIV at 1:800 dilution was used as the positive control, and albumin (5%) at 1:800 dilution was used as the negative control. 341C, a monoclonal antibody that recognizes the sequence NAPATV (SEQ ID NO: 28), was used at 1:200 dilution. The y axis indicates absorbance at 450 nm, representing specific binding of a given antibody to each individual peptide.

FIG. 7. HCV neutralization in cell culture. (A) HCV neutralization by Ig eluates. The x axis indicates Ig eluates that were used in this assay at 1:40 dilution. HCIGIV at 1:100 dilution was used as the positive control, and an IGIV (5%) at 1:100 dilution was used as the negative control. The y axis indicates infectivity (percentage of negative control). The asterisk indicates statistical significance (P<0.05). (B) Blocking neutralizing activity of DE by nonneutralizing Ig in AE. The x axis indicates Ig AE or DE alone at 1:40 dilution or a mixture of AE and DE (AE+DE) at 1:1 or 2:1 ratio. An IGIV (5%) at 1:100 dilution was used as the negative control. The y axis indicates infectivity (percentage of negative control). The asterisk indicates statistical significance (P<0.05).

FIG. 8. Presence of antibodies specific to peptides D and B, as assessed by peptide ELISA, in plasma from chimpanzees 1587 (A) and 1601 (B) vaccinated with recombinant E1E2 antigen. Data is presented as P/N ratios calculated as the OD 405 nm for post vaccine samples (post-vacc) divided by the OD 405 nm for pre vaccine samples (pre-vacs) from the same animal. A P/N ratio of greater than 2 is considered significant. Plasma samples were diluted 1:100 in a solution of 5% dried milk/PBS/0/05% Tween.

FIG. 9. Neutralization of a 2a genotype virus using plasma from E1E2 (genotype 1a) vaccinated chimpanzees before and after depletion of plasma using peptide B. Pre-vacc=pre vaccination plasma sample. Post-vacc=post vaccination plasma sample (used for ELISA analysis shown in FIG. 10) post-vacc+B=post vaccination sample treated with peptide B.

FIG. 10. Key residues within Epitope I for the binding of neutralizing antibody (Eluate I). (A) Peptidyl mimics of Epitope I were identified by screening random peptide phage display libraries. Epitope I is indicated (SEQ ID NO: 13), as well as phage sequences QPLVHVLPSWIE (SEQ ID NO: 14), HNAQPMTSWPIN (SEQ ID NO: 15), SYAS SHLNPRQLP (SEQ ID NO: 16), QLGTLVAGVHPR (SEQ ID NO: 17), SHHDNSWVTDDY (SEQ ID NO: 18), and ATWGPPDHAGPH (SEQ ID NO: 19). The key residues within both Epitope I and peptidyl mimics are indicated (underline) and represented schematically. The numbers indicate the position of these peptides in HCV polyprotein. An asterisk indicates the phage clone used in the panning experiments. (B) Formation of functional Epitope I by providing peptides displayed on individual phages in trans. X-axis indicates the type of input phages (5×105 pfu/reaction), and Y-axis indicates the numbers of phages recovered after panning by using Eluate I. (C) Effect of key residue mutations on antibody binding to Epitope I (SEQ ID NO: 13). Peptides containing Epitope I and its mutants at key residues are indicated. Peptides were added to streptavidin-coated 96-well plates (200 ng/well) in an ELISA. X-axis indicates individual peptides used, and Y-axis indicates absorbance at 450 nm in ELISA.

Eluate I and HCIGIV were used as the primary antibody in the ELISA at 1:100 and 1:2000 dilutions, respectively, in PBS.

FIG. 11. Characterization of Epitope II. (A) Alignment of amino acid sequences of the Epitope II regions among various HCV genotypes. Epitope II LNCNESLNTGWLAGLFYQHK (SEQ ID NO: 22), Ia (H77) NTGWLAGLFYQHK (SEQ ID NO: 23), Ib NTGFLAALFYVRNK (SEQ ID NO: 24), 2a NTGFIASLFYTHSK (SEQ ID NO: 25), and 2b QTGFLASLFYVNNK (SEQ ID NO: 26) are shown. (B) Detection of antibody binding of Epitope II by ELISA. Biotin-conjugated peptides containing Epitope II (genotype Ia), the N-terminal deletion mutant of Epitope II Ia isolated from patient H77, and Epitope II variants in other genotypes were added to streptavidin-coated 96-well plates (100 ng/well) in an ELISA. X-axis indicates peptides that were used in this assay. Eluate II, at 1:200, 1:400, 1:800, 1:1600 and 1:3200, was used as the primary antibody. Y-axis indicates absorbance at 450 nm obtained in ELISA, representing specific cross-reactivity of Eluate II derived from genotype Ia to each individual peptide in the indicated genotype.

FIG. 12. Determination of HCV epitope-specific antibodies in plasma of patients with chronic HCV infection. Biotin-conjugated peptides encompassing Epitope II, Epitope I or SW>AA (see FIG. 10C) were added to streptavidin-coated 96-well plates (200 ng/well). Plasma samples collected from patients with chronic HCV infection (H77 and Numbers 1-8) were diluted 1:800 and used as the primary antibody. HCIGIV lot A, Eluate I and Eluate II were used as controls. Y-axis indicates absorbance at 450 nm obtained in ELISA, representing specific binding of a given plasma to each individual peptide.

FIG. 13. Determination of HCV epitope-specific antibodies in HCIGIV. HCIGIV preparations (lots A, B, C, D, E, and F) were diluted 1:2000 and used as the primary antibodies in the ELISA, in which biotin-conjugated peptides encompassing Epitope II, Epitope I or SW>AA (see FIG. 10C) were added to streptavidin-coated 96-well plates (200 ng/well). Peptide SW>AA was used as a negative control, Y-axis indicates absorbance at 450 nm obtained in ELISA, representing specific binding of a given Ig preparation to each individual peptide. The ratios, antibody against Epitope II/antibody against Epitope I, are presented on the X-axis.

FIG. 14. Kinetics of the appearance of HCV epitope-specific antibodies during clinical course of the development of chronic HCV infection. Plasma samples collected from H77 before and after HCV infection, were diluted 1:100 except 5266 which was diluted 1:400, and used as the primary antibodies. Biotin-conjugated peptides encompassing Epitope II, Epitope I or SW>AA (see FIG. 10C) were added to streptavidin-coated 96-well plates (200 ng/well). HCIGIV lot A at 1:2000, Eluate I and Eluate II at 1:50 were used as controls for primary antibodies. SW>AA was used as a negative peptide control. Y-axis indicates absorbance at 450 nm obtained in ELISA, representing specific binding of a given plasma sample to each individual peptide.

FIG. 15. Recovery of neutralizing activity by diminishing interfering antibodies. (A) Amino acid sequences for Epitope II LNCNESLNTGWLAGLFYQHK (SEQ ID NO: 22) and its mutant LNCNESLNTGWLNAPATVK (SEQ ID NO: 27) are shown. The mutation site is underlined. (B) Detection of antibody binding by ELISA. Biotin-conjugated Epitope II and Epitope I were added to streptavidin-coated 96-well plates (200 ng/well). Plasma of H77 collected at day 5266, before and after absorption by using peptides containing Epitope II or its mutant, was diluted 1:800 and used as primary antibodies. HCIGIV lot A, at a 1:2000 dilution, was used as the positive control. Y-axis indicates absorbance at 450 nm, representing specific binding of a given plasma sample to each individual peptide. (C) Neutralization of HCV entry by plasma of H77 collected at day 5266 before and after removal of interfering antibody. X-axis indicates plasma sample that were used in this assay at 1:250 dilution. Y-axis indicates infectivity (% of negative control), Statistical significance (p<0.05) of difference in infectivity is indicated.

DETAILED DESCRIPTION

Incomplete neutralization of hepatitis C virus (HCV) even in the presence of a substantial level of neutralizing antibody represents a biological phenomenon that impacts greatly on antibody-mediated immune prophylaxis of virus infection and on successful vaccine design. The mechanism by which the virus escapes from antibody-mediated neutralization has remained elusive until now. As described herein, it has been discovered that patients infected with HCV produce sufficient amounts of HCV epitope-specific neutralizing antibodies but that the binding of these neutralizing antibodies is drastically reduced by a competing and/or interfering or inhibitory antibody, which is also produced in response to HCV infection.

Hepatitis C immune globulin intravenous (HCIGIV) has been fractionated from pools of anti-HCV-positive plasma from many donors. HCV epitope-specific neutralizing antibodies were efficiently recovered from HCIGIV preparations using affinity chromatography and elution. Two epitopes within HCV E2 that compete for binding of antibodies that are present in HCIGIV were identified. Epitope I (EP I), which interacts with antibodies that efficiently neutralize HCV, was mapped to amino acids 412-419 of E2. Epitope II (EP II), which interacts with antibodies that inhibit neutralization of HCV, was mapped to amino acids 434-446 of E2. Amino acid motifs that are involved in binding of neutralizing antibodies at EP I were identified. For example, $QL^{413}$ and $SW^{420}$, were found to be required for recognition of EP I by EP I-specific HCV neutralizing antibodies. It was also found that HCV neutralization can be improved when the amino acid $Q^{412}$ was replaced by an $H^{412}$ mutation and that replacement of the motif $415NT^{415}$ with $Q^{412}$ resulted in an EPI domain that was not recognized by neutralization antibodies.

Additionally, amino acid motifs that are involved in binding of inhibitory antibodies at EP II were identified. For example, $TG^{436}$, $A^{439}$, and $LFY^{443}$ were found to be required for recognition of EP II by EP II-specific neutralization inhibitory antibodies. In fact, it appears that the $^{441}LFY^{443}$ domain creates a uniquely recognized epitope that is specifically recognized by the neutralization inhibitory antibodies, since an $AAA^{433}$ mutant was unable to bind to the neutralization inhibitory antibodies. An escape mutant containing the sequence $^{415}QNGS$ (SEQ ID NO: 1), which may be suitable for inclusion in an immunogenic composition or vaccine, was also identified.

Several plasma samples obtained from patients suffering from chronic HCV infection were analyzed and it was found that during chronic HCV infection, 44% of patients generate EP II-specific interfering antibodies, whereas 22% of patients generate EP I-specific neutralizing antibodies. It was also found that recovery of otherwise undetectable EP I-specific neutralization of HCV can be achieved by reducing the level of EP II-specific interfering antibodies in plasma obtained from a patient suffering from a chronic HCV infection.

These data have allowed the development of several compositions and methods to induce and/or improve an immune response to HCV, as well as, kits and methods to enrich for neutralization epitope-specific antibodies or deplete competing and/or interfering antibodies from current HCIGIV preparations and kits and methods for identification of the presence and amount of neutralizing antibodies and competing and/or interfering antibodies in patients infected or at risk of becoming infected with HCV. The section below describes the discovery of the presence of competing HCV-specific antibodies in HCIGIV in greater detail.

Presence of Competing HCV-Specific Antibodies in HCIGIV

Previous studies indicated that the HCV E2 protein contained neutralization epitopes that were recognizable by a number of monoclonal antibodies (Farci, P. et al. 1996 *Proc Natl Acad Sci USA* 93:15394-15399; Triyatni, M. et al. 2002 *Virology* 298:124-132; Hsu, M. et al. 2003 *Proc Natl Acad Sci USA* 100:7271-7276; Logvinoff, C. et al. 2004 *Proc Natl Acad Sci USA* 101:10149-10154; Owsianka, A. et al. 2005 *J Virol* 79:11095-11104; Tarr, A. W. et al. 2006 *Hepatology* 43:592-601; Brown, R. J. et al. 2007 *J Gen Virol* 88:458-469; Schofield, D. J. et al. 2005 *Hepatology* 42:1055-1062; Eren, R. et al. 2006 *J Virol* 80:2654-2664). These epitopes formed a cluster within a short peptide between hypervariable regions I and II.

As described in Example 1, HCV epitope-specific neutralizing antibodies could be recovered from an HCIGIV using affinity chromatography. Two epitopes within a short segment of E2 were also precisely mapped: epitope I, at amino acids 412-419, and epitope II, at amino acids 434-446. It was found that epitope I, but not epitope II, was involved in virus neutralization. This finding was unexpected because the region encompassing amino acids 432-447 can be recognized by at least three monoclonal antibodies (2/69a, 7/16b, 11/20). These monoclonal antibodies have been shown to be involved in neutralization, as demonstrated in an HCV pseudoparticle assay (Hsu, M. et al. 2003 *Proc Natl Acad Sci USA* 100:7271-7276). The results from these experiments provided evidence that EP I and EP II are not presented independently and equally to the antibodies. Epitope I shares a sequence (amino acids 412-426) with an element that enhances antibody binding to epitope II (amino acids 434-446). However, once EP II is bound by an antibody, the site of EP I (amino acids 412-419) becomes masked. Epitope I could thus no longer be recognized by the specific antibodies (namely, $D_E$) directed against this epitope. Consistent with these findings, mixing non-neutralizing antibody ($A_E$) with neutralizing antibody ($D_E$) diminished the neutralizing activity of $D_E$.

It is contemplated that EP I requires discontinuous residues including QL and SW so as to form the conformational structure needed for the recognition of EP I-specific neutralizing antibodies. More precisely, $L^{413}$ and $W^{420}$ are the most important residues within Epitope I for the antibody binding. Interestingly, the same region is believed to be an epitope for at least three monoclonal antibodies, AP33, 3/11, and el37. Residues $L^{413}$, $I^{414}$, $T^{416}$, $G^{418}$, $W^{420}$, and $H_{421}$ were mapped for AP33 binding; $T^{416}$, $W^{420}$, $W^{529}$, and $G^{530}$, for 3/11; and $T^{416}$, $W^{420}$, $W^{529}$, $G^{530}$, and $D^{535}$, for el37 (See e.g., Tarr, A. W., Owsianka, A. M., Jayaraj, D., Brown, R. J., Hickling, T. P., Irving, W. L., Patel, A. H., & Ball, J. K. (2007) *J Gen Virol* 88:2991-3001; Perotti, M., Mancini, N., Diotti, R. A., Tarr, A. W., Ball, J. K., Owsianka, A., Adair, R., Patel, A. H., Clementi, M., & Burioni, R. (2008) *J Virol* 82:1047-1052; Tarr, A. W., Owsianka, A. M., Timms, J. M., McClure, C. P., Brown, R. J., Hickling, T. P., Pietschmann, T., Bartenschlager, R., Patel, A. H., & Ball, J. K. (2006) *Hepatology* 43:592-601; and Flint, M., Maidens, C., Loomis-Price, L. D., Shotton, C., Dubuisson, J., Monk, P., Higginbottom, A., Levy, S., & McKeating, J. A. (1999) *J Virol* 73:6235-6244).

In addition, a recent study has revealed a neutralization epitope, which contains at least three segments at residues 396-424, 436-447, and 523-540 (Law, M., Maruyama, T., Lewis, J., Giang, E., Tarr, A. W., Stamataki, Z., Gastaminza, P., Chisari, F. V., Jones, I. M., Fox, R. I., Ball, J. K., McKeating, J. A., Kneteman, N. M., & Burton, D. R. (2008) *Nat Med* 14: 25-27). Noticeably, the first segment overlaps with Epitope I, while the latter two are associated with CD81 binding, a possible point for virus entry. (See e.g., Triyatni, M., Vergalla, J., Davis, A. R., Hadlock, K. G., Foung, S. K. H., & Liang, T. J. (2002) *Virology* 298: 124-132; Perotti, M., Mancini, N., Diotti, R. A., Tarr, A, W., Ball, J. K., Owsianka, A., Adair, R., Patel, A. H., Clementi, M., & Burioni, R. (2008) *J Virol* 82:1047-1052; Owsianka, A., Clayton, R. F., Loomis-Price, L. D., McKeating, J. A., & Patel, A. H. (2001) *J Gen Virol* 82:1877-1883; Clayton, R. F., Owsianka, A., Aitken, J., Graham, S., Bhella, D., & Patel, A. H. (2002) *J Virol* 76:7672-7682; and Owsianka, A, M., Timms, J. M., Tarr, A. W., Brown, R. J., Hickling, T. P., Szwejk, A., Bienkowska-Szewczyk, K., Thomson, B. J., Patel, A. H., & Ball, J. K. (2006) *J Virol* 80:8695-8704). Accordingly, it is contemplated that the neutralizing antibodies and the competing/interfering and/or inhibitory antibodies recognize the same epitope although each appears to interact with a distinct set of residues.

It was also found that Epitone II-specific antibodies reacted differentially with Epitope II depending on the genotype. In view of the fact that Epitope II is involved in Epitope I-specific antibody interference, the data provided herein provide strong evidence that the binding of antibodies to Epitope II plays a significant role in tuning the capacity of the competing and/or inhibitory antibodies to interfere with the binding of neutralizing antibodies, thereby influencing in the clinical outcome of HCV infection.

Several human plasma samples were analyzed for the presence of neutralizing antibodies and the competing/interfering and/or inhibitory antibodies and it was discovered that during chronic HCV infection, 44% of patients generated EP II-specific interfering antibodies, whereas 22% of patients generated EP I-specific neutralizing antibodies. Importantly, when neutralizing antibodies were found, they occurred concurrently with elevated levels of interfering antibodies. By taking advantage of a well-established case (H77) of chronic HCV infection, the kinetics of these two antibodies was analyzed. It was found that Epitope I neutralizing antibodies were undetectable during the early phase of HCV infection, and that when they became detectable during the chronic phase of HCV infection, they appeared concurrently with interfering antibody against Epitope II. By contrast, interfering antibodies specific for EP II appeared at the early stage of HCV infection and co-existed with the neutralizing antibodies during chronic infection.

These observations provide strong evidence of a mechanism of HCV persistence: on one hand, if neutralizing antibody is present early during the infection, neutralizing antibody may be sufficiently potent for controlling the infection, resulting in a resolution of the infection; on the other hand, if a high level of interfering antibody is present early in the absence neutralizing antibody, the infection can be established, leading to chronicity. In addition, when interfering antibody is present early, along with neutralizing antibody, the clinical outcome depends on the ratio of interfering and neutralizing antibodies. Accordingly, virus may escape from a neutralizing antibody response without introduction of new escape mutations within the neutralizing epitope. This is consistent with the observation that EP I is a highly conserved immune determinant among different HCV genotypes, while EP II is not.

Indeed, it was discovered that the competing and/or interfering antibodies that inhibit binding of the HCV neutralizing antibodies can be specifically depleted from plasma obtained from a subject infected with HCV and recovery of otherwise undetectable Epitope I-speicific neutralization of HCV can be achieved by reducing the level of Epitope II-specific interfering antibodies in a plasma obtained from a chronically infected patient. These data provide evidence that broadly neutralizing, Epitope-I specific antibodies against different HCV genotypes can be made accessible in vivo by freeing them from constraints imposed by Epitope II-specific antibodies.

This approach paves the way for the development of new HCV therapies. For example, experimental HCV-specific Ig preparations are currently made from the pooled plasma of anti-HCV-positive donors. It is thus not surprising to detect both neutralizing and non-neutralizing antibodies, i.e., those directed against Epitopes I and II, respectively, in these preparations. However, it is now known that the ratios of interfering/neutralizing antibodies in these Ig preparations represent the weighted average of those in the plasma of chronically HCV infected patients. That is, simply increasing the frequency of administration or elevating the dose of current HCIGIV products would not be adequate to achieve complete inactivation of circulating infectious virus, especially in patients with high levels of interfering antibodies. Reversing the ratio, by depleting interfering antibodies while enriching neutralizing antibodies, provides a way to generate a more effective HCV-specific Ig product for passive immune-prophylaxis of HCV infection.

Accordingly, it appears that a preexisting network of both neutralization and non-neutralization epitopes affects the dynamic of antibody binding, thus influencing the course of HCV infection. Furthermore, the in vivo efficacy of enriched HCIGIV preparations appears to depend on the binding affinity of non-neutralizing antibodies in the recipient and their capacity to interfere with the function of the selected neutralizing antibodies. Depletion of interfering antibodies from HCIGIV preparations enhances HCV neutralization and the levels of interfering antibodies in patients infected with HCV should be evaluated. Accordingly, some embodiments described herein concern kits and methods to enrich for neutralization epitope-specific antibodies or deplete competing and/or interfering antibodies from current HCIGIV preparations and, kits and methods for identification of the presence and amount of neutralizing antibodies and competing and/or interfering antibodies in patients infected with HCV. The section below describes in greater detail some of the peptide and nucleic acid embodiments that can be used in the therapeutic approaches described herein.

Peptides and Nucleic Acids

Some aspects of the invention include compositions that consist of, consist essentially of, or comprise an isolated or recombinant E2 polypeptide or fragment thereof that consists of, consists essentially of, or comprises an EP I and/or EP II peptides and/or mutants thereof. Analogs and muteins of these E2 polypeptides are also embodiments. Other aspects of the invention include compositions that consist of, consist essentially of, or comprise nucleic acids that encode an isolated or recombinant E2 polypeptide or fragment thereof that consists of, consists essentially of, or comprises an EP I and/or EP II peptides and/or mutants thereof. Analogs and muteins of these nucleic acids are also embodiments.

Preferably, the aforementioned compositions comprise one or more peptides that comprise, consist or consist essentially of an EP I sequence (QLINTNGS (SEQ. ID. No. 29)) and/or an EP II sequence (NTGWLAGLFYQHK (SEQ. ID. No. 30)); however, as shown in FIG. 5, variations of these sequences can also be provided. For example, some compositions comprise a peptide that comprises, consists, or consists essentially of a 1a EP II sequence (DTGWVA-GLFYYHR (SEQ. ID. No. 31)); a 1b EP 1 sequence QLVNTNGS (SEQ. ID. No. 32); a 1b EP II sequence (NTG-FLAALFYVRN (SEQ. ID. No. 33)); a 2a EP II sequence (NTGFIASLFYTHS (SEQ. ID. No. 34)); a 2b EP I sequence (SLINTNGS (SEQ. ID. No. 35)); a 2b EP II sequence NTG-FLAGLFYYHK. (SEQ. ID. No. 36); a 3a EP I sequence (ELINTNGS (SEQ. ID. No. 37)); a 3a EP II sequence NTG-FLAGLFYYHK (SEQ. ID. No. 38); a 4 EP I sequence (QLINSNGS (SEQ. ID. No. 39)); a 4 EP II sequence NTG-FLAGLFYHYS (SEQ. ID. No. 40); a 5 EPI sequence (QVINTNGS (SEQ. ID. No. 41)); a 5 EP II sequence QTG-FIAGLLYFNK (SEQ. ID. No. 42); or a 6 EP II sequence QTGFIASLFYFNK (SEQ. ID. No. 43), or any combination or mixture thereof.

Furthermore, E2 peptide sequences flanking EP I and/or EP II, as identified in FIG. 5 can also be included in any one or more of the embodiments described herein. It should be understood that sequences from organisms other than HCV can also be provided or artificial sequences can be provided. That is, the peptides that comprise, consist or consist essentially of a EP I and/or EP II sequence or mutants thereof used in the embodiments described herein can be of variable length (e.g., the peptides that comprise, consist, or consist essentially of any one of SEQ. ID. Nos. 29, 30, 31, 32, 33, 34, 35, 36, 37, 38, 39, 40, 41, 42, or 43 or a mutant thereof may be at least three amino acids in length, e.g., containing the $LFY^{443}$ domain of EP II, and may be at least, equal to, less than, or greater than 5, 6, 7, 8, 9, 10, 11, 12, 13, 14, 15, 16, 17, 18, 19, 20, 21, 22, 23, 24, 25, 26, 27, 28, 30, 40, or 50 amino acids in length. Some embodiments also include a nucleic acid encoding any one or more of the aforementioned peptide sequences, for example, an optimized nucleic acid for expression in humans (e.g., a codon optimized nucleic acid encoding any one or more of the peptides of SEQ ID Nos 29, 30, 31, 32, 33, 34, 35, 36, 37, 38, 39, 40, 41, 42, or 43).

It should also be noted that some of the aforementioned sequences can be mutated and the mutant sequences retain the ability to bind the respective antibodies and/or have improved or reduced antibody binding capacity. In some embodiments, the compositions consist of, consist essentially of, or comprise an isolated or recombinant E2 polypeptide or fragment thereof that consists of, consists essentially of, or comprises an EP I domain having a sequence that includes $QL^{413}$ or $SW^{420}$. In other embodiments, the compositions consist of, consist essentially of, or comprise a nucleic acid encoding an isolated or recombinant E2 polypeptide or fragment thereof that consists of, consists essentially of, or comprises an EP I domain having a sequence that includes $QL^{413}$ or $SW^{420}$. More embodiments include compositions that consist of, consist essentially of, or comprise an isolated or recombinant E2 polypeptide or fragment thereof that consists of, consists essentially of, or comprises an EP I domain, wherein the sequence $QL^{413}$ is replaced by the sequence $HL^{413}$. Still more embodiments include compositions that consist of consist essentially of, or comprise a nucleic acid encoding an isolated or recombinant E2 polypeptide or fragment thereof that consists of, consists essentially of, or comprises an EP I domain, wherein the sequence $QL^{413}$ is replaced by the sequence $HL^{413}$. Some embodiments consist of, consist essentially of, or comprise an isolated or recombinant E2 polypeptide or fragment thereof that consists of, consists essentially of, or comprises an EP I domain having the sequence $^{415}$QNGS (SEQ ID NO: 1) or a nucleic acid encoding the same, which may be suitable for inclusion in an immunogenic composition or vaccine.

In some embodiments, the compositions consist of, consist essentially of, or comprise an isolated or recombinant E2 polypeptide or fragment thereof that consists of, consists essentially of, or comprises an EP II domain having a sequence that includes the sequence $TG^{436}$, $A^{439}$, and $LFY^{443}$. In other embodiments, the compositions consist of, consist essentially of, or comprise a nucleic acid encoding an isolated or recombinant E2 polypeptide or fragment thereof that consists of, consists essentially of, or comprises an EP II domain having a sequence that includes the sequence $TG^{436}$, $A^{439}$, or $LFY^{443}$. Mutants of the aforementioned peptides and nucleic acids are also embodiments, for example the $AAA^{443}$ mutant is preferred because it is unable to bind the EP II-specific inhibitory antibodies. Accordingly, some embodiments include an isolated peptide that consists of, consists essentially of, or comprises a peptide that consists of, consists essentially of, or comprises an $LFY^{443}$ or $AAA^{443}$ domain or a nucleic acid encoding said peptides. As mentioned before, the peptide comprising, consisting, or consisting essentially of one or more of the aforementioned EP II sequences may be at least, equal to, less than, or greater than 5, 6, 7, 8, 9, 10, 11, 12, 13, 14, 15, 16, 17, 18, 19, 20, 21, 22, 23, 24, 25, 26, 27, 28, 30, 40, or 50 amino acids in length and nucleic acids encoding these peptides are also embodiments.

The term "E2 polypeptide" is intended to refer to a molecule derived from an HCV E2 region. The mature E2 region of HCV-la begins at approximately amino acid 384, numbered relative to the full-length HCV-1 polyprotein. A signal peptide begins at approximately amino acid 364 of the polyprotein. The corresponding region for other HCV genotypes and subtypes are known and readily determined by comparison to the HCV-1a polyprotein. For ease of discussion then, numbering herein is with reference to the HCV-1a genome, but it is to be understood that an "E2 polypeptide" also encompasses E2 polypeptides from any of the various HCV genotypes, such as HCV-1, HCV-2, HCV-3, HCV-4, HCV-5 and HCV-6 and subtypes thereof, such as HCV-1a, HCV-2a, HCV-3a, HCV-4a, HCV-5a and HCV-6a.

Thus, in some contexts, the term "E2 polypeptide" is meant to refer to either a precursor E2 protein, including the signal sequence, or a mature E2 polypeptide, which lacks this sequence, or even an E2 polypeptide with a heterologous signal sequence. The E2 polypeptide, in HCV, includes a C-terminal membrane anchor sequence which occurs at approximately amino acid position 718 and may extend as far as approximately amino acid residue 746, numbered relative to the HCV-1a polyprotein. An E2 polypeptide may or may not include the C-terminal anchor sequence or portions thereof. Additionally, the E2 polypeptide may or may not be glycosylated. Moreover, an E2 polypeptide may include all or a portion of the p7 region which occurs immediately adjacent to the C-terminus of E2. The p7 region of the HCV-1a polyprotein is found at positions 747-809, numbered relative to the full-length HCV-1 polyprotein. Additionally, it is known that multiple isotypes of HCV E2 exist. Accordingly, in some contexts, the term "E2" encompasses any E2 isotype including, without limitation, sequences that have deletions of 1-20 or more of the amino acids from the N-terminus of the E2, such as, e.g., deletions of 1, 2, 3, 4, 5 . . . 10 . . . 15, 16, 17, 18, 19 . . . etc. amino acids. Such E2 variants include those beginning at amino acid 387, amino acid 402, amino acid 403, etc.

Furthermore, an "E2 polypeptide" may not be limited to a polypeptide having the exact sequence depicted in the HCV databases. Indeed, the HCV genome is in a state of constant flux in vivo and contains several variable domains which exhibit relatively high degrees of variability between isolates. A number of conserved and variable regions are known between these strains and, in general, the amino acid sequences of epitopes derived from these regions will have a high degree of sequence homology, e.g., amino acid sequence homology of more than 30%, preferably more than 40%, more than 60%, and even more than 80-90%, or at least 95% homology or identity, when the two sequences are aligned.

"Homology" refers to the percent identity between two polynucleotide or two polypeptide moieties. Two DNA, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively, Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National Biomedical Research Foundation, Washington, D.C., which adapts the local homology algorithm of Smith and Waterman 1981 *Advances in Appl Math* 2:482-489, for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penally of six nucleotide positions.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al. *Molecular Cloning: A Laboratory Manual* (2d ed., Cold Spring Harbor Laboratory Press, Cold Spring Harbor, N.Y. (1989).

It is readily apparent that the term "E2 polypeptides" encompasses E2 polypeptides from any of the various HCV strains and isolates including isolates having any of the 6 genotypes of HCV described in Simmonds et al. 2005 *Hepatology* 42:962-973 (e.g., strains 1, 2, 3, 4 etc.), as well as newly identified isolates, and subtypes of these isolates, such as HCV1a, HCV1b etc. Thus, for example, the term "E2" polypeptide refers to native E2 sequences from any of the various HCV genotypes, unless specifically identified, as well as analogs, muteins and immunogenic fragments, as defined further below. The complete genotypes of many of these strains are known. See, e.g., Simmonds et al. 2005 *Hepatology* 42:962-973.

Additionally, the term "E2 polypeptide" may encompass proteins, which include modifications to the native sequence, such as internal deletions, additions and substitutions (generally conservative in nature), such as proteins substantially homologous to the parent sequence. These modifications may be deliberate, as through site-directed mutagenesis, or may be accidental, such as through naturally occurring mutational events. All of these modifications are encompassed in certain embodiments so long as the modified E2 polypeptides function for their intended purpose. Thus, for example, if the E2 polypeptides are to be used in immunogenic compositions, the modifications must be such that immunological activity (i.e., the ability to elicit a humoral or cellular immune response to the polypeptide) is not lost.

The term "isolated" is oftentimes used to refer to a polypeptide that is separate and discrete from the whole organism with which the molecule is found in nature or is present in the substantial absence of other biological macromolecules of the same type. The term "isolated" with respect to a polynucleotide can refer to a nucleic acid molecule devoid, in whole or part, of sequences normally associated with it in nature; or a sequence, as it exists in nature, but having heterologous sequences in association therewith; or a molecule disassociated from the chromosome.

Similarly, the term "recombinant" can be used to describe a nucleic acid molecule means a polynucleotide of genomic, RNA, DNA, cDNA, viral, semisynthetic, or synthetic origin which, by virtue of its origin or manipulation is not associated with all or a portion of the polynucleotide with which it is associated in nature. The term "recombinant" as used with respect to a protein or polypeptide can refer to a polypeptide produced by expression of a recombinant polynucleotide. In general, the gene of interest is cloned and then expressed in transformed organisms, as described further below. The host organism expresses the foreign gene to produce the protein under expression conditions.

The terms "analog" and "mutein" can refer to biologically active derivatives of the reference molecule, such as E2, or fragments of such derivatives, that retain desired activity, such as immunoreactivity in assays described herein. In general, the term "analog" refers to compounds having a native polypeptide sequence and structure with one or more amino acid additions, substitutions (generally conservative in nature) and/or deletions, relative to the native molecule, so long as the modifications do not destroy immunogenic activity. The term "mutein" refers to polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. Preferably, the analog or mutein has at least the same immunoreactivity as the native molecule. Methods for making polypeptide analogs and muteins are known in the art and are described further below.

Particularly preferred analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine, threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest, such as an E2 polypeptide or mutant thereof, as described herein, may include up to about 5-10 conservative or non-conservative amino acid substitutions, or even up to about 15-25 or 50 conservative or non-conservative amino acid substitutions, or any integer between 5-50, so long as the desired function of the molecule remains intact. One of skill in the art can readily determine regions of the molecule of interest that can tolerate change by reference to Hopp/Woods and Kyte-Doolittle plots. In some contexts, the term analog and/or mutein are used to refer to nucleic acids encoding the polypeptide analogs and/or muteins described above.

In some contexts, the term "fragment" is intended to refer to a polypeptide consisting of only a part of the intact full-length polypeptide sequence and structure. The fragment can include a C-terminal deletion an N-terminal deletion, and/or an internal deletion of the native polypeptide. An "immunogenic fragment" of a particular HCV protein will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, that define an epitope, or any integer between 5 amino acids and the full-length sequence, provided that the fragment in question retains the ability to elicit an immunological response as defined herein.

The term "epitope" as used herein can refer to a sequence of at least about 3 to 5, preferably about 5 to 10 or 15, and not more than about 500 amino acids (or any integer therebetween), which define a sequence that by itself or as part of a larger sequence, elicits an immunological response in the subject to which it is administered. Often, an epitope will bind to an antibody generated in response to such sequence. There is no critical upper limit to the length of the fragment, which may comprise nearly the full-length of the protein sequence, or even a fusion protein comprising two or more epitopes from the HCV polyprotein. An epitope for use in the subject invention is not limited to a polypeptide having the exact sequence of the portion of the parent protein from which it is derived. Indeed, viral genomes are in a state of constant flux and contain several variable domains which exhibit relatively high degrees of variability between isolates. Thus the term "epitope" encompasses sequences identical to the native sequence, as well as modifications to the native sequence, such as deletions, additions and substitutions (generally conservative in nature).

Regions of a given polypeptide that include a neutralization epitope can be identified using any number of epitope mapping techniques, well known in the art. See, e.g., *Epitope Mapping Protocols in Methods in Molecular Biology*, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Similarly, conformational epitopes are readily identified by determining spatial conformation of amino acids such as by, e.g., x-ray crystallography and 2-dimensional nuclear magnetic resonance. See, e,g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al. 1981 *Proc Natl Acad Sci USA* 78:3824-3828 for determining antigenicity profiles, and the Kyte-Doolittle technique, Kyte et al. 1982 *J Mol Biol* 157:105-132 for hydropathy plots.

Also contemplated for use in the compositions and methods described herein are complexes of E1 and the aforementioned E2 polypeptides or fragments thereof. The E1 and E2 polypeptides in such complexes can be associated either through non-covalent or covalent interactions. Such complexes may also include all or a portion of the p7 region, which occurs immediately adjacent to the C-terminus of E2. The E1 and E2 polypeptides or fragments thereof and complexes of these molecules may also be present as asialoglycoproteins. Such asialoglycoproteins are produced by methods known in the art, such as by using cells in which terminal glycosylation is blocked. When these proteins are expressed in such cells and isolated by GNA lectin affinity chromatography, the E1 and E2 proteins aggregate spontaneously.

Moreover, the E1E2 complexes may comprise a heterogeneous mixture of molecules, due to clipping and proteolytic cleavage, as described above. Thus, a composition including E1E2 complexes may include multiple species of E1E2, such as E1E2 terminating at amino acid 746 ($E1E2_{745}$), E1E2 terminating at amino acid 809 ($E1E2_{809}$), or any of the other various E1 and E2 molecules, such as E2 molecules with N-terminal truncations of from 1-20 amino acids, such as E2 species beginning at amino acid 387, amino acid 402, amino acid 403, etc.

Polynucleotides encoding HCV E2 polypeptides, to be used for expressing E2 polypeptides for use either alone or in complexes, can be made using standard techniques of molecular biology. For example, polynucleotide sequences coding for the above-described molecules can be obtained using recombinant methods, such as by screening cDNA and genomic libraries from cells expressing the gene, or by deriving the gene from a vector known to include the same. Furthermore, the desired gene can be isolated directly from viral nucleic acid molecules, using techniques described in the art. The gene of interest can also be produced synthetically, rather than cloned. The molecules can be designed with appropriate codons for the particular sequence. The complete sequence is then assembled from overlapping oligonucleotides prepared by standard methods and assembled into a complete coding sequence.

Thus, particular nucleotide sequences can be obtained from vectors harboring the desired sequences or synthesized completely or in part using various oligonucleotide synthesis techniques known in the art, such as site-directed mutagenesis and polymerase chain reaction (PCR) techniques where appropriate. In particular, one method of obtaining nucleotide sequences encoding the desired sequences is by annealing complementary sets of overlapping synthetic oligonucleotides produced in a conventional, automated polynucleotide synthesizer, followed by ligation with an appropriate DNA ligase and amplification of the ligated nucleotide sequence via PCR. Additionally, oligonucleotide directed synthesis, oligonucleotide directed mutagenesis of preexisting nucleotide regions, and enzymatic filling-in of gapped oligonucleotides using T4 DNA polymerase can be used to provide molecules having altered or enhanced antigen-binding capabilities and immunogenicity.

Once coding sequences have been prepared or isolated, such sequences can be cloned into any suitable vector or replicon. Numerous cloning vectors are known to those of skill in the art, and the selection of an appropriate cloning vector is a matter of choice. Suitable vectors include, but are not limited to, plasmids, phages, transposons, cosmids, chromosomes or viruses which are capable of replication when associated with the proper control elements.

The coding sequence is then placed under the control of suitable control elements, depending on the system to be used for expression. Thus, the coding sequence can be placed under the control of a promoter, ribosome binding site (for bacterial expression) and, optionally, an operator, so that the DNA sequence of interest is transcribed into RNA by a suitable transformant. The coding sequence may or may not contain a signal peptide or leader sequence which can later be removed by the host in post-translational processing.

In addition to control sequences, it may be desirable to add regulatory sequences which allow for regulation of the expression of the sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector. For example, enhancer elements may be used herein to increase expression levels of the constructs. Examples include the SV40 early gene enhancer, the enhancer/promoter derived from the long terminal repeat (LTR) of the Rous Sarcoma Virus and elements derived from human CMV, such as elements included in the CMV intron A sequence. The expression cassette may further include an origin of replication for autonomous replication in a suitable host cell, one or more selectable markers, one or more restriction sites, a potential for high copy number and a strong promoter.

An expression vector is constructed so that the particular coding sequence is located in the vector with the appropriate regulatory sequences, the positioning and orientation of the coding sequence with respect to the control sequences being such that the coding sequence is transcribed under the control" of the control sequences (i.e., RNA polymerase which binds to the DNA molecule at the control sequences transcribes the coding sequence). Modification of the sequences encoding the molecule of interest may be desirable to achieve this end. For example, in some cases it may be necessary to modify the sequence so that it can be attached to the control sequences in the appropriate orientation; i.e., to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site.

As explained above, it may also be desirable to produce mutants or analogs of the polypeptide of interest. Mutants or analogs of HCV polypeptides for use in the subject compositions may be prepared by the deletion of a portion of the sequence encoding the polypeptide of interest, by insertion of a sequence, and/or by substitution of one or more nucleotides within the sequence. Techniques for modifying nucleotide sequences, such as site-directed mutagenesis, alanine scan and the like, are well known to those skilled in the art.

On the basis of the evidence provided herein, mutation of amino acids $LFY^{443}$ of epitope II to produce a polypeptide comprising the amino acid sequence of epitope I having enhanced neutralization can be carried out by a systematic approach comprising replacement of each of the amino acids $LFY^{443}$. A triply-substituted peptide or nucleic acid encoding the same can then be tested for enhanced neutralization and further amino acid substitutions can be made in the remainder of epitope II by the systematic, sequential method described herein. Thus, any combination of substitutions can be tested for enhanced neutralization in a systematic manner.

Additionally, deletion of amino acids $LFY^{443}$ in epitope II to produce a polypeptide comprising the amino acid sequence of epitope I having enhanced neutralization can be carried out by a systematic approach comprising omission of each of the amino acids $LFY^{443}$ in epitope II. A triply-deleted skein can then be tested for enhanced neutralization and further amino acid deletions can be made in the remainder of epitope II by the systematic, sequential method described herein. Thus, any combination of deletions can be tested for enhanced neutralization in a systematic manner.

Furthermore, insertion of amino acids between amino acids $LFY^{443}$ in epitope II to produce a polypeptide comprising the amino acid sequence of epitope I having enhanced neutralization can be carried out by a systematic approach comprising addition of amino acids between each of the amino acids $LFY^{443}$ in epitope II. A triply-disrupted skein can then be tested for enhanced neutralization and further amino acid additions can be made between amino acids in the remainder of epitope II by the systematic, sequential method described herein. Thus, any combination of insertions can be tested for enhanced neutralization in a systematic manner.

The molecules can be expressed in a wide variety of systems, including insect, mammalian, bacterial, viral and yeast expression systems, all well known in the art. For example, insect cell expression systems, such as baculovirus systems, are available. Materials and methods for baculovirus/insect cell expression systems are commercially available in kit form from, inter alia, Invitrogen, San Diego Calif. ("MaxBac" kit). Yeast expression systems are also known in the art and described in, e.g., *Yeast Genetic Engineering* (Barr et al., eds., 1989) Butterworths, London.

A number of appropriate host cells for use with the above systems are also known. For example, mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human embryonic kidney cells, human hepatocellular carcinoma cells (e.g., Hep G2), Madin-Darby bovine kidney ("MDBK") cells, as well as others. Similarly, bacterial hosts such as *E. coil*., will find use with the present expression constructs. Yeast hosts useful in the present invention include inter alia, *Saccharomyces cerevisiae* and *Pichia pastoris*. Insect cells for use with baculovirus expression vectors include, inter alia, *Spodoptera frugiperda* and *Trichoplusia ni*. The aforementioned compositions can be used in several methods to diagnose the presence or absence of HCV neutralizing antibodies and/or interfering/inhibitory antibodies in mammals, as well as, therapies designed to improve neutralization of HCV in infected mammals, as described in the following sections.

Enhanced Neutralizing Antibody Preparations

In the last decade, intravenous immunoglobulins (IVIG) have become an important treatment regime for bacterial and viral infections and of primary and secondary immunodeficiency states. WIG is prepared from the pooled plasmas of large numbers of donors, and tend to have a broad representation of antibodies. Pooled polyvalent human globulins usually contain antibodies for many pathogens such as hepatitis B virus (HBV). Antibody concentrations vary from lot-to-lot and between manufacturers. IVIG therapy has been reported to be beneficial for many diseases. Passive immunization against infections has been particularly successful with immune globulins specific for hepatitis B. Passive immunization depends on the presence of high and consistent titers of antibodies to the respective pathogens in each preparation. Thus, while intravenous passive immunization has been successful for certain diseases, it has had inconsistent performance against many other types of infections. The term "immune globulin," is used herein to describe polyclonal hyperimmune serum raised in subjects (e.g., humans infected with HCV). The immune globulin contains antibodies that neutralize infectious HCV and its in vivo effects.

It is contemplated that peptides that consist, consist essentially of, or comprise the neutralization epitope I (EP I) and epitope II can be exploited to enrich HCIGIV preparations for HCV neutralizing antibodies. For example, peptides having the EP I domain (e.g., a peptide that is at least, equal to, less than, or greater than 5, 6, 7, 8, 9, 10, 11, 12, 13, 14, 15, 16, 17, 18, 19, 20, 21, 22, 23, 24, 25, 26, 27, 28, 30, 40, or 50 amino acids in length such as SEQ. ID. NOs, 29, 32, 35, 37, 39 or 41) can be immobilized on a support (e.g., a macromoleclular structure or scaffold, such as a bead, gel, or plastic) and the immobilized peptides can be used for affinity chromatographic isolation of HCV neutralizing antibodies from HCIGIV preparations in the presence of EP II peptides or a peptide containing the $LFY^{443}$ or $LLY^{443}$ sequence (e.g., a peptide that is at least, equal to, less than, or greater than 5, 6, 7, 8, 9, 10, 11, 12, 13, 14, 15, 16, 17, 18, 19, 20, 21, 22, 23, 24, 25, 26, 27, 28, 30, 40, or 50 amino acids in length containing the $LFY^{443}$ or $LLY^{443}$ sequence, such as SEQ. ID. NOs. 30, 31, 33, 34, 36, 38, 41, 42 or 43). Nucleic acids encoding these peptides are also embodiments. These isolated antibodies can then be formulated into pharmaceuticals and provided to subjects that have been identified as needing an antibody that neutralizes HCV. Optionally, the presence of HCV viral lode can be measured before, during, and after said subjects are provided the aforementioned neutralizing antibodies. Conventional approaches can be used to identify subjects in need of the neutralizing antibodies, such as commercially available diagnostic tests and clinical evaluation.

Alternatively, by some approaches, a method of making an enriched HCIGIV preparation is provided wherein an HCIGIV preparation is obtained, said preparation is contacted with a peptide comprising, consisting of or consisting essentially of EP II or a fragment or mutant thereof (e.g., SEQ. ID. Nos. 30, 31, 33, 34, 36, 38, 41, 42, or 43), or a composition comprising a peptide that consists of, consists essentially of, or comprises the sequence of $LFY^{443}$ or $LLY^{443}$ sequence (e.g., a peptide that is at least, equal to, less than, or greater than 5, 6, 7, 8, 9, 10, 11, 12, 13, 14, 15, 16, 17, 18, 19, 20, 21, 22, 23, 24, 25, 26, 27, 28, 30, 40, or 50 amino acids in length containing the $LFY^{443}$ or $LLY^{443}$ sequence, such as SEQ. ID. Nos. 30, 31, 33, 34, 36, 38, 41, 42, or 43). Optionally, the aforementioned peptides are bound to a support, which can be plastic, a bead, resin, or gel. After contact of the peptide with the HCIGIV preparation, the unbound material can then be formulated into a pharmaceutical suitable for administration to a human that is infected with HCV. Methods of using the enriched HCIGIV preparation (i.e., an HCIGIV preparation that has a purified neutralizing antibody population in that it has been had antibodies that inhibit the binding of the neutralizing antibodies separated away from the preparation) are also contemplated.

By some approaches, an HCIGIV preparation that has been depleted of EP II-specific antibodies (e.g., antibodies that inhibit binding of antibodies to EP I), that is an enriched HCIGIV preparation can be provided to a patient suffering from HCV infection so as to improve the neutralization of the virus. Accordingly, in some embodiments, a patient infected with HCV is identified as a subject in need of an enriched HCIGIV preparation and said subject is provided an enriched HCIGIV preparation prepared as described herein. Optionally, the patient is identified as a subject in need of an enriched HCIGIV preparation by diagnostic evaluation of the amount of EP II-specific antibodies present in their plasma and/or the ratio of EP II-specific antibodies to EP I specific antibodies. Thus, some embodiments include an enriched HCIGIV preparation or an isolated enriched human plasma, which contains a ratio of EP I specific antibodies:EP II specific antibodies that is greater than 1:1 (e.g., greater than or equal to 1.1:1; 1.2:1; 1.3:1; 1.4:1; 1.5:1; 1.6:1; 1.7:1; 1.7:1; 1.8:1; 1.9:1; 2:1; 2.5:1; 3:1; 4:1; or 5:1 EP I specific antibodies:EP II specific antibodies) and methods of making such preparations and methods of using said preparations to improve HCV neutralization in a human.

Thus, these purified neutralizing immune globulins are useful for the prevention and treatment of diseases and conditions caused by HCV. In particular, methods for preparing IgG that has a reduced amount of or is essentially free from interfering antibodies specific for epitope II of HCV are provided. Methods of preparing IgG that has a reduced amount of or is essentially free of interfering antibodies specific for epitope II of HCV are also embodiments The immune globulins in these embodiments can be purified from a human or chimpanzee source. Chimpanzees, therefore, represent a non-human animal available for testing for infectious HCV. In certain cases, the source is a human or animal source that has been previously exposed to HCV. These sources can be exposed on purpose by administering the antigen to the subject (e.g., by injection). Alternatively, the source can be a subject that has been or is exposed to the antigen such as HCV. Typically the source of the immune globulins is subjected to one or more purification methods, such as Cohn cold-ethanol fractionation, or standard chromatography methods, such as sizing column chromatography or ion exchange. Preferably, the purified sample contains all or predominantly IgG, but mixtures containing, e.g., IgG, IgA, and IgM, can also be used.

As noted, immunoaffinity purification/isolation is the preferred purification approach for removing interfering antibodies against epitope II of HCV. Immunoaffinity purification/isolation is a separation/isolation technique based on the affinity of antibody for specific antigen(s); antibody that binds to specific antigen(s) is separated from antibody that does not bind (under the conditions used). Immunoaffinity purification/isolation can dramatically reduce the nonneutralizing effect of immune globulin by elimination of interfering antibodies when the immune globulin is used therapeutically. While not limited to any specific theory, it is contemplated that elimination of interfering antibodies will be accompanied by a reduction in nonneutralizing effect associated with passive immunization of immune globulin.

Immunoaffinity purification/isolation by use of an "antigen matrix" comprised of epitope II attached to an insoluble support can be performed. Antibody to be purified is applied in solution to the antigen matrix. The solution passes through the antigen matrix and comprises the "flow through." Antibody that does not bind, if present, passes with the solution through the antigen matrix into the flow through. Immunoaffinity purification/isolation can promote maximum attachment of the interfering antibodies to the resin, which may improve recovery of the neutralizing antibodies in an active state. Immunoaffinity purification also allows for the antibody to be eluted quantitatively; that is, there is no significant retained antibody to progressively decrease column capacity after successive cycles of use, i.e., the antigen matrix is recyclable. Further, immunoaffinity purification can promote the retention of a full spectrum of neutralizing antibodies.

Immunoaffinity purification/isolation by use of an "antigen matrix" comprised of epitope II(s) attached to an insoluble support is contemplated. Antibody to be purified is applied in solution to the antigen matrix. The solution passes through the antigen matrix and comprises the "flow through." Neutralizing antibody that does not bind, if present, passes with the solution through the antigen matrix into the flow through. To eliminate all non-binding antibody, the matrix is "washed" with one or more wash solutions which, after passing through the matrix, comprise one or more "effluents." "Eluent" is a chemical solution capable of dissociating antibody bound to the antigen matrix (if any) that passes through the antigen matrix and comprises an "eluate." Antibody that is dissociated (if any) is freed from the antigen matrix and passes by elution with the eluent into the eluate. In one embodiment, the material for the insoluble support (hereinafter "resin") takes the form of spherical beads. In one preferred embodiment, the resin is a synthetic polymer capable of forming a gel in aqueous media (e.g., agarose).

Epitope II or a peptide having $LFY^{443}$ or $LLY^{443}$ sequence (e.g., a peptide that is at least, equal to, less than, or greater than 5, 6, 7, 8, 9, 10, 11, 12, 13, 14, 15, 16, 17, 18, 19, 20, 21, 22, 23, 24, 25, 26, 27, 28, 30, 40, or 50 amino acids in length containing the $LFY^{443}$ or $LLY^{443}$ sequence, such as SEQ. ID. NOs. 30, 31, 33, 34, 36, 38, 41, 42, or 43), as described above, can be immobilized to a support. Epitope II or a peptide having $LFY^{443}$ or $LLY^{443}$ sequence (e.g., a peptide that is at least, equal to, less than, or greater than 5, 6, 7, 8, 9, 10, 11, 12, 13, 14, 15, 16, 17, 18, 19, 20, 21, 22, 23, 24, 25, 26, 27, 28, 30, 40, or 50 amino acids in length containing the $LFY^{443}$ or $LLY^{443}$ sequence, such as SEQ. ID. NOs. 30, 31, 33, 34, 36, 38, 41, 42, or 43) can be physically trapped in a gel; this approach does not rely upon any particular chemical reactivities of the epitope II. Epitope II or a peptide having $LFY^{443}$ or $LLY^{443}$ sequence (e.g., a peptide that is at least, equal to, less than, or greater than 5, 6, 7, 8, 9, 10, 11, 12, 13, 14, 15, 16, 17, 18, 19, 20, 21, 22, 23, 24, 25, 26, 27, 28, 30, 40, or 50 amino acids in length containing the $LFY^{443}$ or $LLY^{443}$ sequence, such as SEQ. ID. NOs. 30, 31, 33, 34, 36, 38, 41, 42, or 43) can also be covalently coupled to an "activated" matrix; this approach relies on the existence of functional groups that can covalently bond with the matrix. Epitope H or a peptide having $LFY^{443}$ or $LLY^{443}$ sequence (e.g., a peptide that is at least, equal to, less than, or greater than 5, 6, 7, 8, 9, 10, 11, 12, 13, 14, 15, 16, 17, 18, 19, 20, 21, 22, 23, 24, 25, 26, 27, 28, 30, 40, or 50 amino acids in length containing the $LFY^{443}$ or $LLY^{443}$ sequence, such as SEQ. ID. NOs. 30, 31, 33, 34, 36, 38, 41, 42, or 43) can also be coupled to an insoluble support using bifunctional reagents as linking groups that react with a) side groups on Epitope II or a peptide having $LFY^{443}$ and b) groups on the insoluble support.

In a preferred embodiment, a covalent attachment method for Epitope II or a peptide having $LFY^{443}$ or $LLY^{443}$ sequence (e.g., a peptide that is at least, equal to, less than, or greater than 5, 6, 7, 8, 9, 10, 11, 12, 13, 14, 15, 16, 17, 18, 19, 20, 21, 22, 23, 24, 25, 26, 27, 28, 30, 40, or 50 amino acids in length containing the $LFY^{443}$ or $LLY^{443}$ sequence, such as SEQ. ID. NOs. 30, 31, 33, 34, 36, 38, 41, 42, or 43) that allows for high coupling efficiency and high antibody binding capacity is provided. It is preferred because of the ease and efficiency of antigen attachment, the stability of the attachment (relative to resins involving non-covalent attachment), and mechanical and chemical strength towards denaturants that are used during chromatographic procedures. In one embodiment, the covalent attachment method employs cyanogen bromide activated Sepharose 4B (Pharmacia) as a resin for covalent attachment of epitope II. The preferred resins with active groups for covalent attachment are resins with aldehydes as active groups ("aldehydeactivated resins"). One preferred resin is aldehyde-activated agarose. It is not intended that the immunoaffinity purification/isolation be limited to any particular genotype of epitope II or subtype of epitope II. In the preferred embodiment, however, a cocktail is used. One preferred binding of the epitope II, whether a particular genotype or subtype of epitope II or cocktail of epitope IIs, to an aldehyde-activated resin is via sodium cyanoborohydride reduction.

In a preferred embodiment, the antigen matrix is "pre-stripped" with an eluent prior to any further use of the antigen matrix. By pre-stripping, the purification of the present invention avoids contamination of immunoaffinity purified immune globulin preparations with epitope H that failed to attach to the resin. It was noted above that by using the same genotype or subtype of epitope II or cocktail of epitope IIs in the antigen matrix, the purified immune globulin derived from unpurified immune globulin has a retention of the neutralization reactivity of the unpurified immune globulin. The retention of the neutralization reactivity is achieved when one, in addition to using the same genotype or subtype of epitope II or cocktail of epitope IIs in the antigen matrix, uses the epitope II or cocktail of epitope IIs in the antigen matrix at a concentration that allows for the presentation of antigen in greater amounts than that needed to bind all of the interfering antibody applied to the antigen matrix. The latter is achieved by monitoring the flow through for neutralization reactivity as the unpurified antibody is applied; where the flow through shows a less than 10% reduction of the neutralization reactivity of the unpurified antibody that is applied, the epitope II or cocktail of epitope IIs in the antigen matrix is viewed to be at a concentration that allows for the presentation of antigen in greater amounts than that needed to bind all of the interfering antibody applied to the antigen matrix.

In a preferred embodiment, the purification/isolation allows for separation from the interfering antibodies of the neutralizing antibodies present initially in the immune globulin, retention of neutralization activity, and recyclability of the matrix, by a first elution with a non-denaturing eluent and a second elution with denaturing eluent. The first elution recovers the neutralizing antibody. The second elution recovers the interfering antibody and recycles the antigen matrix. Thus, a method may comprise the steps: 1) preparation of the epitope II-matrix; 2) binding of the interfering antibody to the epitope II-matrix and collecting the flow through neutralizing antibody, and 3) elution of the interfering antibody. The EP II-specific inhibitory antibody can then be used to identify and/or generate inhibitors (such as antiidiotype antibodies), as described below.

As mentioned above, some embodiments include a composition that comprises a purified immune globulin in amounts sufficient to produce a neutralization activity greater than the neutralization activity of the unpurified immune globulin or to produce a neutralization of HCV greater than that of the unpurified immune globulin. As the preferred purified immune globulin (IG) one may use material prepared in the same manner in which material intended for intravenous (IVIG) use is prepared. IVIG is well known and can be prepared by known means, such as ultracentrifugation, pH adjustments, careful fractionation, enzymatic modification, structural modification, chemical modification, and reduction and alkylation.

Other methods of fractionation to yield IG which may be used include polyelectrolyte affinity adsorption, large scale electrophoresis, ion exchange adsorption, polyethylene glycol fractionation, and so forth. However, any method which fractionates an immune globulin comprising either IgG, IgM, IgA, IgE, or IgD or subclasses thereof from a human or non-human source may be used in the present invention. Also included in the scope of the invention are therapeutically active fragments of IG such as, for example, Fc, Fd, or Fab fragments. Also contemplated are purified IG products manufactured using biotechnology, i.e., monoclonal antibody or recombinant DNA techniques.

Usually the composition containing purified immune globulin is substantially free of other proteins normally found in plasma, that is, contains 15% or less, preferably 10% or less, of such protein. However, it is possible to incorporate into the composition other proteins in amounts as needed under a particular circumstance. A preferred product is a sterile pharmaceutical composition for therapeutic use, which is suitable for intravenous administration. The product may be in lyophilized form to be reconstituted for use by addition of a suitable diluent, or it may be in the form of an aqueous solution.

For reconstitution of a lyophilized product, one may employ sterile diluent, which may contain materials generally recognized for approximating physiological conditions and/or as required by governmental regulation. In this respect the sterile diluent may contain a buffering agent to obtain a physiologically acceptable pH, sodium chloride, and/or other substances which are physiologically acceptable and/or safe for human use. In general, the material for intravenous injection should conform to regulations established by the U.S. Food and Drug Administration, which are available to those in the field. The protein concentration of the product of the invention should be about 0.1-30%, preferably about 1-15%, on a weight to volume basis.

Pharmaceutical compositions, as described herein, may also be in the form of an aqueous solution containing many of the same substances as described above for the reconstitution of a lyophilized product. It is also contemplated that stabilizing agents for the immune globulin can be used. For instance, some embodiments may contain a carbohydrate such as a sugar or sugar alcohol or maltose.

It may be preferred to administer a product that is free of infective hepatitis virus. In this respect the composition may be treated to reduce hepatitis infectivity by, for example, pasteurization, i.e., heating at a temperature and for a time, such as about 60° C. or more for a period of about 10 hours or more. To stabilize the proteins in the instant composition to heat, one may use a carbohydrate either alone or in conjunction with an amino acid or other known stabilizing agents. For this purpose one may use as the carbohydrate a mono-, di-, or trisaccharide such as arabinose, glucose, galactose, maltose, fructose, fibose, mannose, rhammose, cusrose, etc., or a sugar alcohol such as sorbitol and mannitol, etc., in an amount of about 0.5-2.4 g/ml of a solution containing 0.1-10% protein.

As mentioned above the products may be incorporated into pharmaceutical preparations, which may be used for therapeutic purposes. However, the term "pharmaceutical preparation" is intended in a broader sense herein to include preparations containing a protein composition in accordance with this invention used not only for therapeutic purposes, but also for reagent or diagnostic purposes as known in the art or for tissue culture. The pharmaceutical preparation intended for therapeutic use should contain a therapeutic amount of immune globulin, i.e., that amount necessary for preventative or curative health measures. If the pharmaceutical preparation is to be employed as a reagent or diagnostic, then it should contain reagent or diagnostic amounts of immune globulin.

Immunogenic Compositions

Once produced, the envelope polypeptides or other immunogens as described herein may also be provided in immunogenic compositions, in e.g., prophylactic (i.e., to prevent infection) or therapeutic (to treat HCV following infection) vaccine or immunogenic compositions. The compositions can comprise mixtures of more than one envelope polypeptide, at least one of the polypeptides derived from any one of HCV genotypes 1, 4, 5 and/or 6, and at least one of the polypeptides derived from HCV genotype 2 and/or 3. In fact, HCV envelope polypeptides from all of these genotypes can be present, if desired.

The compositions will generally include one or more "pharmaceutically acceptable excipients or vehicles" such as water, saline, glycerol, ethanol, etc. Additionally, auxiliary substances, such as wetting or emulsifying agents, pH buffering substances, and the like, may be present in such vehicles. A carrier is optionally present which is a molecule that does not itself induce the production of antibodies harmful to the individual receiving the composition. Suitable carriers are typically large, slowly metabolized macromolecules such as proteins, polysaccharides, polylactic acids, polyglycollic acids, polymeric amino acids, amino acid copolymers, lipid aggregates (such as oil droplets or liposomes), and inactive virus particles. Such carriers are well known to those of ordinary skill in the art. Furthermore, the HCV polypeptide may be conjugated to a bacterial toxoid, such as toxoid from diphtheria, tetanus, cholera, etc.

Pharmaceutically acceptable salts can also be used in the compositions described herein, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art. Some embodiments can also contain liquids or excipients, such as water, saline, glycerol, dextrose, ethanol, or the like, singly or in combination, as well as substances such as wetting agents, emulsifying agents, or pH buffering agents. The proteins or polynucleotides described herein can also be adsorbed to, entrapped within or otherwise associated with liposomes and particulate carriers such as PLG. Liposomes and other particulate carriers are described above. Some of the nucleic acid embodiments described herein can be provided in vectors that promote expression of the proteins in humans, as are known in the art of DNA vaccination. The DNA immunogens described herein can be provided by gene guns, electroporation, air jets, ballistic transformation, powder injections and the like.

If desired, co-stimulatory molecules, which improve immunogen presentation to lymphocytes, such as B7-1 or B7-2, or cytokines, lymphokines, and chemokines, including but not limited to cytokines such as IL-2, GM-CSF, IL-12, γ-interferon, IP-10, MTP1β, FLP-3, ribavirin and RANTES, may be included in the composition. Optionally, adjuvants can also be included in a composition. Adjuvants which can be used include, but are not limited to: (1) mineral containing compositions, such as alum; (2) oil-in water emulsions, such as MF59, SAF and Ribi™ adjuvant system (RAS); (3) saponin formulations; (4) virosomes and virus like particles (VLPs); (5) non-toxic derivatives of enterobacterial lipopolysaccharide (LPS), such as monophosphoryl lipid A (MPL); (6) lipid A derivatives; (7) immunostimulatory oligonucleotides, such as nucleotide sequences containing a CpG motif; (8) ADP-ribosylating toxins and detoxified derivatives thereof; (9) bioadhesives and mucoadhesives; (10) microparticles; (11) liposomes; (12) polyoxyethylene ether and polyoxyethylene ester formulations; (13) polyphosphazene (PCPP); (14) muramyl peptides; (15) small molecule immunopotentiators (SMIPs), such as imidazoquinoline compounds; and (16) human immunomodulators, for example, cytokines, such as interleukins (e.g. IL-1, IL-2, IL-4, IL-5, IL-6, IL-7, IL-12, etc.), interferons (e.g., interferon-γ), macrophage colony stimulating factor, and tumor necrosis factor.

It is contemplated that the aforementioned peptides and nucleic acids can induce an immunological response in a vertebrate subject, preferably a primate, such as a human, when these compositions are provided in a pharmaceutical form. An "immunological response" to an HCV antigen or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells. A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host. The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art.

By "vertebrate subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

Typically, the compositions described above are prepared as injectables, either as liquid solutions or suspensions; solid forms suitable for solution in, or suspension in, liquid vehicles prior to injection may also be prepared. Thus, once formulated, the compositions are conventionally administered parenterally, e.g., by injection, either subcutaneously or intramuscularly. Additional formulations suitable for other modes of administration include oral and pulmonary formulations, suppositories, and transdermal applications. Dosage treatment may be a single dose schedule or a multiple dose schedule. Preferably, the effective amount is sufficient to bring about treatment or prevention of disease symptoms. The exact amount necessary will vary depending on the subject being treated; the age and general condition of the individual to be treated; the capacity of the individual's immune system to synthesize antibodies; the degree of protection desired; the severity of the condition being treated; the particular macromolecule selected and its mode of administration, among other factors. An appropriate effective amount can be readily determined by one of skill in the art. A "therapeutically effective amount" will fall in a relatively broad range that can be determined through routine trials using in vitro and in vivo models known in the art.

For example, the composition is preferably injected intramuscularly to a large mammal, such as a primate, for example, a baboon, chimpanzee, or human. The amount of polypeptide administered will generally be about 0.1 µg to about 5.0 mg per dose, or any amount between the stated ranges, such as 0.5 µg to about 10 mg, 1 µg to about 2 mg, 2.5 µg to about 250 µg, 4 µg to about 200 µg, such as 4, 5, 6, 7, 8, 9, 10 . . . 20 . . . 30 . . . 40 . . . 50 . . . 60 . . . 70 . . . 80 . . . 90 . . . 100, etc., µg per dose. The compositions can be administered either to a mammal that is not infected with an HCV or can be administered to an HCV-infected mammal.

Administration of the HCV polypeptides can elicit a cellular immune response, and/or an anti-E2 antibody titer in the mammal that lasts for at least 1 week, 2 weeks, 1 month, 2 months, 3 months, 4 months, 6 months, 1 year, or longer. The HCV envelope polypeptides can also be administered to provide a memory response. If such a response is achieved, antibody titers may decline over time, however exposure to HCV or immunogen results in the rapid induction of antibodies, e.g., within only a few days. Optionally, antibody titers can be maintained in a mammal by providing one or more booster injections of the polypeptides at 2 weeks, 1 month, 2 months, 3 months, 4 months, 5 months, 6 months, 1 year, or more after the primary injection.

Preferably, an antibody titer of at least 10, 100, 150, 175, 200, 300, 400, 500, 750, 1,000, 1,500, 2,000, 3,000, 5,000, 10,000, 20,000, 30,000, 40,000, 50,000 (geometric mean titer), or higher, is elicited, or any number between the stated titer, as determined using a standard immunoassay, such as the immunoassay described in, e.g., Chien et al., Proc Natl Acad Sci USA. 1992 89: 10011-5.

In order to determine whether the HCV envelope polypeptides are capable of eliciting a neutralizing antibody reaction, neutralization assays can be performed using techniques well known in the art. For example sera can be isolated from an immunized subject and analyzed using an HCV pseudoparticle (HCVpp) assay, as described in e.g., Bartosch et al. 2003 *J Exp Med* 197:633-642 or using an HCV cell culture (HCVcc) system that allows a relatively efficient amplification of virus, as described in Lindenbach et al., Science. 2005 309: 623-6; and Wakita et al., Nat Med. 2005 11: 791-6. Additionally, assays to determine the presence of neutralization of binding (NOB) antibodies can be performed as described in, e.g., Rosa et al. 1996 *Proc Natl Acad Sci USA* 93:1759.

Immune responses of the mammal generated by the delivery of the aforementioned compositions can be enhanced by varying the dosage, route of administration, or boosting regimens. The compositions described herein may be given in a single dose schedule, or preferably in a multiple dose schedule in which a primary course of vaccination includes 1-10 separate doses, followed by other doses given at subsequent time intervals required to maintain and/or reinforce an immune response, for example, at 1-4 months for a second dose, and if needed, a subsequent dose or doses after several months.

Some of the DNA-based immunogens described herein are also provided with a replication-deficient adenovirus which, may be effective to boost to an immune response primed to antigen. Replication-deficient adenovirus derived from human serotype 5 has been developed as a live viral vector by previous investigators. Adenoviruses are non-enveloped viruses containing a linear double stranded DNA genome of around 3600 bp. Recombinant viruses can be constructed by in vitro recombination between an adenovirus genome plasmid and a shuttle vector containing the gene of interest together with a strong eukaryotic promoter, in a permissive cell line which allows viral replication. High viral titers can be obtained from the permissive cell line, but the resulting viruses, although capable of infecting a wide range of cell types, do not replicate in any cells other than the permissive line, and are therefore a safe antigen delivery system. Recombinant adenoviruses have been shown to elicit protective immune responses against a number of antigens.

In some embodiments, the recombinant replication-defective adenovirus expressing the peptides described herein are used to boost an immune response primed by a DNA immunogen prepared as described herein, VLPs or recombinant modified vaccinia ankara (MVA). The replication-defective adenovirus is found to induce an immune response after intradermal or intramuscular immunization. In prime/boost vaccination regimes the replication-defective adenovirus is also able to prime a response that can be boosted by a DNA vaccine, VLPs, or MVA. Some embodiments employ a replication-deficient adenovirus vector encoding an antigen for boosting an immune response to the antigen primed by previous administration of the antigen or nucleic acid encoding the antigen. A general aspect of some of the immunogens described herein is that they provide for the use of a replication-deficient adenoviral vector for boosting an antibody or CD8+ T cell immune response to an antigen.

Some aspects of the invention concern methods of boosting an immune response to an antigen in an individual, the method including provision in the individual of a replication-deficient adenoviral vector including nucleic acid encoding an antigen, as described herein, operably linked to regulatory sequences for production of antigen in the individual by expression from the nucleic acid, whereby an immune response to the antigen previously primed in the individual is boosted.

The priming composition may comprise any viral vector, although generally other than adenoviral, such as a vaccinia virus vector such as a replication-deficient strain such as modified vaccinia ankara (MVA) or NYVAC, an avipox vector such as fowlpox or canarypox, e.g., the strain known as ALVAC, or an alphavirus vector. The priming composition may comprise a recombinant bacterial vector, such as recombinant BCG or *Salmonella*. A priming composition comprising a DNA vaccine is among preferred embodiments for use in the present invention.

The priming composition may comprise DNA encoding the antigen, such DNA preferably being in the form of a circular plasmid that is not capable of replicating in mammalian cells. Any selectable marker should not be resistant to an antibiotic used clinically, so for example Kanamycin resistance is preferred to Ampicillin resistance. Antigen expression should be driven by a promoter which is active in mammalian cells, for instance the cytomegalovirus immediate early (CMV IE) promoter.

The priming composition may be a recombinant virus like particle (VLP). These are particles that resemble the HCV virions. They are produced using a recombinant baculovirus containing the cDNA of the HCV structural proteins. Other suitable priming compositions include lipid-tailed peptides, fusion proteins, adjuvant compositions and so on.

In particular embodiments, administration of a priming composition is followed by boosting with first and second boosting compositions, the first and second boosting compositions being different from one another. In one embodiment, a triple immunization regime employs DNA, then adenovirus as a first boosting composition, and then MVA as a second boosting composition, optionally followed by a further (third) boosting composition or subsequent boosting administration of one or other or both of the same or different vectors. Another option is DNA then MVA then Ad, optionally followed by subsequent boosting administration of one or other or both of the same or different vectors.

The antigen to be included in respective priming and boosting compositions (however many boosting compositions are employed) need not be identical, but should share at least one neutralization or CD8+ T cell epitope. The antigen may correspond to a complete antigen in a target pathogen or cell, or a fragment thereof. Peptide epitopes or artificial strings of epitopes may be employed, more efficiently cutting out unnecessary protein sequence in the antigen and encoding sequence in the vector or vectors. One or more additional epitopes may be included, for instance epitopes which are recognized by T helper cells, especially epitopes recognized in individuals of different HLA types.

Within the replication-deficient adenoviral vector, regulatory sequences for expression of the encoded antigen will include a promoter. By "promoter" is meant a sequence of nucleotides from which transcription may be initiated of DNA operably linked downstream (i.e., in the 3' direction on the sense strand of double-stranded DNA). "Operably linked" means joined as part of the same nucleic acid molecule, suitably positioned and oriented for transcription to be initiated from the promoter. DNA operably linked to a promoter is. "under transcriptional initiation regulation" of the promoter. Other regulatory sequences including terminator fragments, polyadenylation sequences, enhancer sequences, marker genes and other sequences may be included as appropriate, in accordance with the knowledge and practice of the ordinary person skilled in the art: see, for example, *Molecular Cloning: a Laboratory Manual:* 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Ausubel et al. eds., John Wiley & Sons, 1994. Suitable promoters for use in aspects and embodiments of the present invention include the cytomegalovirus immediate early (CMV IE) promoter, with or without intron A, and any other promoter that is active in mammalian cells.

Either or both of the priming and boosting compositions may include an adjuvant, such as granulocyte macrophage-colony stimulating factor (GM-CSF) or encoding nucleic acid therefor. Administration of the boosting composition is generally about 10 days to 4 weeks after administration of the priming composition, preferably about 2-3 weeks, Preferably, administration of priming composition, boosting composition, or both priming and boosting compositions, is intradermal or intramuscular immunization Intradermal administration of adenovirus and MVA vaccines may be achieved by using a needle to inject a suspension of the virus. An alternative is the use of a needleless injection device to administer a virus suspension (using e.g., Biojector™) or a freeze-dried powder containing the vaccine (e.g., in accordance with techniques and products of Powderject), providing for manufacturing individually prepared doses that do not need cold storage. This would be a great advantage for a vaccine that is needed in rural areas of Africa.

Adenovirus and MVA are both viruses with an excellent safety record in human immunizations. The generation of recombinant viruses can be accomplished simply, and they can be manufactured reproducibly in large quantities. Intradermal administration of recombinant replication-deficient adenovirus followed by recombinant MVA is therefore highly suitable for prophylactic or therapeutic vaccination of humans against diseases which can be controlled by an immune response.

Components to be administered in accordance with the present invention may be formulated in pharmaceutical compositions. These compositions may comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g., intravenous, cutaneous or subcutaneous, nasal, intramuscular, intraperitoneal routes. As noted, administration is preferably intradermal, subcutaneous or intramuscular. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required. A slow-release formulation may be employed. Following production of replication-deficient adenoviral particles and optional formulation of such particles into compositions, the particles may be administered to an individual, particularly human or other primate. Administration may be to another mammal, e.g., rodent such as mouse, rat or hamster, guinea pig, rabbit, sheep, goat, pig, horse, cow, donkey, dog or cat.

Administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g., decisions on dosage etc, is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A., Ed., 1980. In one preferred regimen, DNA is administered (preferably intramuscularly) at a dose of 0.5 mg/injection, followed by adenovirus (preferably intramuscularly or intradermally) at a dose of $5 \times 10^7$-$5 \times 10^8$ virus particles/injection. A composition may be administered alone or in combination with other treatments, either simultaneously or sequentially dependent upon the condition to be treated. Delivery to a non-human mammal need not be for a therapeutic purpose, but may be for use in an experimental context, for instance in investigation of mechanisms of immune responses an antigen of interest, e.g., protection against pathogens.

Epitope II Inhibitors that Block the Inhibition of Neutralization

Some embodiments include inhibitors of the EP. II-specific inhibitory antibodies, methods of identifying such inhibitors and methods of making pharmaceuticals that include these compositions. Ideally, the inhibitors of the EP II-specific antibodies are molecules that are ligands for the antibodies that mimic the EP II binding site. Desirably, the inhibitors contain the $LFY^{443}$ or $LLY^{443}$ sequence (e.g., a peptide that is at least, equal to, less than, or greater than 5, 6, 7, 8, 9, 10, 11, 12, 13, 14, 15, 16, 17, 18, 19, 20, 21, 22, 23, 24, 25, 26, 27, 28, 30, 40, or 50 amino acids in length containing the $LFY^{443}$ or $LLY^{443}$ sequence, such as SEQ. ID. NOs. 30, 31, 33, 34, 36, 38, 41, 42, or 43).

In some embodiments, an EP II decoy inhibitor can be created by providing the peptides above having one or more D amino acids, or fragments thereof. In fact, EP II decoy inhibitors have been made and were used to deplete EP II specific antibodies from preparations containing both neutralization antibodies (i.e., EP I specific antibodies) and neutralization inhibitory antibodies (i.e., EP II specific antibodies) (see Examples). These first generation EP II decoys can be provided to subjects that have been identified as needing an inhibitor for EP II specific antibodies in a pharmaceutical form, as described herein. Such subjects, e.g., patients chronically infected with HCV, can be identified using clinical evaluation or a diagnostic assay as known in the art or as provided below. By some approaches, the EP 11 decoys are provided in protein form and in other embodiments, nucleic acids encoding the EP II decoys are provided using techniques in conventional DNA immunization (e.g., the nucleic acid is incorporated into a potent expression vector, which is injected into the muscle, which is stimulated by an electric pulse).

A second generation of EP II decoys can be made by attaching an antigenic protein molecule that promotes clearance by the immune system to the EP II domain or a fragment thereof, preferably a peptide containing the $LFY^{443}$ or $LLY^{443}$ sequence (e.g., a peptide that is at least, equal to, less than, or greater than 5, 6, 7, 8, 9, 10, 11, 12, 13, 14, 15, 16, 17, 18, 19, 20, 21, 22, 23, 24, 25, 26, 27, 28, 30, 40, or 50 amino acids in length containing the $LFY^{443}$ or $LLY^{443}$ sequence, such as SEQ. ID. NOs. 30, 31, 33, 34, 36, 38, 41, 42, or 43).

Some embodiments, for example include fusion proteins or nucleic acids encoding the same, which in addition to the EP II domain or a peptide containing the $LFY^{443}$ or $LLY^{443}$ sequence (e.g., a peptide that is at least, equal to, less than, or greater than 5, 6, 7, 8, 9, 10, 11, 12, 13, 14, 15, 16, 17, 18, 19, 20, 21, 22, 23, 24, 25, 26, 27, 28, 30, 40, or 50 amino acids in length containing the $LFY^{443}$ or $LLY^{443}$ sequence, such as SEQ. ID. NOs. 30, 31, 33, 34, 36, 38, 41, 42, or 43) encode a second potent protein antigen to which the human has already acquired an immune response (e.g., a polio virus sequence). By this approach, antibodies specific for the fused antigen (e.g., polio virus sequence) are bound to the complex of EP II specific antibodies that are bound to the EP II decoy and the entire complex is cleared by the immune system. By some approaches, the EP II decoys are provided in protein form and in other embodiments, nucleic acids encoding the EP II decoys are provided using techniques in conventional DNA immunization (e.g., the nucleic acid is incorporated into a potent expression vector, which is injected into the muscle, which is stimulated by an electric pulse). The antigenic sequences described in U.S. Pat. Nos. 6,933,366 and 6,469,143, can be used in these embodiments and the antigenic sequences described in the aforementioned patents are hereby expressly incorporated by reference in their entireties.

A third generation of EP II decoys can be made by attaching an antigenic sugar molecule that promotes clearance by the immune system to the EP II domain or a fragment thereof, preferably a peptide containing the $LFY^{443}$ or $LLY^{443}$ sequence (e.g., a peptide that is at least, equal to, less than, or greater than 5, 6, 7, 8, 9, 10, 11, 12, 13, 14, 15, 16, 17, 18, 19, 20, 21, 22, 23, 24, 25, 26, 27, 28, 30, 40, or 50 amino acids in length containing the $LFY^{443}$ or $LLY^{443}$ sequence, such as SEQ. ID. NOs. 30, 31, 33, 34, 36, 38, 41, 42, or 43). Some embodiments, for example include fusion proteins, which in addition to the EP II domain or a peptide containing the $LFY^{443}$ or $LLY^{443}$ sequence (e.g., a peptide that is at least, equal to, less than, or greater than 5, 6, 7, 8, 9, 10, 11, 12, 13, 14, 15, 16, 17, 18, 19, 20, 21, 22, 23, 24, 25, 26, 27, 28, 30, 40, or 50 amino acids in length containing the $LFY^{443}$ or $LLY^{443}$ sequence, such as SEQ. ID. NOs. 30, 31, 33, 34, 36, 38, 41, 42, or 43) is chemically linked or coupled to a sugar moiety (e.g., the gal epitope), which is a potent antigen to which the human has already acquired an immune response. By this approach, antibodies specific for the fused antigen (e.g., gal epitope) are bound to the complex of EP II specific antibodies that are bound to the EPII decoy and the entire complex is cleared by the immune system. The technology for chemically coupling the gal epitope to small peptides is well known and can be applied readily to generate the third generation of EP II decoys. Please see U.S. Pat. Nos. 7,318,926 and 7,019,111, which describe this technology in detail, the disclosures of which in the aforementioned patents are hereby expressly incorporated by reference in their entireties.

The gal epitope or gal antigen is produced in large amounts on the cells of pigs, mice and New World monkeys by the glycosylation enzyme galactosyltransferase (alpha(1,3)GT). Galactosyltransferase is active in the Golgi apparatus of cells and transfers galactose from the sugar-donor uridine diphosphate galactose (UDP-galactose) to the acceptor N-acetyllactosamine residue on carbohydrate chains of glycolipids and glycoproteins, to form gal antigen. The gal antigen is completely absent in humans, apes and Old World monkeys because their genes encoding alpha (1,3) GT have become inactivated in the course of evolution. (Xing et al., 01-2-x1 Cell Research 11(2): 116-124 (2001), herein expressly incorporated by reference in its entirety.) Since humans and Old World primates lack the gal antigen, they are not immunotolerant to it and produce anti-gal antigen antibodies (anti-Gal) throughout life in response to antigenic stimulation by gastrointestinal bacteria. (Id.) It has been estimated that as many as 1% of circulating B cells are capable of producing these antibodies. (Id.) The binding of anti-Gal to gal antigens expressed on glycolipids and glycoproteins on the surface of endothelial cells in donor organs leads to activation of the complement cascade and hyperacute rejection, and also plays an important role in occurrence of complement-independent delayed xenograft rejection. (Id.) Accordingly, the gal antigen has the ability to generate a potent immune response.

By one approach, an isolated glycoconjugate peptide comprising an EP II-specific antibody binding fragment of the EP II domain of the E 2 protein is synthetically conjugated to gal alpha(1,3) gal beta (i.e., the "gal epitope" or "gal antigen") using synthetic chemistry. Preferably, the glycoconjugate peptide comprising an EP II-specific antibody binding fragment of the EP II domain of the E 2 protein comprises, consists, or consists essentially of the $LFY^{443}$ or $LLY^{443}$ sequence (e.g., a peptide that is at least, equal to, less than, or greater than 5, 6, 7, 8, 9, 10, 11, 12, 13, 14, 15, 16, 17, 18, 19, 20, 21, 22, 23, 24, 25, 26, 27, 28, 30, 40, or 50 amino acids in length containing the $LFY^{443}$ or $LLY^{443}$ sequence, such as SEQ. ID. NOs. 30, 31, 33, 34, 36, 38, 41, 42, or 43). In some embodiments, the gal epitope is synthetically conjugated to a hydroxylated amino acid present on the EP II domain or a peptide that comprises, consists, or consists essentially of the $LFY^{443}$ or $LLY^{443}$ sequence (e.g., a peptide that is at least, equal to, less than, or greater than 5, 6, 7, 8, 9, 10, 11, 12, 13, 14, 15, 16, 17, 18, 19, 20, 21, 22, 23, 24, 25, 26, 27, 28, 30, 40, or 50 amino acids in length containing the $LFY^{443}$ or $LLY^{443}$ sequence, such as SEQ. ID. NOs. 30, 31, 33, 34, 36, 38, 41, 42, or 43). Alternatively, the gal epitope is synthetically conjugated to the EP II-specific antibody binding fragment of the EP II domain of the E 2 protein or a peptide that comprises, consists, or consists essentially of the $LFY^{443}$ sequence by an $NH_2$-linkage. In another embodiment, the isolated glycoconjugate peptide is created by synthetically conjugating the gal epitope to the N-terminal end of the EP II-specific antibody binding fragment of the EP II domain of the E 2 protein or a peptide that comprises, consists, or consists essentially of the $LFY^{443}$ or $LLY^{443}$ sequence (e.g., a peptide that is at least, equal to, less than, or greater than 5, 6, 7, 8, 9, 10, 11, 12, 13, 14, 15, 16, 17, 18, 19, 20, 21, 22, 23, 24, 25, 26, 27, 28, 30, 40, or 50 amino acids in length containing the $LFY^{443}$ or $LLY^{443}$ sequence, such as SEQ. ID. NOs. 30, 31, 33, 34, 36, 38, 41, 42, or 43), as described above.

The glyco-amino-acids that can be used with the embodiments described herein comprise a saccharide attached to a single amino acid, whereas the glycosyl-amino-acids that can be used include compounds comprising a saccharide linked through a glycosyl linkage (O—, N— or S—) to an amino acid. (The hyphens are used to avoid implying that the carbohydrate is necessarily linked to the amino group.) In some embodiments, the antigenic domain comprises a glycolipid, which is a compound comprising one or more monosaccharide residues bound by a glycosidic linkage to a hydrophobic moiety such as an acylglycerol, a sphingoid, a ceramide (N-acylsphingoid) or a prenyl phosphate, for example. Some of the specificity exchangers described herein can also comprise a glycoconjugate (e.g., lectins).

Another approach to develop inhibitors for the EP II-specific antibodies involves the development of anti-idiotype antibodies or fragments thereof (e.g., Fab fragments) that are directed to epitopes on the EP II-specific antibodies that interfere with the binding of the EP II-specific antibodies to the EP II domain and/or interaction/inhibition of binding of the EP I-specific neutralization antibodies. Polyclonal antibodies that are specific for EP II and which are involved in the inhibition of binding of EP-I specific antibodies have been isolated from plasma obtained from patients that are chronically infected with HCV, as described above. Anti-idiotype antibodies that are specific for epitopes on these polyclonal EP II-specific antibodies involved in inhibiting the binding or the HCV neutralization antibodies can be developed by utilizing techniques that are well known. Please see e.g., U.S. Pat. No. 5,053,224, hereby expressly incorporated by reference in its entirety, which describes such techniques that can be readily adapted as provided below.

The idiotype of an antibody is defined by individually distinctive antigenic determinants in the variable or idiotypic region of the antibody molecule. A portion of these idiotypic determinants will be on or closely associated with the parotope of the antibody, while others will be in the framework of the variable region. While each antibody has its own idiotype, particular antibodies will be referred to below by the following terms. "Idiotype antibody" or "Id Ab" refers to an anti-EP II-specific antibody (i.e, the epitope identified by the idiotype antibody is an epitope required for binding to the EP II domain, such as the $LFY^{433}$ sequence. "Anti-idiotype antibody" or "anti-Id Ab" refers to an antibody which identifies an epitope in the variable region of an idiotype antibody. A portion of such antibodies will identify an epitope that is the parotope antibody, thus presenting an "internal" image of the epitope identified by the idiotype antibody. "Anti-(anti-idiotype) antibody" or "anti-(anti-Id) Ab" is an antibody that identifies an epitope in the variable region of the anti-idiotype antibody. A portion of the anti-(anti-idiotype) antibodies will identify an epitope that corresponds to (i) the parotope of the anti-idiotype antibody, and (ii) an epitope on EP II required for binding of the EP II-specific antibody.

As stated below, some methods contemplate administering anti-idiotype antibody to a host to block the inhibition mediated by the EP II-specific antibodies. The anti-idiotype antibody is administered to the host in any physiologically suitable carrier (e.g., sterile, pyrogen-free physiological saline), as described above. The selection of carrier is not critical and the antibody can be administered by any method that introduces the antibody into the circulatory system (e.g., intravenous, intramuscular or subcutaneous injection).

The amount of antibody administered to a host can vary, for example, upon the particular antibody employed and the patient inoculated. It is only necessary that sufficient anti-idiotype antibody be administered to stimulate the production of anti-(anti-idiotype) antibodies by the patient's immune system. The amounts of antibody employed, need not be very great because only very small amounts are necessary to induce an immunological response. In many cases, a dosage of antibody within the range of a few micrograms to a few milligrams should be sufficient, (e.g., about 50-200 ug to about 1-5 mg). The determination of an appropriate dosage is readily within the skill of the art.

One approach, for example, contemplates administering a formulation containing anti-idiotype antibody to a human patient that is chronically infected with HCV so as to produce an immunological response to the EP II specific antibody. As defined above, a subclass of the anti-idiotype antibody selectively binds to (i.e., identifies) the parotope of an EP II specific antibody (the idiotype antibody). This subclass of anti-idiotype antibodies, which present internal images of the EP II specific antibody binding epitope, can be distinguished from anti-idiotype antibodies that recognize framework determinants in the variable region of the idiotype antibody by any of several methods. One method of identifying the desired anti-idiotype antibodies is a competitive binding assay between the EP II domain or fragment thereof, e.g., $LFY^{433}$) or hapten if available), the idiotype antibody and the anti-idiotype antibody. If the antigen blocks binding of the anti-idiotype antibody to the idiotype antibody, the epitope identified by the anti-idiotype antibody is closely associated with the idiotype antibody's parotope. Another test is to determine if anti-sera to the anti-idiotype antibody is also specific for the EP II specific inhibitory antibodys. In the formulation administered to a patient, the inclusion of anti-idiotype antibodies directed to framework determinants along with the subclass directed to the idiotype antibody's parotope is acceptable. It is only necessary that the formulation contain the subclass directed to the idiotype antibody's parotope.

The preferred anti-idiotype antibody is a human antibody to minimize immunological response to the constant region to the antibody molecule. However, since relatively small doses of anti-idiotype antibody are required, heterologous antibody can be employed (e.g., mouse, rat, goat, rabbit, etc.). In the absence on any serious reaction to heterologous anti-idiotype antibody, however, such antibody may be preferred due to ease and cost of preparation. Furthermore, polyclonal anti-idiotype antibodies can be employed as well as monoclonal anti-idiotype antibodies.

Polyclonal anti-idiotype antibody can be prepared by conventional methods known in the art or obtained from the affinity purification of the EP II-specific antibodies from infected patient serum, as described above. For example, polyclonal anti-Id Ab can be produced by immunizing an animal with a monoclonal EP II-specific antibody (i.e., Id Ab). The immunized animal will produce anti-Id Ab. A subclass of this anti-idiotype antibody in the anti-sera will identify an epitope that is the parotope of the EP II-specific antibody. Anti-sera collected from the animal can be purified, for example, by sequential absorption with (i) an immobilized antibody of the same isotype as the monoclonal Id Ab, but different idiotype, to remove anti-isotypic antibodies from the anti-sera, and (ii) the immobilized monoclonal Id Ab to remove the anti-id Ab, a subclass of which will present internal images of the EP II specific antibody antigen. The anti-Id Ab can then be eluted from the bound monoclonal antibody to provide a solution substantially free of anti-isotype antibodies. This solution can then be tested for the presence of Ab that identifies the parotope of the Id Ab. A similar approach can be performed using the polyclonal antibodies isolated from patients that are chronically infected with HCV, as mentioned above. That is, the affinity purified antibodies isolated using immobilized EP II, or a fragment thereof, such as a protein containing $LFY^{433}$ can be used to immunize animals and the anti-idiotype antibodies can be purified from the serum collected from the immunized animal using a column having immobilized EP II specific antibodies. Further characterization of the anti-idiotype antibodies can be done in the neutralization assays described herein.

Monoclonal anti-idiotype antibodies substantially free of other antibodies can be isolated from the supernatant of substantially pure cultures of immortal B lymphocytes, as well. The term "immortal B lymphocyte" encompasses any relatively stable, continuous antibody-producing cell that can be maintained in culture for several months (preferably indefinitely), such as hybridomas (somatic cell hybrids of normal and malignant lymphocytes) and normal lymphocytes transformed by virus (e.g., Epstein-Barr virus) or oncogenic DNA. The production of immortal B lymphocytes from normal B lymphocytes that produce anti-isotype antibody is within the skill of the art. See, e.g., Monoclonal Antibodies (R. H. Kennett, T. J. McKearn & K. B. Bechtol 1980); M. Schreier et al., Hybridoma Techniques (Cold Spring Harbor Laboratory 1980); Monoclonal Antibodies and T-Cell Hybridomas (G. J. Hammerling, U. Hammerling & J. F. Kearney 1981); Kozbor et al., (1982) Proc. Natl. Acad. Sci. U.S.A. 79:6651-6655; Jonak et al., (1983) Hybridoma 2:124; Monoclonal Antibodies and Functional Cell Lines (R. H. Kennett, K. B. Bechtol & T. J. McKearn 1983); Kozbor et al., (1983) Immunology Today 4: 72-79.

Normal B lymphocytes producing anti-Id Ab and suitable for the production of an immortal B lymphocyte can be provided by various methods within the skill of the art. For example, an animal, such as a rat or mouse, can be immunized with a monoclonal anti-EP II antibody and B lymphocytes producing anti-Id Ab are recovered from the animal's spleen. Human B lymphocytes producing anti-Id Ab can be obtained by immunizing a patient or chimpanzee with the polyclonal antibodies isolated from patients that are chronically infected with HCV, collecting peripheral blood lymphocytes from the patient or chimpanzee, and then inducing in vitro the growth of B lymphocytes producing anti-Id Ab by stimulating the culture with the monoclonal antibody. See, e.g., DeFreitas et al., (1982) Proc. Natl. Acad. Sci. U.S.A. 79:6646-6650. The animal or human B lymphocytes producing anti-Id Ab can thus be recovered and immortalized by those of skill in the art. Of course it is understood that those lymphocytes producing anti-Id Ab that present internal images of the EP II-specific antibody binding antigen should be distinguished from B lymphocytes producing anti-Id Ab directed to framework determinants in the idiotypic region. The anti-idiotype antibodies and binding fragments thereof can also be synthetically conjugated to the gal epitope, as described above so as to generate inhibitors that are rapidly cleared from the body.

Alternatively, DNA aptamers that mimic epitope II can be used as inhibitors of the interfering antibodies. A DNA aptamer that corresponds to the $LFY^{443}$ domain has been created. DNA aptamers that are synthetically conjugated to the gal epitope using conventional chemistry can also be created. Other chemical inhibitors that mimic the $LFY^{443}$ domain or alternative sequences with EP II can also be developed by screening chemical libraries for compounds that resemble the $LFY^{443}$ domain or other regions of EP II as described below. These chemical-based inhibitors can also be included in pharmaceuticals that are provided to patients suffering from HCV so as to improve neutralization of the virus.

Variations and derivatives of the inhibitors described above, which maintain, and preferably improve, its functional or pharmacological characteristics are also embodiments. For example, modified peptide sequences can be readily prepared and tested by routine techniques for preferred binding characteristics so as to more effectively compete against the native interfering epitope. Such modification may involve substitution, deletion or insertion of amino acids or their chemical modification. For example, longer lived decoyants may be obtained in this manner. As enzymatic degradation of the decoyants in vivo may cause some decoyants to be relatively short-lived, one method of preventing such degradation would be by making synthetic peptides containing d-amino acids. Alternatively, based on the ligand-receptor blueprint, organic molecules, i.e., not proteinaceous, can be designed so as to satisfy the physico-chemical requirements of a decoys, which form a functional interface with the interfering antibody.

It should further be understood that the decoys/inhibitors can be modified by extending the polypeptide or by adding specific chemical moieties intended to aid in drug design or to permit the decoyants to be used for additional utilities. One such modification would be to extend the polypeptide by moieties intended to affect solubility, e.g., by the addition of a hydrophilic residue, such as serine, or a charged residue, such as glutamic acid. Furthermore, the decoyant could be extended for the purpose of stabilization and preservation of a desired conformation, such as by adding cysteine residues for the formation of disulfide bridges.

Another reason to modify the decoys would be to make it detectable, even after administration. This might be done by radioiodination with a radioactive iodine isotope, directly, or by adding tyrosine for subsequent radioiodination. Such detectable decoys could be used to detect the presence and/or location of interfering antibodies. Depending, the decoy dosage could be adjusted accordingly.

The inhibitors may be administered to an animal, including a human patient, in order to ameliorate the undesired effects of the interfering antibodies for which it was designed. The specific effective dosages for the treatment of HCV can readily be empirically determined by those of ordinary skill in the art without undue experimentation. However, those skilled in the art will understand that the dosage of inhibitor will depend to some extent on the amount of interfering antibodies in the system of the host. The ratio of inhibitor to interfering antibody molecules is preferably in the range of 1:1 to 1:10. Animal tests have shown that a large excess of decoyant is not necessary for effectiveness. Preferably, the amount of interfering antibodies in the bloodstream of the host will be monitored and the decoyant dosage adjusted accordingly during the course of treatment.

As with the other compositions described herein, the decoys and inhibitors described above can be formulated into pharmaceutical compositions and may contain suitable pharmaceutically acceptable carriers comprising excipients and auxiliaries which facilitate processing of the active compounds into preparations, which can be used pharmaceutically. Preferably, the preparation, particularly those which can be administered by injection, contain from about 0.1 to 99 percent, and preferably from about 25 to 85 percent by weight, of the active ingredient, together with the excipient. Any conventional route of administration may be used, although the preferred mode of administration is by injection, e.g., intravenously, intradermally, intraperitoneally, etc, they may also be administered orally, by suppository or by any other route.

The pharmaceutical inhibitor preparations can be manufactured in a manner, which is itself known, for example, by means of conventional mixing, dissolving, or lyophilizing processes. Suitable formulations for parenteral administration include aqueous solutions of the active compounds in water-soluble form. In addition, suspensions of the active compounds as appropriate oily injection suspensions may be administered. Suitable lipophilic solvents or vehicles include fatty oils such as sesame oil, or synthetic fatty acid esters such as ethyl oleate or triglycerides. Aqueous injection suspensions may contain substances which increase the viscosity of the suspension such as sodium carboxymethyl cellulose, sorbitol, and/or dextran. Optionally, the suspension may also contain stabilizers. The inhibitors may also be administered in the form of liposomes, pharmaceutical compositions in which the active ingredient is contained either dispersed or variously present in corpuscles consisting of aqueous concentric layers adherent to lipidic layers. The active ingredient may be present both in the aqueous layer and in the lipidic layer, or, in any event, in the non-homogeneous system generally known as a liposomic suspension. The next section describes in greater detail some of the diagnostic embodiments.

Diagnostics

Additionally, the amounts of HCV neutralizing antibodies and EP II-specific inhibitory antibodies can be determined using specific "epitope-based" neutralization assays for monitoring the presence of HCV neutralizing antibody titer in patients' plasma and HCIGIV products. Currently, the level of anti-HCV antibody is measured by using recombinant HCV envelope proteins (Davis, G. L. et al. 2005 *Liver Transpl* 11:941-949; Schiano, T. D. et al. 2006 *Liver Transpl* 12:1381-1389). However, binding of antibody to nonneutralization epitope(s) can lead to an overestimation of the actual level of neutralizing antibodies in HCIGIV preparations, as well as in patients' plasma. Therefore, the epitopes identified in the present study may provide the basis for the design of potency assays more reflective of the neutralization capacities of HCIGIV preparations. Additionally, such diagnostics can be used to identify subjects in need of EP It specific antibody inhibitors. Accordingly, some embodiments include improved diagnostic assays wherein a biological sample obtained from an HCV infected patient is contacted with a composition comprising EP II (e.g., an immobilized peptide having the EP II domain or the LFY$^{443}$ and the presence or absence or amount of neutralization inhibitory antibodies present in the sample is measured by observing an interaction (e.g., binding) of the antibody with the immobilized peptide having the EP II domain or the LFY$^{443}$ or LLY$^{443}$ sequence (e.g., a peptide that is at least, equal to, less than, or greater than 5, 6, 7, 8, 9, 10, 11, 12, 13, 14, 15, 16, 17, 18, 19, 20, 21, 22, 23, 24, 25, 26, 27, 28, 30, 40, or 50 amino acids in length containing the LFY$^{443}$ or LLY$^{443}$ sequence, such as SEQ. ID. NOs. 30, 31, 33, 34, 36, 38, 41, 42, or 43). Optionally, the patient is identified as a subject in need of a determination of the presence or absence of antibodies that inhibit the binding of neutralizing antibodies and such an identification may involve a determination (e.g., clinical evaluation) as to whether said subject has chronic HCV.

Example 1

This example describes experiments that confirmed that HCIGIV contained HCV neutralizing antibodies and competing and/or interfering antibodies that inhibit the binding of the HCV neutralizing antibodies. The experiments described in this example also identify and characterize the epitopes onto which the neutralizing antibodies and competing and/or interfering antibodies interact, setting the stage for an elaborate competition that dictates whether HCV neutralization will occur.

Figure 2A:
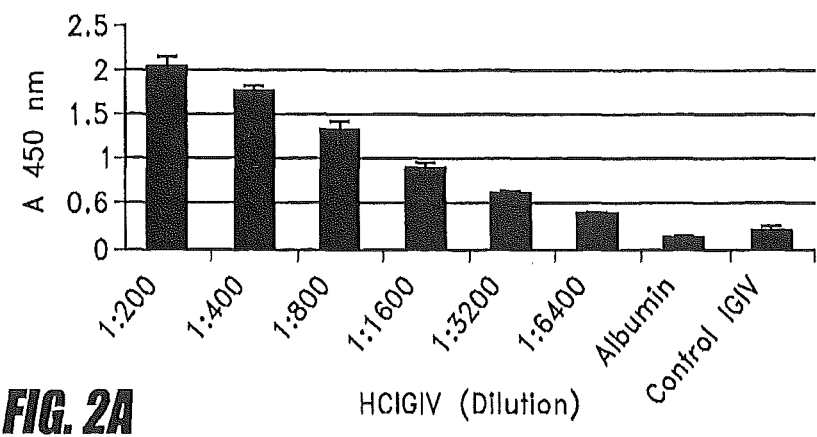
Figure 2B:
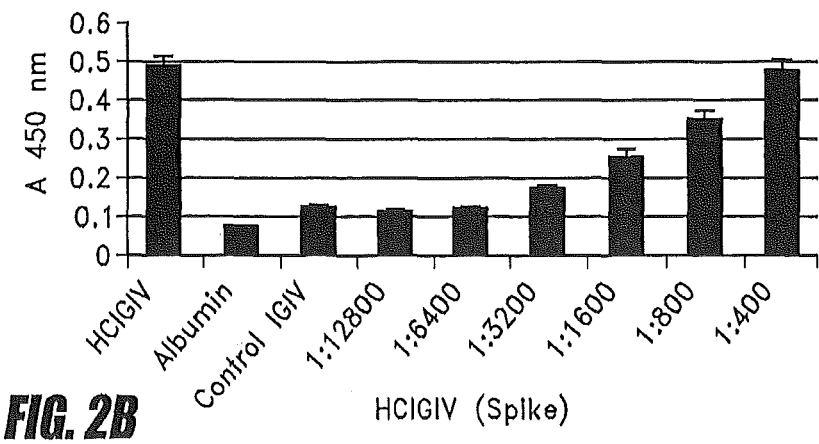

To determine whether any epitope within this segment could be recognized by human Igs, HCIGIV was tested for its ability to bind a 36-aa-long peptide (peptide A; amino acids 412-447) derived from the E2 protein (FIG. 1). As shown in FIG. 2A, HCIGIV reacted with peptide A in a dose-dependent manner and remained positive up to a dilution of 1:3,200. Negative controls, albumin and a commercial Ig intravenous (IGIV) made from anti-HCV-negative plasma, did not react with peptide A. In the second experiment, HCIGIV at different dilutions was added to the control IGIV. Binding of these Ig mixtures to peptide A could be observed at dilutions up through 1:3,200 (FIG. 2B). These results indicate that HCIGIV contains antibodies specific to epitope(s) within the HCV E2 protein between residues 412 and 447. Because each peptide was biotinylated at the C terminus (FIG. 1), streptavidin-coated plates were then used to immobilize the peptide. After affinity binding of HCIGIV, eluted antibodies specific for each peptide (peptide A, B, C, D, or N) were collected; these eluates were designated $A_E$, $B_E$, $C_E$, $D_E$, and $N_E$, respectively. Experiments were carried out to examine the specific binding of each eluate to individual peptides.

Figure 3:
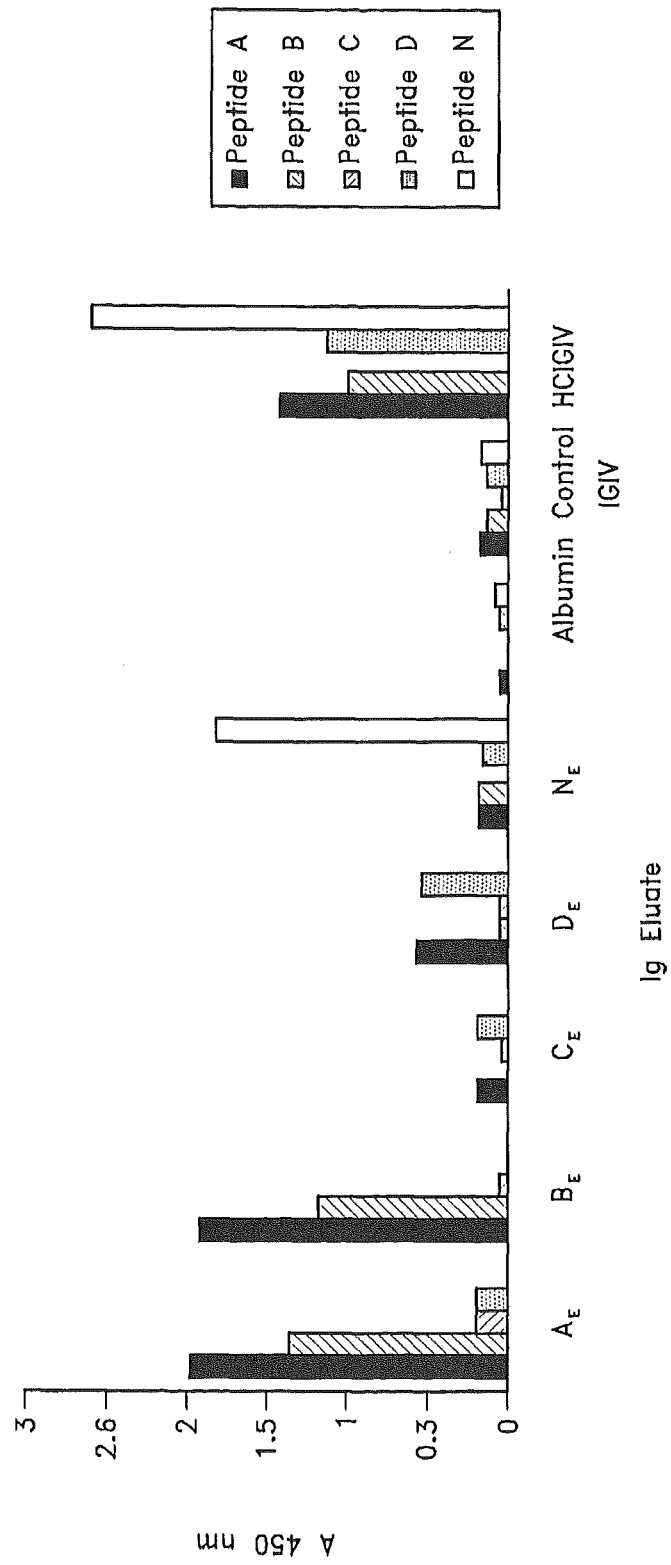

As shown in FIGS. 3 and 4A, $A_E$ reacted with peptide A. It also reacted with peptide B, but not with peptide C, D, or N. Similarly, $B_E$ reacted only with peptide A and peptide B. Under the experimental conditions used, $C_E$ exhibited no detectable binding activity for any of these peptides, suggesting that there was no epitope within peptide C that was recognizable by $C_E$. $D_E$ bound equally to peptide A and peptide D, although its overall binding activity for peptide A was only about one-fourth that of $A_E$. Although HCIGIV, as a positive control, could recognize all of the peptides tested, the binding was much stronger for peptide A, B, D, or N than for peptide C. As negative controls, albumin and control IGIV did not bind to any of these peptides. These data suggest that this region of the E2 protein contains two epitopes: epitope I at amino acids 412-419 and epitope II at amino acids 434-446, respectively (FIG. 4B).

$B_E$ reacted with peptide A more strongly than it did with peptide B (FIGS. 3 and 4A). This difference provided evidence that deletion of the N-terminal sequence 412-426 and amino acid residue 447 reduced antibody binding to epitope II, implying that amino acids 412-426 and/or 447 could enhance antibody binding to epitope II at amino acids 434-446. This conclusion, in turn, suggested a conformational nature of epitope II.

Surprisingly, $A_E$ did not exhibit detectable binding activity for peptide D, which had been previously shown to include epitope I. This observation provided evidence that most, if not all, of the activity in $A_E$ was directed against epitope II. By contrast, $D_E$ reacted equally with both peptide A and peptide D (FIGS. 3 and 4A). These results indicated that deletion of C-terminal residues 427-447 or depletion of epitope II-binding antibodies from HCIGIV permitted antibody binding to epitope I. Thus, it appeared that antibody binding to epitope II concurrently disrupted antibody recognition of epitope I. In control experiments, NE reacted only with peptide N (FIGS. 3 and 4A); the control IGIV and albumin contained no detectable antibody-binding activity to any of the peptides tested (FIG. 3).

To characterize further the nature of epitope II, $A_E$ was used to screen a random peptide phage display library. Two major clusters of phage were recognized by antibodies in $A_E$ (FIG. 5A). The phage-displayed peptides had a significant sequence homology with peptide A. 441LFY443 appeared to constitute the key residues for antibody binding. These observations prompted further examination of epitope II by an analysis of sequence alignment of the six major HCV genotypes (Owsianka, A. et al. 2005 *J Virol* 79:11095-11104; Yanagi, M. et al. 1997 *Proc Natl Acad Sci USA* 94:8738-8743). In contrast to epitope I, which had only four variant amino acids among genotypes (at residues 412, 413, 414, and 416), epitope II showed multiple variations among these genotypes, particularly in residues 444-146 (FIG. 5B). However, the peptide sequence containing 441LFY443 appeared to be conserved.

Figures 6A, 6B:
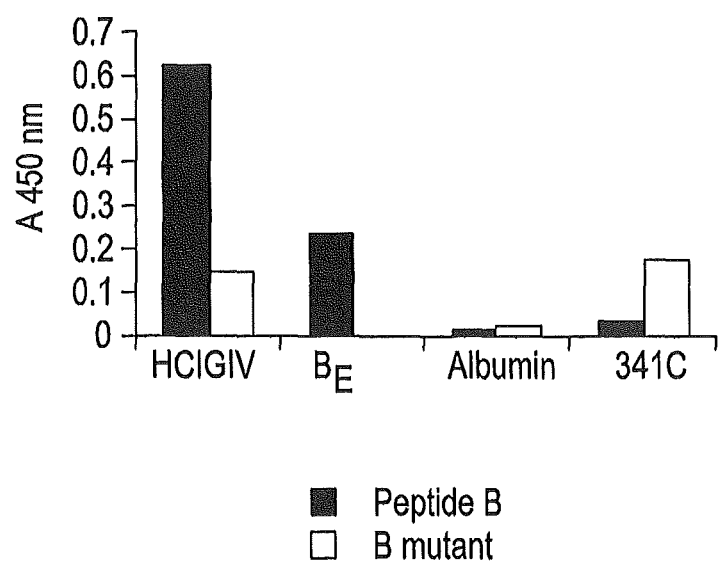

A mutation within epitope II (including residues 441LFY443) was then introduced to determine if the perturbation would disrupt antibody binding. The peptide sequence 439AGLFYQH445 (SEQ ID NO: 44) was replaced by an epitope (NAPATV, SEQ ID. NO: 28) from the severe acute respiratory syndrome virus in the context of peptide B (FIG. 6A). As a consequence of this substitution, the binding activity of $B_E$ for peptide B mutant was eliminated (FIG. 6B). Similarly, the substitution also resulted in significant loss of antibody binding to epitope II by HCIGIV. In a control experiment, the mutant could be recognized by 341C, a monoclonal antibody specific for the severe acute respiratory syndrome epitope. These data confirmed that there are at least two epitopes in the HCV envelope protein, one at amino acids 412-419 and the other at amino acids 434-446.

Figure 7A:
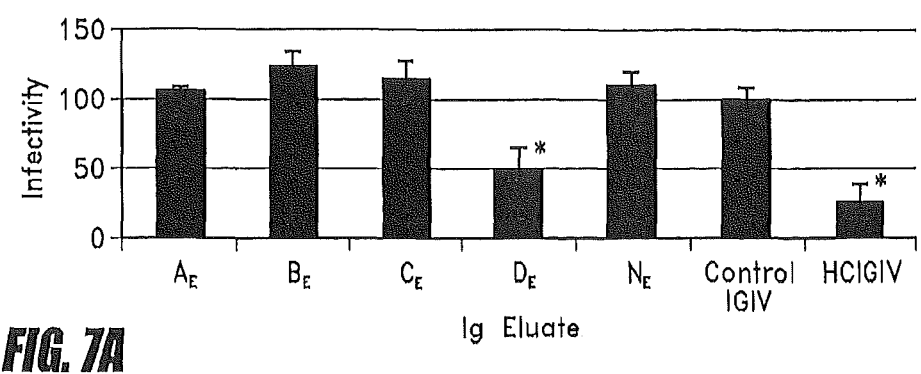
Figure 7B:
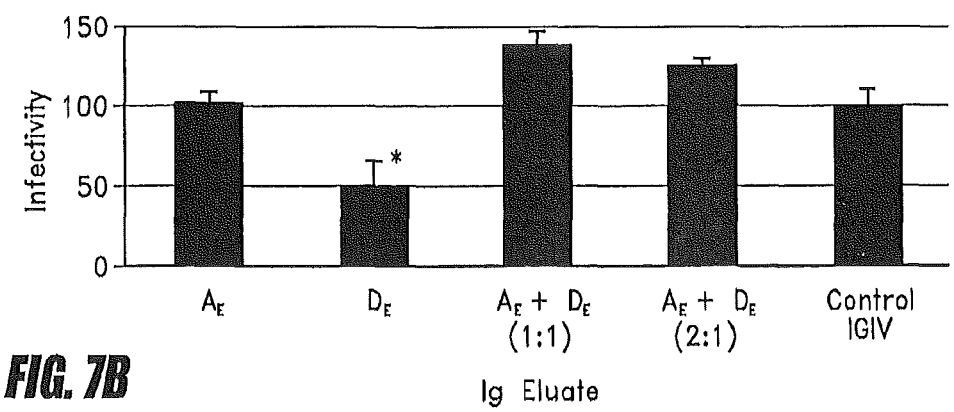

Next, the capacity of each HCIGIV eluate to block virus entry in a cell culture model was investigated. In this study, the virus stock was generated based on a chimera of genotype 2a. $A_E$, $B_E$, $C_E$, and $N_E$ did not cause any significant reduction of virus entry (FIG. 7A). By contrast, $D_E$ at 1:40 dilution neutralized HCV (P<0.05). The neutralizing activity of $D_E$ was then tested in the presence of AE (FIG. 7B). When AE was mixed with $D_E$ at a ratio of 1:1 or 2:1, neutralizing activity, which had been previously observed with $D_E$, was no longer detectable (P<0.05). These data provided strong evidence that the binding of neutralizing antibodies to epitope I (EP I) was likely blocked by the presence of nonneutralizing antibodies specific to epitope II (EP II).

Example 2

Figure 8A:
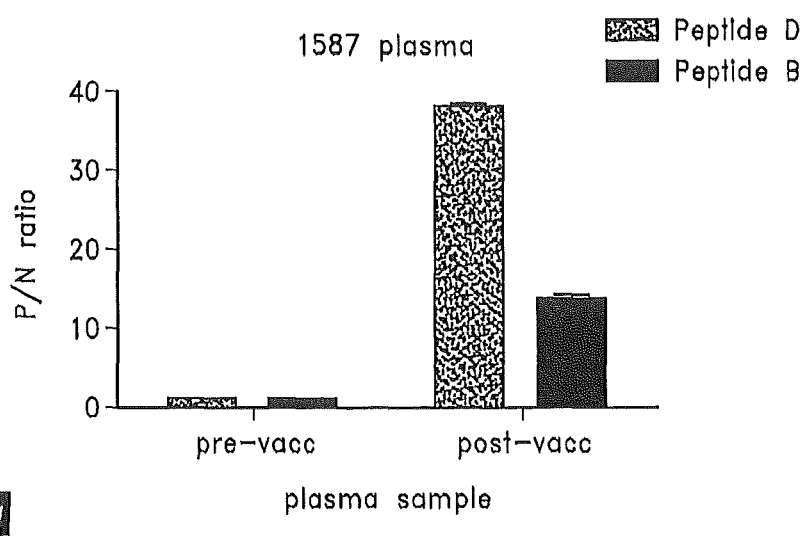
Figure 8B:
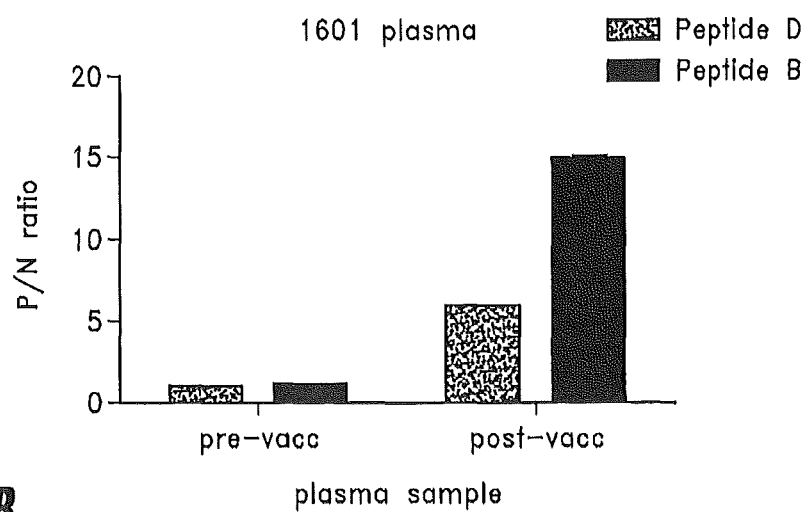
Figure 9:
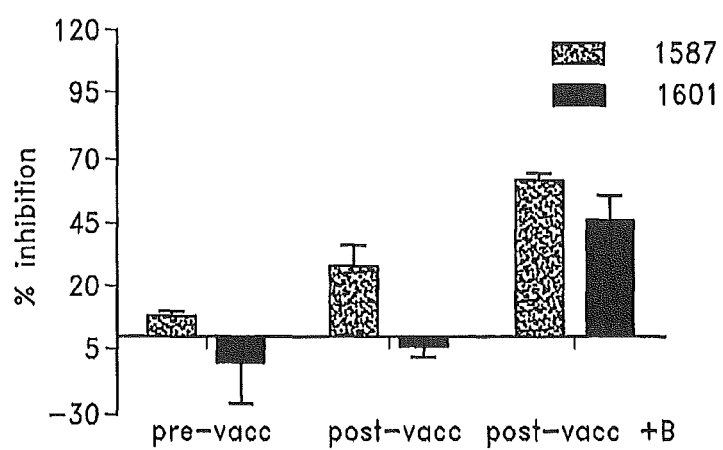

This example describes experiments that show that the competing and/or interfering antibodies that inhibit binding of the HCV neutralizing antibodies can be specifically depleted from plasma obtained from a subject infected with HCV. Plasma from two chimpanzees (1587 and 1601) vaccinated with recombinant E1E2 (genotype 1a) resulted in the generation of E1E2-specific antibodies as assessed by ELISA and inhibited genotype 1a virus replication in these animals (Puig, M. et al. 2004 *Vaccine* 22:991-1000). Post vaccine plasma samples from both animals contained antibodies to the B and D peptides (FIG. 8). Despite the presence of antibodies to the D epitope and conservation of this epitope in the 2a genome the plasma samples did not neutralize a genotype 2a virus (FIG. 9). Depletion of the chimpanzee plasma with the B peptide led to neutralization of the 2a genotype virus (FIG. 9).

For depletion studies, 100 μl of plasma was mixed with 1 μg of peptide and incubated at 37° C. for 60 minutes. Neutralization assays were set up using depleted and non-depleted plasma samples diluted 1:100 in PBS and 50 focus forming units (ffu) of a 2a (J6/JFH1) HCVcc, shown to grow in cell culture. Control neutralizations were set up with 50 ffu of virus combined with pre vaccination sera diluted 1:100 or PBS only. Next, 60 μl of virus and plasma or virus and PBS were combined, incubated at 37° C. for 60 minutes and 100 μl inoculated onto Huh7.5 cells in a 96 well plate. Samples were left to adsorb for 3 hrs after which another 100 μl of complete DMEM was added. Plates were incubated at 37° C. for 72 hrs. Cells were then fixed in ice cold isopropanol for 15 minutes at 4° C. and stained with antibody specific for HCV non structural proteins followed by secondary staining with FITC labeled anti-human IgG antibody. Foci were counted and % inhibition with depleted and non-depleted plasma calculated relative to virus incubated with PBS only.

Example 3

This example describes more experiments that were conducted to characterize the neutralization epitope I (EP I) and the inhibition epitope (EP II). Epitope I at residues 412-426 (FIG. 10A) is a highly conserved immune determinant for the neutralization of HCV as measured in vitro. To further characterize this neutralization epitope, the residues responsible for the antibody recognition were mapped by screening random peptide phage display libraries with Epitope I-specific antibodies derived from human immune globulin preparations. Three sets of phage-displayed peptides that were bound by Epitope I-specific antibodies were identified, i.e., Eluate I (FIG. 10A). The first set of peptides contained residues Q, L, SW and IN, which mimicked the wild-type sequence of the Epitope I, suggesting that QL and SW residues within Epitope I served as the "contacts" for Eluate I. Indeed, it was found that the first set of peptide mimics alone was sufficient for the binding by Eluate I. The other two sets of peptides appeared to contain residues that mimicked Epitope I partially. It was reasoned that a functional Epitope I could be formed by providing these two sets of peptides, i.e., QLGTLVAGVHPR (SEQ. ID. No: 17) and SHHDNSWVTDDY (SEQ. ID. No: 18) simultaneously in trans (FIGS. 10A and B). When these two clusters of phage-displayed peptides were tested individually, they could not be recognized by the antibody. However, when these two sets of phage were mixed at a 1:1 ratio, the combination was recognized by the antibodies in Eluate I, indicating that these phage-displayed peptides could cooperatively create an antibody binding site mimicking the conformation of Epitope I (FIG. 10B). Phage sequences TMNWIHPNGGPG (SEQ ID NO: 20), and KWTTNHRYVPLH (SEQ ID NO: 21) were also analyzed. A series of mutations within Epitope I were then introduced. Replacement of QL or SW by AA significantly reduced the binding of the antibody, (FIG. 10C).

Figures 11A, 11B:
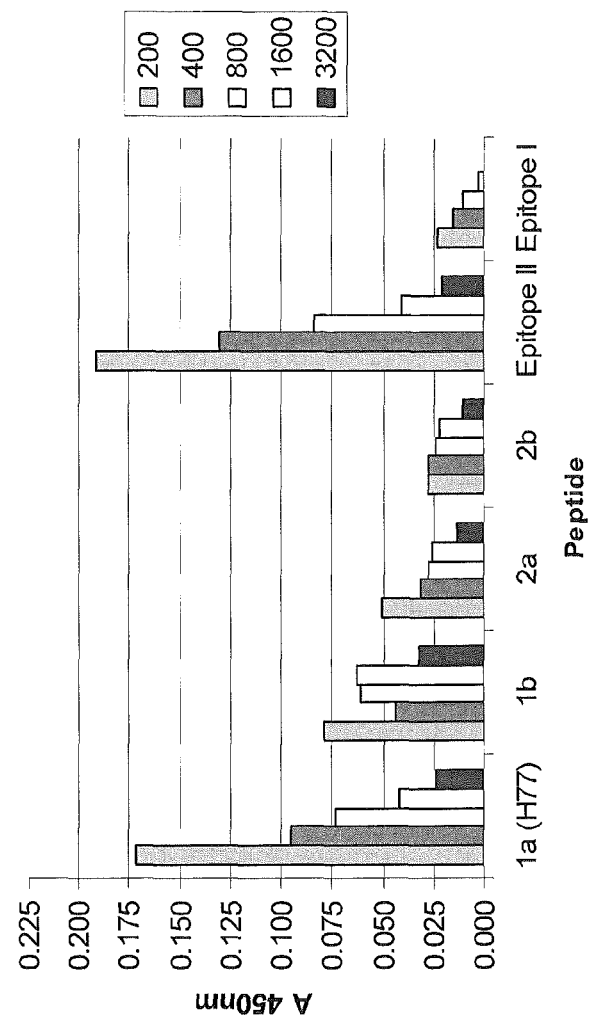

The binding of neutralizing antibody to Epitope I could be inhibited, possibly through steric hindrance, by the binding of interfering antibodies to Epitope II, which is located downstream of Epitope I at residues 434-446. In contrast to Epitope I, Epitope II has a high degree of heterogeneity among different HCV genotypes. Accordingly, experiments were designed to determine whether Epitope II-specific antibodies elicited against one genotype would cross-react with Epitope II variants in other genotypes. Peptides representing Epitope II in genotypes 1a, 1b, 2a and 2b were synthesized (FIG. 11A). Antibodies directed against Epitope II of genotype 1a, namely Eluate II, were prepared by affinity binding/elution of the HCIGIV with peptides encompassing residues 427-446 of genotype 1a (FIG. 11A). As expected, Eluate II reacted with the full Epitope II, but did not react with Epitope I. Eluate II was able to bind to Epitope II peptides derived from genotypes 1a derived from H77, 1b, 2a and 2b, respectively, in a dose-dependent manner, suggesting that the most conserved residues within Epitope II, including $^{435}TG^{436}$, $A^{439}$ and $^{441}LFY^{443}$, played an essential role in antibody recognition. However, Eluate II responded differentially to Epitope II variants present in these genotypes. For example, the antibody reacted with peptides derived from genotype 1a and 1b stronger than those from genotype 2a and 2b. Interestingly, removal of the N-terminal 7 residues from Epitope II (H77) did not significantly change the recognition by Eluate II, indicating that residues 434-446 were sufficient for antibody binding.

Example 4

Figure 12:
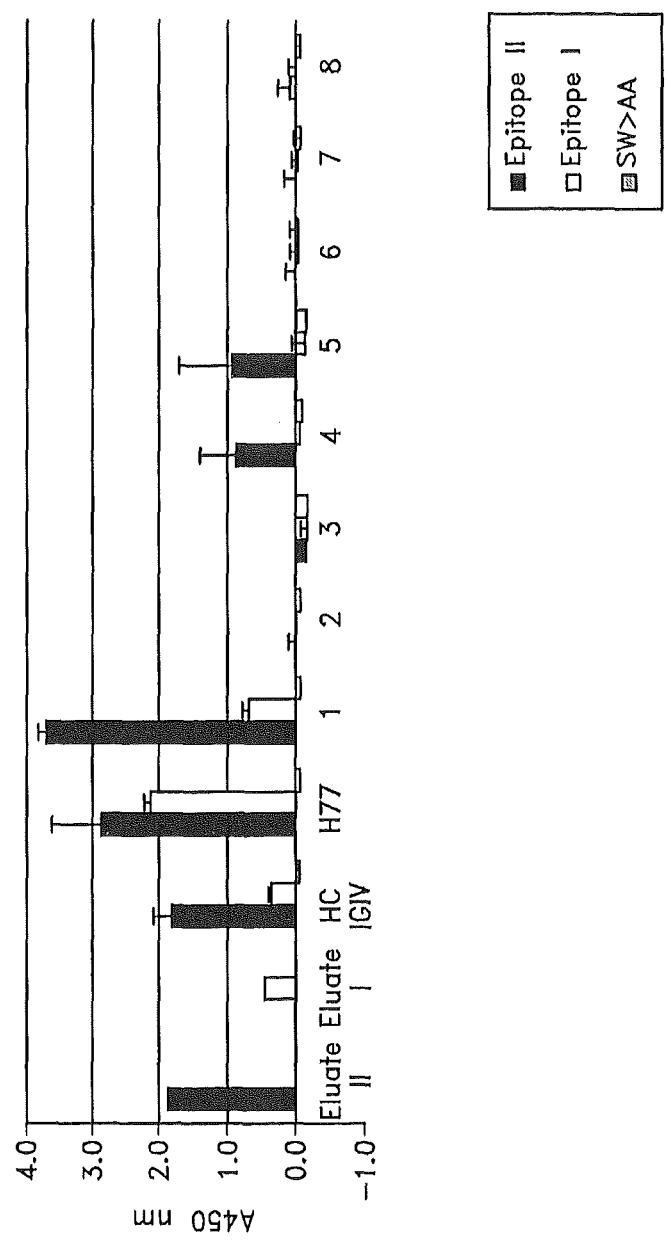
Figure 13:
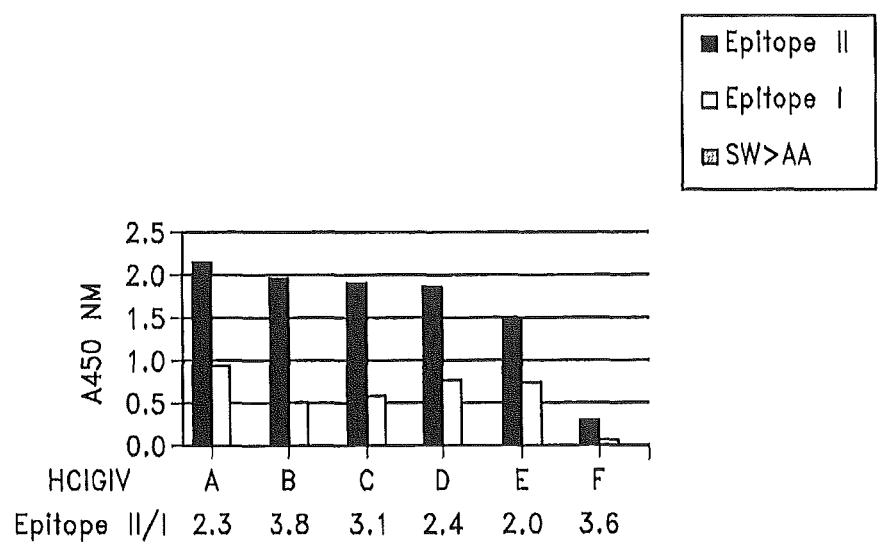

This example describes experiments that confirmed the presence of Epitope I-specific neutralizing and Epitope II-specific interfering antibodies in plasma of chronically HCV infected patients and HCIGIV. The levels of Epitope I- and Epitope II-specific antibodies in plasma of chronically HCV-infected patients was analyzed (FIG. 12). It was found that 22% of the patients in the study had detectable neutralizing antibodies directed against Epitope I, whereas 44% of the patients had antibodies against Epitope II. When Epitope I-specific antibodies were found, they occurred in the presence of elevated levels of Epitope II-specific antibodies. In view of the fact that antibody binding to Epitope II appears to interfere with the neutralizing antibody binding to Epitope I, this result provided strong evidence that the interplay between neutralizing and interfering antibodies is responsible for the persistence of HCV infections. Accordingly, the levels of Epitope I- and Epitope II-specific antibodies in several lots of HCIGIV, which were prepared from plasma pools of anti-HCV positive donors was analyzed (FIG. 13). As predicted from the prevalence of antibodies in our sample of chronically infected patients' plasma, all of the lots contained Epitope I- and Epitope II-specific antibodies. The antibody ratios, Epitope II-specific/Epitope I-specific, ranged from 2.0 to 3.8.

Example 5

Figure 14:
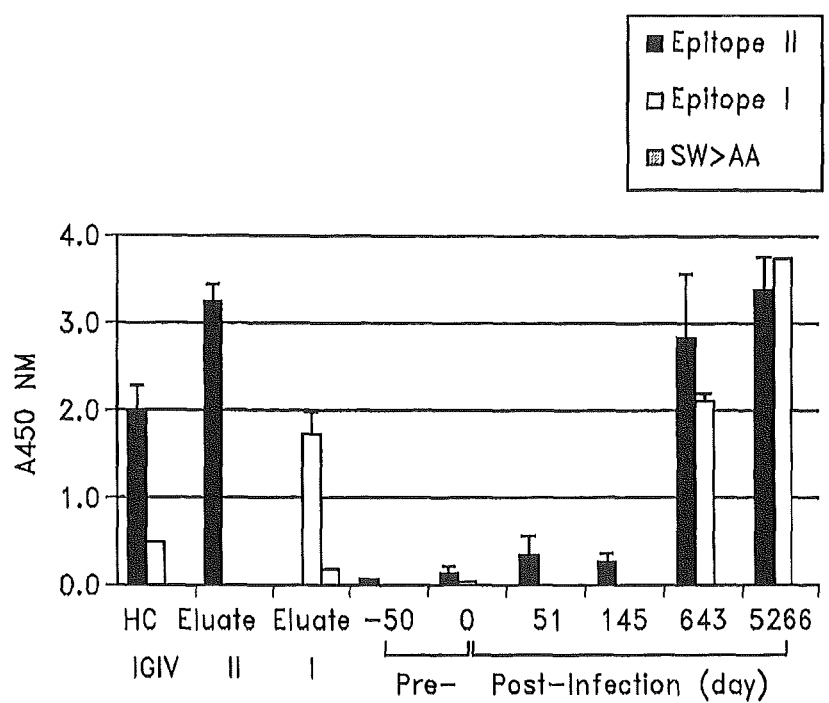

This example describes experiments that correlated the establishment of HCV chronicity and the appearance of the interfering antibody directed to EP II. To investigate whether the appearance of interfering antibody is correlated with the establishment of chronicity, the kinetics of Epitope I- and Epitope II-specific antibody production in the plasma of a patient (H77) who had established chronic infection (FIG. 14) was analyzed. It was found that the antibody response directed against Epitope II was detectable within 51 days after infection. By day 643, the antibody level was increased significantly, and it was maintained at high level thereafter. By contrast, no Epitope I-specific antibody was found in plasma available from the acute phase of HCV infection. It was first detected in the sample drawn on day 643. That appearance of Epitope I-specific antibody coincided with the presence of elevated levels of Epitope II-specific antibody in the chronic phase of HCV infection.

Example 6

This example describes experiments that showed that neutralization of HCV in plasma obtained from a chronically HCV infected patient could be restored after depletion of Epitope II-specific antibodies. Absence of neutralizing antibody directed to Epitope I during the acute phase of HCV infection and co-existence of Epitope I- and Epitope II-specific antibody during the chronic phase of HCV infection indicated that the interplay between this pair of antibodies was related to the establishment of chronicity. Experiments were then designed to determine whether the depletion of Epitone II-specific antibodies from the plasma of patient H77 would enhance the neutralizing activity of the plasma collected after the establishment of chronic HCV infection (FIG. 15). By using affinity absorption with Epitope II peptide (FIG. 15A), the level of Epitope II-specific antibody was significantly lowered (FIG. 15B). Absorption with Epitope II mutant resulted in a much smaller decrease (FIG. 15B). As determined by using HCV cell culture, reduction of the level of Epitope II-specific antibody in the plasma led to the recovery of the neutralizing activity ($p<0.05$) (FIG. 15C). Absorption with the mutant peptide did not significantly affect the neutralizing activity (FIG. 15C). Patient H77, whose plasma was used in these experiments, was infected with genotype 1a virus. However, his plasma was able to neutralize genotype 2a virus when interfering antibodies directed against Epitope II were removed.

Example 7

This example provides greater detail on some approaches to make EPII antibody specific anti-idiotype and anti-anti-idiotype antibodies. By one approach, polyclonal anti-idiotype antibodies are prepared as follows. Plasma obtained from chronically infected HCV patients that have been identified as having anti-EP II antibodies is obtained and the anti-EPII antibodies are isolated by affinity purification, as described herein. New Zealand white rabbits are then injected subcutaneously at multiple sites with 300 ug purified EP II specific antibody emulsified in Freund's complete adjuvant and, 30 days later, boosted intramuscularly with 100 ug of the antibody. Sera is collected on day 10 of the secondary response.

Anti-serum is then absorbed on immobilized EP II specific antibody. The purified EP II specific antibodies (30 mg each) are coupled to 2 ml of Affi-Gel® 10 (Bio-Rad Laboratories, Richmond, Calif). The anti-serum is then sequentially absorbed on EP II specific antibody immunoabsorbents to remove anti-isotypic and anti-idiotypic antibodies, respectively. Absorbed antibodies are eluted with 0.1M glycine buffer (pH 2.8), immediately neutralized with phosphate buffer, dialyzed against phosphate-buffered saline, and protein quantitated by absorptivity at 280 nm. To screen serum samples for the presence of anti-idiotype antibody, a neutralization competition assay is performed using the rabbit-anti-idiotype antibody, the anti-EP II antibodies, and the anti-EPI antibodies, using the approaches described herein. The results will show that in the presence of the rabitt-anti-idiotype antibody, neutralization of HCV is improved despite the presence of the anti-EP II antibodies.

By another approach, the anti-idiotype and anti-anti-iditiotype antibodies are created in human B lymphocytes. Accordingly, buffy coat cells are obtained from patients that are chronically infected with HCV and that have been identified as having anti-EP II antibodies. The cells are stimulated with 10 ng/ml F(ab')$_2$ fragments of the isolated anti-EP II antibodies in vitro as described in DeFreitas et al., (1982), Proc. Natl. Acad. Sci. U.S.A. 79: 6646-6650. During the following seven days, aliquots of cells are separated into T and B cell populations by rosetting with sheep erythrocytes treated with 2-amino ethylisouronium bromide. See, Pellogrino et al., (1975) Clin. Immunol. & Immunopathol. 3: 324-333, Both cell populations are stained with F(ab')$_2$ fragments of the isolated anti-EP II antibodies. The cell populations are then subsequently analyzed in a cytofluorograph. In addition, peripheral blood mononuclear cells from the same patients are stimulated with F(ab')$_2$ fragments of the isolated anti-EP II antibodies for nine days in a modified Mishell-Dutton culture for specific human Ig production, as described in DeFreitas et al., supra. Supernatants from these cultures are assayed in a solid-phase enzyme-linked immunoabsorbent assay for specific human IgG (KPL Laboratories, Gaithersburg, Md.).

In more experiments, the human B lymphocytes are stimulated to produce anti-(anti-idiotype) antibody. B lymphocytes are collected and stimulated in vitro as described above, except that the cells are stimulated with autologous anti-idiotype antibody rather than idiotype antibody. Anti-(anti-idiotype) antibodies are produced by stimulated B lymphocytes. In still more experiments, the human B lymphocytes can be immortalized. Various methods of producing immortal B lymphocytes secreting monoclonal antibodies are known in the art. See Kozbor et al., (1983) Immunology Today 4: 72-79. Human B lymphocytes secreting anti-(anti-idiotype) antibody, obtained from peripheral blood lymphocytes as described above, can be immortalized by conventional hybridoma technology. One method that can be readily employed is immortalization with Epstein-Barr virus (EBV). In this method, the normal lymphocytes described above are infected with EBV in vitro and immortal cell lines then establish, for example, by limiting dilution on a feeder layer. See, e.g., Kozbor, et al., (1983), supra, and references 51-60 cited therein. Another approach is to fuse either the above described anti-Id Ab secreting lymphocytes or an EBV-transformed lymphocyte with a human plasmacytoma or lymphoblastoid fusion partner. For example, an EBV-transformed B lymphocyte secreting anti-Id Ab can be fused with, for example, the human lymphoblastoid cell line KR-4. The desired hybridomas would then be selected for in hypoxanthine-aminopterin-thymidine medium containing ouabain, which eliminates the parental cells. Hybridomas are tested for specific antibody production. Positive hybrids are then cloned, recloned and then propagated in bulk culture or in the peritoneal cavity of an immune-suppressed mammal (e.g., nude mouse). See, e.g., Kozbor et al., (1982) Proc. Natl. Acade. Sci. U.S.A. 79: 6651-6655.

Example 8

This example provides greater detail on some of the materials and methods employed in the experiments described herein Igs and Monoclonal Antibody Several independent lots of HCIGIV (A-F), an experimental 5% IGIV made from anti-HCV-positive plasma, was kindly provided by Nabi Biopharmaceuticals (Boca Raton, Fla.). It was made from the pooled plasma of 198 anti-HCV (EIA-2)-positive donors who otherwise met the requirements for normal plasma donations, i.e., negative for both anti-HIV and hepatitis B surface antigen and without elevated levels of alanine aminotransferase. These HCIGIV preparations had been treated by a solvent-detergent process to inactivate potential contaminating viruses. It was previously shown to neutralize HCV in both a pseudoparticle system and a chimpanzee model (Yu, M. W. et al. 2004 Proc Natl Acad Sci USA 101:7705-7710). A commercial 5% IGIV solution, which was manufactured from anti-HCV (EIA-2)-negative plasma donations, was used as a negative control. This IGIV preparation was also virally inactivated by a solvent-detergent treatment. Albumin was a commercial 25% albumin (human) that had been virally inactivated by heating at 60° C. for 10 h. It was diluted to 5% with PBS before use as a control. A murine monoclonal antibody (341C), specific for peptide NAPATV (SEQ ID NO: 28) was used as a control (Tripp, R. A. et al. 2005 *J Virol Methods* 128:21-28).

Patient Plasma

Samples were obtained at the NTH Clinical Center from 9 individuals who were chronically infected with HCV and randomly selected for this study. All samples were collected under protocols approved by the NIH IRB.

Peptide Synthesis

All peptides were synthesized by the Core Laboratory of the Center for Biologies Evaluation and Research, Food and Drug Administration, with an Applied Biosystems (Foster City, Calif.) Model 433A Peptide Synthesizer by using standard FastMoc chemistry (Barany, G. and Merrifield, R. B. The Peptides Analysis, Synthesis and Biology Gross E, Meienhofer J., editors; New York: Academic; 1980, pp. 1-284). Synthesis of biotinylated peptides was carried out with Fmoc-Lys (Biotin-LC)-Wang resin (AnaSpec, San Jose, Calif.). The crude peptides were precipitated, washed with butyl methyl ether, dried under vacuum, purified by RP-HPLC by using a DeltaPak C-18 reversed-phase column (Waters, Milford, Mass.), and analyzed by MALDI-TOF MS on a Voyager DE-RP™ MALDI-TOF mass spectrometer (Applied Biosystems or PE Biosystems).

Affinity Binding and Elution

In some experiments, biotinylated peptides (100 ng) were incubated for 1 h at room temperature in each well of 96-well plates precoated with streptavidin in PBS (pH 7.4) containing 0.05% Tween® 20 (PBS-T). After blocking with blocking buffer (Blocker™ BSA; Pierce, Rockford, Ill.), an appropriately diluted antibody was added to the well and incubated for 1 h. After 10 washes with PBS-T, the bound antibody was eluted with 0.2 M glycine-HCl buffer (pH 2.2) for 10 min at room temperature and neutralized immediately with 1 M Tris-HCl (pH 9.1). In other experiments, for affinity binding/elution, streptavidin-coated 96-well plates were used according to the manufacturer's instructions (Pierce, Mass.). Biotinylated peptides (500 ng in 100 μl) were added to streptavidin-coated wells and incubated for 30 min at room temperature in 0.01 M phosphate saline buffer (pH 7.4) containing 0.05% Tween 20 (PBS-T). After blocking with Super-Blocker® Blocking Buffer (Thermo Scientific, Rockford, Ill.) for 1 hr at 37° C., an appropriately diluted antibody was added to the well and incubated for 1 hr at room temperature for absorption. After extensive washing with PBS-T, the bound antibody was eluted with 0.2 M glycine-HCl buffer pH 2.2 for 10 min at room temperature and neutralized immediately with 1 M Tris-HCl, pH 9.1. Eluate I was prepared by affinity binding/elution of HCIGIV lot A using Epitope I peptide, whereas Eluate II was prepared by using Epitope II peptide. Similarly, for affinity depletion, multiple absorption steps using specific peptides were performed to deplete unwanted antibodies. Solutions remaining after absorption were collected for further study.

ELISA

Streptavidin-coated 96-well plates were used for ELISA according to the manufacturer's instructions (Pierce). Briefly, biotinylated peptides (100 ng in 100 μl) were added to streptavidin-coated wells 30 min at room temperature in PBS-T, and blocked with SuperBlocker® Blocking Buffer (Thermo Scientific, Rockford, Ill.) for 1 hr at 37° C. After washings with PBS-T, antibodies were added to the wells and incubated for 1 h at room temperature or 37° C. After removal of unbound antibodies by washing with PBS-T, a goat anti-human peroxidase-conjugated IgG (Sigma-Aldrich, St. Louis, Mo.) at 1:3,000 dilution or 1:5000 dilution was added to the wells. After washings, the plates were kept in darkness for 10 min with 100 μl of a solution containing a tablet of orthophenylene diamine dihydrochloride (Sigma-Aldrich) diluted to 0.4 mg/ml in 0.05 M phosphate/citrate buffer (pH 5.0) containing 0.03% sodium perborate (Sigma-Aldrich) or the plates were incubated in the dark for 10 min with 100 μL of 1-Step™ Ultra TMB-ELISA (Thermo Scientific Rockford, Ill.). The reaction was stopped by adding 100 μL 4 N $H_2SO_4$. The reaction was stopped in some experiments by adding 50 μl of 1 M H2SO4. The absorbance of each well was measured at 450 nm with a microliter plate reader (Optimax; Molecular Devices, Palo Alto, Calif.).

Phage Display and Epitope Reconstitution in Trans

Selection of peptides from a random peptide display-phage library (New England Biolabs, Beverly, Mass.; PhD-12) was described previously (Zhang, P. et al. 2006 Proc Natl Acad Sci USA 103:9214-9219). Briefly, approximately [≈]$10^{10}$ phages were incubated with individual Ig eluate/protein A mixtures for 20 min at room temperature. After eight washings with 0.05 M Tris-HCl buffer (pH 7.5) containing 0.15 M NaCl and 0.05% Tween® 20, the phages were eluted from the complex with 0.1 M HCl for 8 min at room temperature. The eluted phages were then amplified in the host strain ER2738. Amplified phages were subjected to three additional rounds of selection with antibody. After selection, collected phages were grown on LB-agar plates. DNA from each single-phage plaque was sequenced, and the corresponding peptide sequence was then deduced from the DNA sequence. The sequence homology of phage-displayed peptides with different HCV genotypes (Tarr, A. W. et al. 2006 Hepatology 43:592-601; Yanagi, M. et al. 1997 Proc Natl Acad Sci USA 94:8738-8743) was determined.

For epitope reconstitution, individual phage clones containing mimics of HCV Epitope I were selected, and their plaque forming units (pfu) were determined by transduction of host strain ER2738. Appropriately diluted portions of phage clones were mixed, individually or in combination, with Eluate I/Protein G complex and incubated at room temperature for 20 min. After eight washings with TBS-T, the phages were eluted from the complex with 0.1 M HCl for 8 min at room temperature. Plaque assays were performed as indicated above, and the numbers of plaques formed were counted.

Neutralization Assays

FL-J6/JFH1 virus was a gift from Charles Rice at the Rockefeller University (New York, N.Y.). Virus stock was prepared by infecting Huh 7.5 cells according to the procedures described previously (Kato, T. et al. 2003 Gastroenterology 125:1808-1817; Lindenbach, B. D. et al. 2005 Science 309:623-626; Lindenbach, B. D. et al. 2006 Proc Natl Acad Sci USA 103:3805-3809). For the neutralization assay, Huh 7.5 cells were seeded at a density of 4-5 $10^3$ cells per well in 96-well plates to obtain 50-60% confluence after 24 h. The virus stock was titrated in Huh 7.5 cells, and a dilution was selected that would give approximately [≈] 50 immunostained foci per 50 μl. This dilution was chosen because, in the final incubation of the test for neutralization capacity (see below), each well contained 50 μl of the virus stock and an equal volume of an appropriate dilution of the antibody preparation being tested. As a control, a dilution series was prepared from the virus stock to check the input virus titer. To test neutralization capacity, 200 μl of test antibodies appropriately diluted in DMEM containing 10% FCS, in parallel with a positive (HCIGIV) and a negative control IGIV, was mixed with 200 μl of virus stock and incubated at 37° C. for 1 h. The virus/antibody mixture in aliquots of 100 μl was then added to each of four wells of the microtiter plate containing the Huh 7.5 cells. After 3 days in culture, the cells were washed, fixed with cold methanol, and then probed with a mouse monoclonal antibody directed against the HCV core antigen (kindly provided by Harry Greenberg, Stanford University School of Medicine, Stanford, Calif.), followed by washing and probing with a horseradish peroxidase-conjugated anti-mouse IgG (H and L) (Kirkegaard & Perry Laboratories, Gaithersburg, Md.). Stained foci were developed by using HistoMark True®Blue™ (Kirkegaard & Perry Laboratories). Stained foci were counted in quadruplicate wells, and the mean number of foci per well was calculated. Infectivity was expressed as a percentage of the mean number of foci per well in the negative control group. Thus, neutralizing activity was equivalent to the decrease, if any, from 100%.

In other experiments, virus stock was prepared by transfecting HCV RNA derived from a genotype 2a chimera into Huh 7.5 cells according to the procedures described previously (10,26,27). Huh 7.5 cells were seeded at a density of 4-5×$10^3$ cells/well in 96-well plates to obtain 50-60% confluence in 24 hrs, Virus stock was diluted in DMEM supplemented with 10% fetal bovine serum/1% penicillin/streptomycin/2 mM glutamine to yield approximately 100 infected foci/well in the absence of neutralizing antibodies. To test neutralization capacity, a given antibody, in parallel with a positive (HCIGIV) and a negative (IGIV) control, was mixed with the virus stock prior to adding to the cells. After incubation at 37° C. for 1 hr, the supernatants containing the virus/antibody mixture were removed by washing with PBS. The cells were continuously cultured in DMEM for 3 days. To count infected foci, the cells were fixed with cold methanol. Infected foci were counted; this was followed by peroxidase staining. Infectivity was expressed as percent of negative control, i.e., (numbers of infected foci with antibody/numbers of foci without antibody)×100%.

Statistical Analysis

JMP, version 5.0, software (SAS Institute, Cary, N.C.) was, used for analyzing data. Pairwise comparisons of the means between two Ig eluates at a time were performed by using Student's t test. For an overall comparison of means, the Tukey-Kramer honestly significant difference test was used. Statistical significance was set at $\alpha$=0.05. A positive test value generated between two means is indicative of a significant difference.

It is understood that the examples and embodiments described herein are for illustrative purposes only and that various modifications or changes in light thereof will be suggested to persons skilled in the art and are to be included within the spirit and purview of this application and scope of any appended claims. All figures, tables, as well as publications, patents, and patent applications, cited herein are hereby incorporated by reference in their entirety for all purposes.

What is claimed is:

1. A composition comprising an enriched anti-HCV-positive immunoglobulin (HCIGIV) preparation that is enriched for HCV neutralizing antibodies that bind to E2 protein Epitope I, by depletion of interfering antibodies that bind to E2 protein Epitope II.

2. The composition of claim 1, wherein the enriched HCIGIV preparation is produced by contacting a pooled anti-HCV-positive plasma preparation with an isolated peptide comprising an E2 protein Epitope II (EP II) sequence, wherein said peptide is a ligand for an antibody that inhibits neutralization of hepatitis C virus (HCV).

3. The composition of claim 2, wherein the peptide is LNCNESLNTGWLAGLFYQH (SEQ ID NO: 4).

4. The composition of claim 2, wherein the peptide comprises DTGWVAGLFYYHR (SEQ ID NO. 31), NTGFLAALFYVRN (SEQ ID NO. 33), NTGFIASLFYTHS (SEQ ID NO. 34), NTGFLAGLFYYHK (SEQ ID NO. 36), NTGFLAGLFYYHK (SEQ ID NO. 38), NTGFLAGLFYHYS (SEQ ID NO. 40), QTGFIAGLLYFNK (SEQ ID NO. 42), or QTGFIASLFYFNK (SEQ ID NO. 43).

5. The composition of claim 2, wherein the peptide comprises a sequence having at least 80% homology to NTGWLAGLFYQHK (SEQ ID NO. 30), wherein said peptide includes the TG, A and LFY residues of SEQ ID NO: 30, wherein said LFY is optionally replaced with LLY, and wherein the sequence is not LNCNESLNTGWLAGLFYQH (SEQ ID NO: 4).

6. The composition of claim 2, wherein the peptide comprises a sequence having at least 90% homology to NTGWLAGLFYQHK (SEQ ID NO. 30), wherein said peptide includes the TG, A and LFY residues of SEQ ID NO: 30, wherein LFY is optionally replaced with LLY, and wherein the sequence is not LNCNESLNTGWLAGLFYQH (SEQ ID NO: 4).

7. The composition of claim 2, wherein the peptide comprises a sequence having at least 95% homology to NTGWLAGLFYQHK (SEQ ID NO. 30), wherein said peptide includes the TG, A and LFY residues of SEQ ID NO: 30, and wherein the amino acid sequence LFY is optionally replaced with LLY, wherein the sequence is not LNCNESLNTGWLAGLFYQH (SEQ ID NO: 4).

8. The composition of claim 5, wherein said peptide is bound to a support.

9. The composition of claim 5, wherein said peptide comprises a bound gal epitope.

* * * * *